United States Patent
Baer et al.

(10) Patent No.: US 9,790,444 B2
(45) Date of Patent: Oct. 17, 2017

(54) METHODS TO PRODUCE FUELS

(71) Applicants: The Regents of the University of California, Oakland, CA (US); BP Corporation North America Inc., Houston, TX (US)

(72) Inventors: Zachary C. Baer, Glen Mills, PA (US); Harvey W. Blanch, Palm Springs, CA (US); Douglas S. Clark, Orinda, CA (US); Sanil Sreekumar, Midland, MI (US); F. Dean Toste, Piedmont, CA (US); Gorkem Gunbas, Ankara (TR); Konstantinos A. Goulas, Newark, DE (US); Amit A. Gokhale, El Cerrito, CA (US); Joseph B. Binder, Haverford, PA (US)

(73) Assignees: The Regents of the University of California, Oakland, CA (US); BP Corporation North America Inc., Houston, TX (US)

( * ) Notice: Subject to any disclaimer, the term of this patent is extended or adjusted under 35 U.S.C. 154(b) by 0 days.

(21) Appl. No.: 14/786,153

(22) PCT Filed: Apr. 25, 2014

(86) PCT No.: PCT/US2014/035545
§ 371 (c)(1),
(2) Date: Oct. 21, 2015

(87) PCT Pub. No.: WO2014/176552
PCT Pub. Date: Oct. 30, 2014

(65) Prior Publication Data
US 2016/0152907 A1   Jun. 2, 2016

Related U.S. Application Data

(60) Provisional application No. 61/816,617, filed on Apr. 26, 2013.

(51) Int. Cl.
| | | |
|---|---|---|
| *C07C 45/45* | (2006.01) | |
| *C10L 1/02* | (2006.01) | |
| *C07C 45/71* | (2006.01) | |
| *G06Q 30/00* | (2012.01) | |
| *H04L 29/08* | (2006.01) | |
| *H04L 29/06* | (2006.01) | |
| *C12P 7/26* | (2006.01) | |

(52) U.S. Cl.
CPC ............... *C10L 1/02* (2013.01); *C07C 45/45* (2013.01); *C07C 45/71* (2013.01); *C12P 7/26* (2013.01); *G06Q 30/01* (2013.01); *H04L 67/10* (2013.01); *H04L 67/42* (2013.01); *C10L 2200/0469* (2013.01); *C10L 2290/26* (2013.01); *C12P 2203/00* (2013.01); *Y02E 50/16* (2013.01); *Y02P 20/582* (2015.11)

(58) Field of Classification Search
CPC ............... C07C 45/45; C10L 1/02; C12P 7/26
See application file for complete search history.

(56) References Cited

U.S. PATENT DOCUMENTS

| | | | |
|---|---|---|---|
| 2,434,631 A | 1/1948 | Winkler et al. | |
| 3,781,307 A | 12/1973 | Chabardes et al. | |
| 4,250,259 A | 2/1981 | Hou et al. | |
| 8,075,642 B2 | 12/2011 | Dumesic et al. | |
| 2005/0089979 A1 | 4/2005 | Ezeji et al. | |
| 2007/0275447 A1 | 11/2007 | Lewis et al. | |
| 2008/0015395 A1 | 1/2008 | D'amore et al. | |
| 2008/0015397 A1 | 1/2008 | D'Amore et al. | |
| 2008/0103337 A1 | 5/2008 | D'Amore et al. | |
| 2008/0132730 A1 | 6/2008 | Manzer et al. | |
| 2008/0244961 A1 | 10/2008 | Rusek et al. | |
| 2008/0248540 A1 | 10/2008 | Yang | |
| 2009/0030239 A1 | 1/2009 | D'Amore et al. | |
| 2009/0036716 A1 | 2/2009 | D'Amore et al. | |
| 2010/0076233 A1 | 3/2010 | Cortright et al. | |
| 2010/0077655 A1* | 4/2010 | Bauldreay ................ | C10L 1/04 44/437 |
| 2010/0204526 A1 | 8/2010 | Kouba et al. | |
| 2010/0263265 A1 | 10/2010 | Delfort et al. | |
| 2010/0268005 A1 | 10/2010 | Rusek et al. | |
| 2010/0330633 A1 | 12/2010 | Walther et al. | |
| 2011/0172475 A1 | 7/2011 | Peters et al. | |

(Continued)

FOREIGN PATENT DOCUMENTS

| | | |
|---|---|---|
| CN | 101440381 A | 5/2009 |
| CN | 101787378 A | 7/2010 |
| DE | 2257675 A1 | 5/1974 |

(Continued)

OTHER PUBLICATIONS

Office Action received for Chinese Patent Application No. 201280036663.8, dated Jan. 14, 2015, 9 pages (4 pages of English Translation and 5 pages of Official).

Alonso, et al., "The α-Alkylation of Methyl Ketones with Primary Alcohols Promoted by Nickel Nanoparticles under Mild and Ligandless Conditions", Synlett, No. 12, Georg Thieme Verlag Stuttgart, 2007, pp. 1877-1880.

Das, et al., "Influence of the Metal Function in the "one-pot" Synthesis of 4-Methyl-2-Pentanone (Methyl Isobutyl Ketone) from Acetone Over Palladium Supported on Mg(Al)O Mixed Oxides Catalysts", Catalysis Letters, vol. 71, No. 3-4, Feb. 2001, pp. 181-185.

Debecker, et al., "Exploring, Tuning, and Exploiting the Basicity of Hydrotalcites for Applications in Heterogeneous Catalysis", Chemistry A European Journal, vol. 15, 2009, pp. 3920-3935.

Demirbas, A, "The Importance of Bioethanol and Biodiesel from Biomass", Energy Sources, Part B, vol. 3, 2008, pp. 177-185.

(Continued)

*Primary Examiner* — Sikarl Witherspoon
(74) *Attorney, Agent, or Firm* — Morrison & Foerster LLP

(57) ABSTRACT

The present disclosure generally relates to the catalytic conversion of alcohols into hydrocarbon ketones suitable for use as fuels. More specifically, the present disclosure relates to the catalytic conversion of a mixture of isopropanol-butanol-ethanol (IBE) or acetone-butanol-ethanol (ABE), into ketones suitable for use as fuels. The ABE or IBE mixtures may be obtained from the fermentation of biomass or sugars.

16 Claims, 11 Drawing Sheets

(56) References Cited

U.S. PATENT DOCUMENTS

| | | |
|---|---|---|
| 2011/0237833 A1 | 9/2011 | Koltermann et al. |
| 2011/0306801 A1 | 12/2011 | Schucker et al. |

FOREIGN PATENT DOCUMENTS

| | | |
|---|---|---|
| EP | 0719751 A1 | 7/1996 |
| EP | 828558 B1 | 12/2001 |
| GB | 400384 A | 10/1933 |
| GB | 723280 A | 2/1955 |
| WO | 98/51813 A1 | 11/1998 |
| WO | 2007149397 A2 | 12/2007 |
| WO | 2008/066579 A1 | 6/2008 |
| WO | 2008/066581 A1 | 6/2008 |
| WO | 2008109877 A1 | 9/2008 |
| WO | 2008111941 A2 | 9/2008 |
| WO | 2008156320 A1 | 12/2008 |
| WO | 2009152495 A2 | 12/2009 |
| WO | 2010/098694 A2 | 9/2010 |
| WO | 2011077242 A1 | 6/2011 |
| WO | 2011143392 A1 | 11/2011 |
| WO | 2012001416 A1 | 1/2012 |
| WO | 2012001417 A1 | 1/2012 |
| WO | 2012166267 A2 | 12/2012 |
| WO | 2012/166267 A3 | 4/2013 |

OTHER PUBLICATIONS

Hamid, et al., "Borrowing Hydrogen in the Activation of Alcohols", Advanced Synthesis & Catalysis, vol. 349, No. 10, Wiley-VCH Verlag GmbH&Co. KGaA, Weinheim, Jul. 2, 2007, pp. 1555-1575.

He, et al., "One-step synthesis of 2-pentanone from ethanol over K—Pd/MnOx—ZrO2—ZnO catalyst", Journal of Molecular Catalysis A: Chemical, vol. 226, 2005, pp. 89-92.

Kim, et al., "Recyclable gold nanoparticle catalyst for the aerobic alcohol oxidation and C—C bond forming reaction between primary alcohols and ketones under ambient conditions", Tetrahedron, vol. 65, No. 7, Elsevier Ltd., Feb. 14, 2009, pp. 1461-1466.

Kwon, et al., "Recyclable Palladium Catalyst for Highly Selective α Alkylation of Ketones with Alcohols", Angewandte Chemie, vol. 44, Wiley-VCH Verlag GmbH & Co. KGaA, Weinheim, 2005, pp. 6913-6915.

International Preliminary Report on Patentability received for PCT Application No. PCT/US2012/035306, dated Dec. 12, 2013, 11 pages.

International Search Report and Written Opinion received for PCT Application No. PCT/US2012/035306, dated Feb. 13, 2013, 16 pages.

International Search Report and Written Opinion received for PCT Application No. PCT/US2014/035545 dated Nov. 24, 2014, 18 pages.

Roffler, et al., "Design and Mathematical Description of Differential Contactors Used in Extractive Fermentations", Biotechnology and Bioengineering, vol. 32, John Wiley & Sons, Inc., 1988, pp. 192-204.

Roffler, et al., "In Situ Extractive Fermentation of Acetone and Butanol", Biotechnology and Bioengineering, vol. 31, John Wiley & Sons, Inc., 1988, pp. 135-143.

Roffler, et al., "In-situ recovery of butanol during fermentation", Bioprocess Engineering, vol. 2, No. 1, Springer-Verlag, Mar. 1987, pp. 1-12.

Roffler, et al., "In-situ recovery of butanol during fermentation", Bioprocess Engineering, vol. 2, No. 4, Springer-Verlag, Dec. 1987, pp. 181-190.

Shimizu, et al., "Direct C—C Cross-Coupling of Secondary and Primary Alcohols Catalyzed by a y-Alumina-Supported Silver Subnanocluster", Angewandte Chemie International Edition,vol. 48 , 2009, pp. 3982-3986.

Yamada, et al., "A Solid-Phase Self-Organized Catalyst of Nanopalladium with Main-Chain Viologen Polymers: α-Alkylation of Ketones with Primary Alcohols", Organic Letters, vol. 8, No. 7, American Chemical Society, Mar. 2006, pp. 1375-1378.

Yamada, et al., "Development of a convoluted polymeric nanopalladium catalyst: α-alkylation of ketones and ring-opening alkylation of cyclic 1,3-diketones with primary alcohols", Tetrahedron, vol. 63, No. 35, Elsevier Ltd., Aug. 27, 2007, pp. 8492-8498.

Ekeley et al., "The Condensation Products of Diethyl Ketone", Journal of the American Chemical Society, vol. 46, Feb. 1924, pp. 447.

International Preliminary Report on Patentability received for PCT Application No. PCT/US2015/022086, dated Oct. 6, 2016, 9 pages.

International Preliminary Report on Patentability received for PCT Patent Application No. PCT/US2014/035545,dated Nov. 5, 2015, 13 pages.

International Search Report and Written Opinion received for PCT Patent Application No. PCT/US2015/022086, dated Sep. 29, 2015, 14 pages.

Invitation to Pay Additional Fee received for PCT Patent Application No. PCT/US2015/022086, dated Jul. 22, 2015, 4 pages.

Non-Final Office Action received for U.S. Appl. No. 14/123,064, dated Jan. 4, 2016, 10 pages.

Non-Final Office Action received for U.S. Appl. No. 14/123,064, dated Jul. 15, 2016, 10 pages.

Seebald et al., "Reaktionen an Aluminiumoxiden. 2. Mitt.: Umsetzungen Von Butan-2-on an Aluminiumoxid", Arch. Pharmaz., vol. 305, No. 10, 1972, pp. 785-793. (English Abstract Only).

Shuikin et al., "Activity of Copper- and Iron-Containing Catalysts in the Reaction of Isophorone with Ammonia and Hydrogen", Petroleum Chemistry, vol. 36, No. 2, 1996, 1 page.

Shimizu, Ken-ichi, et al, "Direct C—C Cross-Coupling of Secondary and Primary Alcohols 4 Catalyzed by a y-Aiumina-Supported Silver Subnanocluster", Angew. Chem.; vol. 121, pp. 4042-4046, 2009.

Non-Final Office Action received for U.S. Appl. No. 14/123,064, dated Jan. 31, 2017, 9 pages.

Goulas, K, et al. (2016). "Synergistic Effects in Bimetallic Palladium-Copper Catalysts Improve Selectivity in Oxygenate Coupling Reactions." J. Am. Chem. Soc. 138(21): 6805-6812.

* cited by examiner (A)

(B)

METHODS TO PRODUCE FUELS

CROSS-REFERENCE TO RELATED APPLICATIONS

This application is a U.S. national stage application of PCT/US2014/035545, filed internationally on Apr. 25, 2014, which claims priority to U.S. Provisional Patent Application No. 61/816,617, filed Apr. 26, 2013, which are incorporated herein by reference in their entireties.

FIELD

The present disclosure generally relates to the production of fuels, and more specifically, to the catalytic conversion of alcohols into hydrocarbon ketones suitable for use as components in fuels, such as gasoline, jet and diesel fuels. The alcohols used in the methods described herein may be a mixture of alcohols obtained from fermentation of biomass, including for example, fermentation to produce isopropanol-butanol-ethanol (IBE) or acetone-butanol-ethanol (ABE).

BACKGROUND

Producing fuels from renewable sources has become increasingly important as a means of reducing the production of greenhouse gases and of reducing the imports of petroleum. See L. D. Gomez, C. G. Steele-King, S. J. McQueen-Mason, New Phytologist, 178, 473-485, (2008). Lignocellulosic biomass is typically made up of cellulose, hemicellulose, and lignin. These biomass components are non-edible, carbohydrate-rich polymers that may serve as a renewable source of energy. They typically make up to at least 70% of the dry weight of biomass. As such, conversion of these non-edible biomass components into bio-fuels is of ongoing interest that can benefit the environment and reduce petroleum imports. See A. Demirbas, Energy Sources, Part B: Economics, Planning and Policy, 3(2) 177-185 (2008).

Currently, several approaches are available for converting biomass into fuels. For example, chemical processing routes may involve high temperature pyrolysis or biomass liquefaction; pyrolysis products (syngas) can be converted via Fischer-Tropsch chemistry to higher carbon number fuels. Biological routes typically first hydrolyze the polysaccharide content of biomass to monosaccharides using cellulase and hemicellulase enzymes. These monosaccharides are then microbially converted to fuels.

Early efforts to biologically produce fuels from biomass included the fermentation of both starch-derived and lignocellulosic-derived carbohydrates to bio-alcohols such as bio-ethanol and bio-butanol. See Blanch, H. W. and C. R. Wilke, Sugars and Chemicals from Cellulose, Reviews in Chemical Engineering, eds., N. E. Amundson and D. Luss, vol 1, 1 (1982). These natural biological routes to produce alcohols (e.g., ethanol and butanol) from carbohydrates typically yield low molecular weight compounds that are generally more suitable as gasoline additives than as jet and diesel fuels. While advances in metabolic engineering have enabled biological production of several higher molecular weight jet and diesel fuel compounds, these processes typically suffer from low titers and yields.

More recent efforts have focused on the carbohydrate source obtained from lignocellulosic biomass. Cellulose and hemicellulose obtained from lignocellulosic biomass after pre-treatment and hydrolysis affords hexoses and pentoses, respectively. Subsequent dehydration of these sugars into furfural and 5-hydroxymethylfurfural (HMF) may be achieved by chemical processes. Biological routes can ferment the hexoses and pentoses to short chain alcohols (e.g., ethanol and butanols) or to higher carbon number alkanes and alkenes, terpenes and fatty acids that can be esterified for use as diesel fuels.

While there are efficiencies of hexose and pentose conversion to short-chain alcohols, current microbial routes to higher carbon number products often have low yields and product titers. These products are currently not economically attractive as fungible fuels that can be employed as gasoline, jet and diesel fuel additives or replacements.

Thus, what is needed in the art is a commercially-viable process of producing fungible fuels, such as transportation fuels, and other chemicals from biomass, which allows for the control of product selectively. Moreover, what is needed in the art is a commercially-viable process for producing higher molecular weight fuel compounds and other chemicals from biomass.

BRIEF SUMMARY

In one aspect, provided is a method of producing a mixture of hydrocarbon ketones, comprising contacting at least two or more alcohols with metal catalyst and optionally base to produce a mixture of hydrocarbon ketones, wherein at least one of the two or more alcohols is a secondary alcohol. In some embodiments, the at least two or more alcohols are $C_1$-$C_{20}$ alcohols, and at least one of the two or more alcohols is a secondary $C_3$-$C_{20}$ alcohol. In some embodiments, the secondary alcohol is isopropanol, 2-butanol, 2-pentanol, 2-hexanol, 2-heptanol, 2-octanol, 2-nonanol, 2-decanol, 2-undecanol, 2-dodecanol, 2-tridecanol, 2-tetradecanol, 2-pentadecanol, 2-hexadecanol, 2-heptadecanol, 2-octadecanol, 2-nonadecanol, 2-icosanol, 2,3-butanediol, acetoin, or any combination thereof. In some embodiments, the two or more alcohols are two alcohols or three alcohols. In some embodiments, the two alcohols are isopropanol and n-butanol. In some embodiments, the three alcohols are isopropanol, n-butanol and ethanol. In some embodiments, the three alcohols are 2-butanol, n-butanol and ethanol.

In another aspect, provided is a method of producing a mixture of hydrocarbon ketones, comprising contacting a secondary alcohol and one or more primary alcohols with metal catalyst and optionally base to produce a mixture of hydrocarbon ketones. In some embodiments, the secondary alcohol is a $C_3$-$C_{20}$ alcohol. In some embodiments, the secondary alcohol is isopropanol, 2-butanol, 2-pentanol, 2-hexanol, 2-heptanol, 2-octanol, 2-nonanol, 2-decanol, 2-undecanol, 2-dodecanol, 2-tridecanol, 2-tetradecanol, 2-pentadecanol, 2-hexadecanol, 2-heptadecanol, 2-octadecanol, 2-nonadecanol, 2-icosanol, 2,3-butanediol, acetoin, or any combination thereof. In some embodiments, the one or more primary alcohols are $C_1$-$C_{20}$ alcohols. In some embodiments, the one or more primary alcohols are n-butanol, ethanol, or 2-ethyl-hexanol, or any combination thereof. In some embodiments, the secondary alcohol is isopropanol, and the one or more primary alcohols are butanol and ethanol. In some embodiments, the isopropanol and ethanol are provided in a ratio of about 2.3 to about 1. In some embodiments, the butanol is provided in stoichiometric excess of the isopropanol and ethanol. In some embodiments, the secondary alcohol is 2-butanol, and the one or more primary alcohols are n-butanol, ethanol, or any combination thereof. In some embodiments, contacting the secondary alcohol with the metal catalyst and optionally the base oxidizes the secondary alcohol to produce a ketone. In some embodiments, at least a portion of the mixture of hydrocarbon ketones are produced from double alkylation of the ketone. In some embodiments, at least 70% of the mixture of hydrocarbon ketones are produced from double alkylation of the ketone.

In another aspect, provided is a method of producing a mixture of hydrocarbon ketones, comprising: a) contacting biomass or sugars with a fermentation host to produce a fermentation product mixture, wherein the fermentation product mixture comprises isopropanol, butanol and ethanol; b) isolating at least a portion of the isopropanol, butanol and ethanol from the fermentation product mixture; and c) contacting the isolated isopropanol, butanol and ethanol with metal catalyst and optionally base to produce a mixture of hydrocarbon ketones. In some embodiments, at least 70% of the mixture of hydrocarbon ketones are $C_{7+}$ hydrocarbon ketones. In some embodiments, at least 40% of the mixture of hydrocarbon ketones are $C_{11+}$ hydrocarbon ketones.

In another aspect, provided is a method of producing a mixture of hydrocarbon ketones, comprising: a) contacting biomass or sugars with a fermentation host to produce a fermentation product mixture, wherein the fermentation product mixture comprises acetone, butanol and ethanol; b) isolating at least a portion of the acetone, butanol and ethanol from the fermentation product mixture; and c) contacting the isolated acetone, butanol and ethanol with metal catalyst and optionally base to produce a mixture of hydrocarbon ketones, wherein at least 20% of the mixture of hydrocarbon ketones are $C_{7+}$ hydrocarbon ketones. In some embodiments, at least 70% of the mixture of hydrocarbon ketones are $C_{7+}$ hydrocarbon ketones. In some embodiments, at least 40% of the mixture of hydrocarbon ketones are $C_{11+}$ hydrocarbon ketones.

In yet another aspect, provided is a method of producing a mixture of hydrocarbon ketones, comprising contacting acetone and at least two or more primary alcohols with catalyst and optionally base to produce a mixture of hydrocarbon ketones. In some embodiments, the catalyst comprises hydrotalcite (HT) and one or more metals. In certain embodiments, the catalyst comprises two or more metals impregnated on hydrotalcite. In some embodiments, the catalyst comprises $La_2O_3$ and one or more metals. In certain embodiments, wherein the catalyst comprises one or more metals impregnated on $La_2O_3$. In some embodiments, the catalyst comprises MgO and one or more metals. In certain embodiments, the catalyst comprises one or metals are impregnated on MgO. In one embodiment that may be combined with any of the foregoing embodiments, the catalyst further comprises $TiO_2$.

In other embodiments, the catalyst comprises $TiO_2$ and one or more metals. In certain embodiments, the catalyst comprises one or more metals impregnated on $TiO_2$. In certain embodiments, the $TiO_2$ is impregnated on carbon support. In other embodiments, the catalyst comprises MgO and one or more metals. In certain embodiments, the catalyst comprises one or more metals impregnated on MgO. In certain embodiments, the MgO is impregnated on carbon support.

In yet other embodiments, the catalyst comprises Pd—Cu/HT, Pd—Cu/HT-C, Pd—Cu/HT/C, Pd/HT, Cu/HT, Cu/ZnO/$Al_2O_3$, hydroxyapatite, perovskite, Cu/MgO, (Cu/ZnO/$Al_2O_3$)/HT, $BaO/SiO_2$, $MgO/SiO_2$, $SrO/SiO_2$, $CaO/SiO_2$, SrO/MgO, CaO/MgO, Pd—Cu/NiHT, Cu/NiHT, PdCu/ZnHT, Cu/ZnHT, PdCu/ZnHT, Ru/HT, Cu—Ru/HT, Co/HT, Pt/HT, Pt—Cu/HT, Cu/$SiO_2$, Pd/C, CaO/C, SrO/C, BaO/C, $La_2O_3$/C, $CeO_2$/C, HT/C, HT, $CeO_2$, $La_2O_3$, $TiO_2$, or zeolite, or any combinations thereof.

Provided are one or more hydrocarbon ketones, or a mixture of hydrocarbon ketones, produced according to any of the methods described herein.

Provided is also a composition that includes (a) a gasoline fuel, a jet fuel, a diesel fuel, or any mixtures thereof; and (b) one or more hydrocarbon ketones, or a mixture of hydrocarbon ketones, produced according to any of the methods described herein.

DESCRIPTION OF THE FIGURES

The present application can be understood by reference to the following description taken in conjunction with the accompanying drawing figures, in which like parts may be referred to by like numerals.

DETAILED DESCRIPTION

Figure 1:
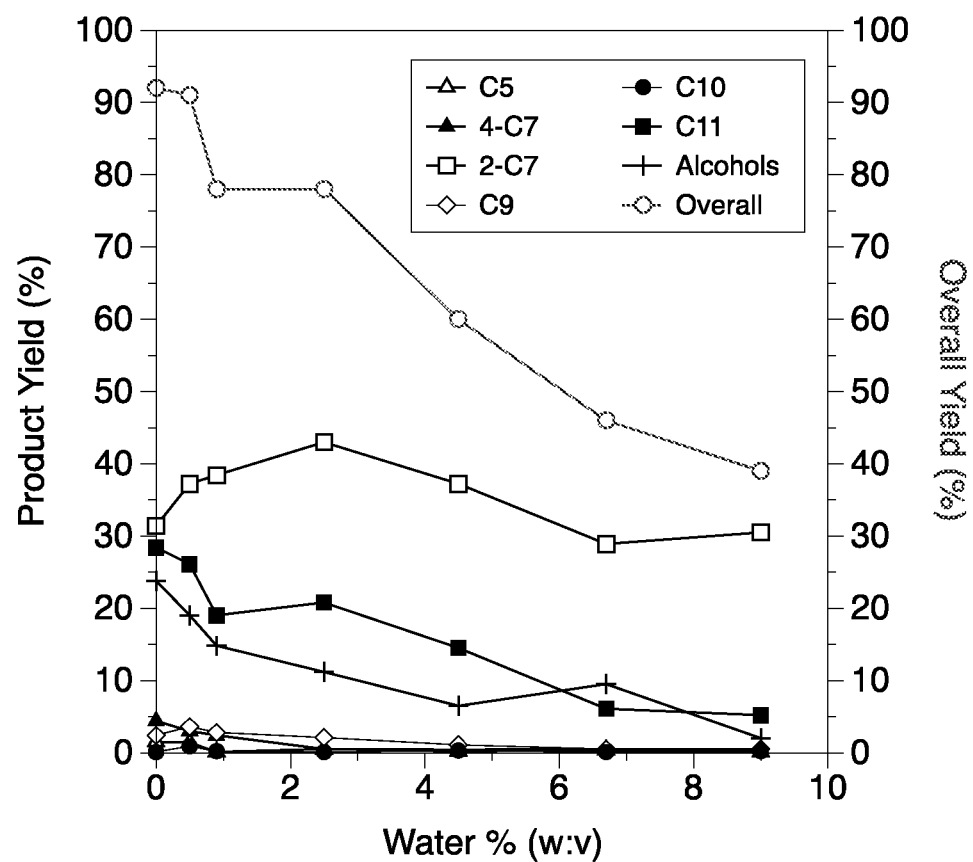
FIG. 1 is a graph depicting the effect of water on the product and overall yields of various alkanones produced in an ABE reaction.

The following description sets forth numerous exemplary configurations, processes, parameters, and the like. It should be recognized, however, that such description is not intended as a limitation on the scope of the present disclosure, but is instead provided as a description of exemplary embodiments.

Provided herein are methods of producing compounds suitable for use as components of fuels (e.g., gasoline, jet, and diesel fuels) from a mixture of alcohols and/or ketones.

Such alcohols and/or ketones may be obtained from any commercially available sources, as well as any methods known to one of skill in the art. For example, isopropanol-butanol-ethanol (IBE) fermentation can yield a mixture of alcohols suitable for use in the methods described herein. Similarly, acetone-butanol-ethanol (ABE) fermentation can yield a mixture of ketone and alcohols suitable for use in the methods described herein. See FIG. 1.

When a mixture of alcohols is provided, at least one of the alcohols is a secondary alcohol or an alcohol with at least one secondary alcohol moiety, which can be oxidized to a ketone in situ and subsequently alkylated by the metal catalyst and optionally base with other alcohols present in the reaction mixture. For example, the mixture of alcohols may include a secondary alcohol such as isopropanol, which can be oxidized to acetone and subsequently alkylated to produce a mixture of hydrocarbon ketones. Alternatively, a ketone, such as acetone, can directly be provided for reaction with one or more alcohols.

The fuel components prepared according to the methods provided herein include hydrocarbon ketones.

In one aspect, provided is a method of producing a mixture of hydrocarbon ketones, by contacting at least two or more alcohols, wherein at least one of the two or more alcohols is a secondary alcohol, with metal catalyst and optionally base, to produce a mixture of hydrocarbon ketones. Such hydrocarbon ketones can be further processed to produce suitable alcohols and/or alkanes for use as fuels and other products.

In another aspect, provided herein are integrated methods to produce a mixture of hydrocarbon ketones, by: a) contacting biomass or sugars with a fermentation host to produce a fermentation product mixture, wherein the fermentation product mixture comprises either isopropanol, butanol and ethanol (IBE) or acetone, butanol and ethanol (ABE); b) isolating at least a portion of the IBE or ABE from the fermentation product mixture; c) contacting the isolated IBE or ABE with metal catalyst and optionally base to produce a mixture of hydrocarbon ketones.

The various methods to produce the mixture of hydrocarbon ketones suitable for use as components in fuel (e.g., gasoline, jet and diesel) are described in further detail below. The choice of the starting materials used and the reaction conditions selected can tune the mix of hydrocarbon ketones produced. The reaction conditions can be selected to allow for greater kinetic control of the alkylation reaction to preferentially produce hydrocarbon ketones more suitable for use as components in jet and diesel fuel (e.g., $C_5$-$C_{20+}$ alkanones or $C_{11+}$ alkanones, respectively).

Mixtures of Alcohols and/or Ketones as Starting Materials

A mixture of hydrocarbon ketones can be produced according to the methods described herein by contacting at least two or more alcohols with metal catalyst and optionally base. In some embodiments, at least one of the two or more alcohols has a secondary alcohol moiety. In certain embodiments, the method involves contacting at least one secondary alcohol (e.g., R'R"—CH—OH) and at least one primary alcohol (e.g., R'—CH$_2$—OH) with metal catalyst and optionally base. In one embodiment, the method involves contacting one secondary alcohol and at least one primary alcohol with metal catalyst and optionally base. Suitable primary alcohols may include, for example, ethanol, n-propanol, n-butanol, or 2-methylpropan-1-ol. Suitable secondary alcohols may include, for example, isopropanol, 2-butanol, and 2-pentanol. In preferred embodiments, the secondary alcohols disclosed herein contain at least one terminal methyl group.

It should be further understood that, in some embodiments, one or more of the alcohols used herein may include one or more —OH groups. In some embodiments, at least one of the alcohols has a structure of formula (A):

wherein n is 0 or 1 or 2 and R is CH$_3$ or H. In some embodiments, at least one of the alcohols is isopropanol, 2,3-butanediol, glycerol, or any mixture thereof. In certain embodiments, at least one of the —OH groups is bonded to the carbon atom adjacent to a terminal methyl group.

One or more of the alcohols used in the methods described herein may independently be linear or branched. In some embodiments, all linear alcohols may be used. For example, in one embodiment, a mixture of isopropanol, n-butanol and ethanol may be used. In other embodiments, all branched alcohols may be used. In yet other embodiments, a mixture of linear and branched alcohols may be used.

Additionally, one or more of the alcohols used in the methods described herein may be optionally substituted. In some embodiments, one or more of the alcohols may be substituted with 1 to 5 substituents, 1 to 4 substituents, 1 to 3 substituents, 1 to 2 substituents, or 1 substituent. Suitable substituents may include, for example, alkyl, cycloalkyl, aryl, heteroaryl, alkenyl, alkynyl, oxo, —OH, or esters. In some embodiments, any substituent that is not destroyed by base/reduction is contemplated (e.g., aryl or heteroaryl). In other embodiments, any substituent that may be hydrolyzed (e.g., esters) or reduced (e.g., alkenyl or alkynyl) is contemplated. In some embodiments, one or more of the alcohols are unsubstituted. In other embodiments, one or more of the alcohols are substituted. In yet other embodiments, a mixture of unsubstituted and substituted alcohols may be used. For example, in one embodiment, a mixture of acetoin, n-butanol and ethanol may be used.

In some embodiments, the alcohols used herein may contain a primary alcohol moiety (e.g., —R'—CH$_2$—OH), a secondary alcohol moiety (e.g., —R'R"—CH—OH), or a combination thereof.

Various mixtures of alcohols may be used in the methods described herein. In some embodiments, the alcohols are $C_1$-$C_{20}$ alcohols, $C_2$-$C_{10}$ alcohols, $C_2$-$C_8$ alcohols, $C_2$-$C_6$ alcohols, $C_2$-$C_4$ alcohols. In one embodiment, the alcohols may include isopropanol and butanol. In another embodiment, the alcohols may include isopropanol and ethanol. In yet another embodiment, the alcohols may include isopropanol, butanol, and ethanol. In certain embodiments, the alcohols may include 2-butanol and n-butanol.

In some embodiments, the secondary alcohol is a $C_3$-$C_{20}$ alcohol. In some embodiments, the secondary alcohol is isopropanol, 2-butanol, or a combination thereof. In preferred embodiments, the secondary alcohols disclosed herein contain at least one terminal methyl group.

In some embodiments, the one or more primary alcohols are independently $C_1$-$C_{20}$ alcohols, $C_2$-$C_{10}$ alcohols, $C_2$-$C_8$ alcohols, $C_2$-$C_6$ alcohols, or $C_2$-$C_4$ alcohols. In some embodiments, the one or more primary alcohols are n-butanol, ethanol, or 2-ethyl-hexanol, or any combination thereof.

In some embodiments, the secondary alcohol is isopropanol, and the one or more primary alcohols are butanol and ethanol. In some embodiments, the isopropanol and ethanol are provided in a ratio of about 2.3 to about 1. In some embodiments, the butanol is provided in stoichiometric excess of the isopropanol and ethanol. In some embodiments, the secondary alcohol is 2-butanol, and the one or more primary alcohols are n-butanol, ethanol, or any combination thereof.

The metal catalyst (including, for example, metal catalysts having a basic support) and optionally in combination with base may oxidize the alcohol having at least one secondary alcohol moiety or the secondary alcohol to produce a ketone. Once the ketone is formed, the metal catalyst and optional base further promote alkylation of the ketone with one or more of the other alcohols present in the reaction mixture.

Provided herein are also methods to produce hydrocarbon ketones involving the use of at least one ketone starting material with one or more alcohols. The use of a ketone starting material can replace the use of an alcohol having at least one secondary alcohol moiety or a secondary alcohol, which can convert to a ketone in situ. It should be understood that all of the catalysts, bases, and reaction conditions described herein may apply to reactions involving a mixture of alcohols as starting materials (e.g., IBE), as well as to reactions involving a mixture of ketone(s) and alcohols as starting materials (e.g., ABE). In preferred embodiments, the ketone starting material disclosed herein contains at least one terminal methyl group.

It should be understood that the alcohols and/or ketones provided for use in the methods described herein may be obtained from any commercially available sources, or accordingly to any methods generally known by one of skill in the art. In some embodiments, the alcohols and/or ketones are produced from biological processes, such as by fermentation.

In some embodiments, an isopropanol-butanol-ethanol (IBE) mixture is used as the alcohol starting materials in the reaction to produce hydrocarbon ketones. In situ formation of acetone in lower concentration via dehydrogenation of isopropanol during the IBE alkylation reaction was observed to unexpectedly favor the aldol condensation with 2-ethyl hexanal formed from the Guerbet reaction of butanol, thereby increasing the concentration of $C_{11+}$ compounds in the mixture of hydrocarbon ketones compared to a process where acetone is used directly (e.g., acetone-butanol-ethanol or ABE starting materials). $C_{11+}$ compounds may be useful for the production of jet and diesel fuels, which generally contain higher hydrocarbon components than gasoline.

In other embodiments, an acetone-butanol-ethanol (ABE) mixture is used as the ketone-alcohol starting materials in the reaction to produce hydrocarbon ketones.

In some embodiments, the IBE or ABE feedstocks may be enriched in butanol and 2-ethylhexanol by reacting ethanol and butanol in a Guerbet reactor prior to feeding the materials to the main alkylation reactor. Also 2-ethylhexanol that is produced in the Guerbet reactor may also be used in the synthesis of $C_{11+}$ compounds. It should be understood that, in other exemplary embodiments, the Guerbet reactor may be the first portion of the main aldol condensation reactor (e.g., one reactor with multiple feed inlets).

The sources for the IBE and ABE mixtures that may be used are described in further detail below.

Fermentation Product Mixture

The fermentation product mixture described herein may be derived from renewable sources, such as biomass. In some embodiments, the biomass is first converted into sugars, which is then used as the feedstock to produce the fermentation product mixture. Sugars suitable for use as feedstock to produce the fermentation product mixture may include, for example, monosaccharides, disaccharides, or oligosaccharides. In certain embodiments, the sugars may include any $C_5$ saccharides or $C_6$ saccharides, or a combination of $C_5$ and $C_6$ saccharides. In other embodiments, the sugars may include arabinose, lyxose, ribose, xylose, ribulose, xylulose, allose, altrose, glucose, sucrose, cellobiose, mannose, gulose, idose, galactose, talose, psicose, fructose, sorbose, tagatose, xylobiose, glucose oligomers, xylose oligomers, or a mixture thereof. In one embodiment, the sugars may include glucose, sucrose or xylose, or a mixture thereof. In another embodiment, the sugars may include glucose or sucrose, or a mixture thereof. Any methods known in the art may be employed to produce sugars from the biomass. For example, the biomass may undergo pretreatment processes known in the art to more effectively liberate sugars from the biomass. The biomass is typically made up of organic compounds that are relatively high in oxygen, such as carbohydrates, and may also contain a wide variety of other organic compounds. In some embodiments, the biomass is made up of cellulose, hemicellulose, and/or lignin. Other suitable carbon sources for fermentation may include, for example, pectin, whey, butyric and acetic acids.

It should be understood, however, that in other embodiments, the sugars used as feedstock in the fermentation process may be derived from non-renewable sources, or from both renewable and non-renewable sources.

Isopropanol-Butanol-Ethanol (IBE) Fermentation Product Mixture

In some embodiments, the fermentation product mixture may include one or more alcohols. The fermentation product mixture may be an IBE mixture produced by fermenting sugars using any host capable of producing hydrocarbons (e.g., ethanol and heavier hydrocarbons). Suitable carbon sources for IBE fermentation may include, for example, glucose, xylose, sucrose, cellobiose, pectin, whey, butyric acid, or acetic acid.

For example in some embodiments, the fermentation host is bacteria from the Clostridia family (e.g., *Clostridium acetobutylicum, Clostridium beijerinckii*). Clostridia bacteria have the ability to convert biomass-derived carbohydrates into an IBE mixture from both hexoses and pentoses. IBE may be produced from a biological source. It was recently reported that *C. acetobutylicum* would produce IBE by expression of the secondary alcohol dehydrogenase (SADH) from *Clostridium beijerinckii* strain B593. Lee, J., et al. *Appl. Environ. Microbiol.* 2012, 78, 1416. It should be understood, however, that any fermentation host capable of converting sugars into a mixture of one or more alcohols may be employed to provide the starting materials for the process described herein.

In some embodiments, the fermentation product mixture may be used without further purification or isolation steps after the fermentation process. In other embodiments, the fermentation product mixture is isolated after the fermentation process. Any techniques known in the art may be used to isolate the fermentation product mixture (e.g., IBE mixture) after the fermentation process.

While an IBE mixture may be used as the starting materials, the starting materials used in the processes described herein are not limited to isopropanol, butanol, and ethanol as the alcohols. The alcohols may be any length. In some embodiments, the fermentation product mixture may include other alcohols including, for example, methanol, propanol, 2-methylpropan-1-ol, pentanol, and 2-ethyl-1-hexanol.

Additional alcohols may be added to the fermentation product mixture to vary the range of molecular weights and structures obtained from the process described herein. In some embodiments, these additional alcohols may be added to the fermentation product mixture before use in the reaction with the catalyst. In other embodiments, these additional alcohols may be added during the reaction. These additions to the fermentation product mixture may be useful for improving the product properties for specific applications, such as biodiesel. The alcohols added to the fermentation product mixture may be saturated or unsaturated.

Acetone-Butanol-Ethanol (ABE) Fermentation Product Mixture

In some embodiments, the fermentation product mixture may include a ketone and one or more alcohols. In certain embodiments, the fermentation product mixture may include a ketone and one alcohol, or a ketone and two alcohols. In certain embodiments, the ketone is acetone. In certain embodiments, the one or more alcohols may be one or more primary alcohols. In one embodiment, the one or more alcohols may be one or more $C_1$-$C_{20}$, $C_1$-$C_{15}$, $C_1$-$C_{10}$ or $C_1$-$C_8$ primary alcohols. The fermentation product mixture may be an ABE mixture produced by fermenting sugars using any host capable of producing hydrocarbons (e.g., ethanol and heavier hydrocarbons). For example in some embodiments, the fermentation host is bacteria from the Clostridia family (e.g., *Clostridium acetobutylicum, Clostridium beijerinckii*). Clostridia bacteria have the ability to convert biomass-derived carbohydrates into an ABE mixture from both hexoses and pentoses. It should be understood, however, that any fermentation host capable of converting sugars into a mixture of a ketone and one or more alcohols may be employed to provide the starting materials for the process described herein.

In some embodiments, the fermentation product mixture may be used without further purification or isolation steps after the fermentation process. In other embodiments, the fermentation product mixture is isolated after the fermentation process. Any techniques known in the art may be used to isolate the fermentation product mixture (e.g., ABE mixture) after the fermentation process.

While an ABE mixture may be used as starting materials, the starting materials used in the process described herein are not limited to butanol and ethanol as the alcohols. The alcohols may be any length. In some embodiments, the fermentation product mixture may include primary alcohols including, for example, methanol, ethanol, propanol, 2-methylpropan-1-ol, butanol, pentanol, and 2-ethyl-1-hexanol.

In some embodiments, the ABE mixture has a mass ratio of about 3 to about 6 to about 1, but the ratio of acetone to the two or more primary alcohols may vary. For example, the fermentation process may be optimized to reduce the amount of ethanol produced, so as to maximize butanol yields.

Additional ketones and alcohols may be added to the fermentation product mixture to vary the range of molecular weights and structures obtained from the process described herein. In some embodiments, these additional ketones and alcohols may be added to the fermentation product mixture before use in the reaction with the catalyst. In other embodiments, these additional ketones and alcohols may be added during the reaction. These additions to the fermentation product mixture may be useful for improving the product properties for specific applications, such as biodiesel. The alcohols and ketones added to the fermentation product mixture may be saturated or unsaturated.

The fermentation product mixture may also include bio-derived ketones through ketonization of volatile fatty acids. For example, acetic acid may be ketonized via fermentation to form acetone, which can be converted into a mix of higher ketones using the methods described herein to produce gasoline and gasoline precursors. Propionic acid may also be ketonized via fermentation to form 3-pentanone, which can be converted into a mix of higher ketones using the methods described herein to produce gasoline and gasoline precursors.

Extraction of Fermentation Product Mixture

Further, in some embodiments, an extractant may be used to selectively isolate the fermentation product mixture from the aqueous phase into an organic (water immiscible) phase. An extractant is a chemical used to recover certain products from the fermentation broth. In one example, an extractant may be used to recover isopropanol, butanol, and ethanol from the fermentation broth. In another example, an extractant may be used to recover isopropanol and butanol from the fermentation broth. In another example, an extractant may be used to recover acetone, butanol, and ethanol from the fermentation broth. In another example, an extractant may be used to recover acetone and butanol from the fermentation broth.

Suitable extractants may include tributyrin (also known as glyceryl tributyrate), oleyl alcohol, polypropylene glycol (of varying molecular weights), or mixtures of these extractants. In some embodiments, the extractant does not inhibit the growth of the microorganism producing the fermentation product mixture, or decrease the rate of formation of the fermentation products. In certain embodiments, the extractant can be chosen from a class of materials that are (a) not inhibitory to microorganisms (b) have very low solubility in water, and (c) have very low water solubility, referring to the amount of water that can be dissolved in the extractant.

In certain embodiments, in situ extraction may be conducted during the fermentation, and can reduce the inhibitory effect of some of products generated from the fermentation process. For example, the fermentation process described above may yield metabolites, which have inherent toxicity that may affect the catalysis of the alkylation reaction under aqueous conditions. The use of a selective, non-toxic, water-immiscible extractant can remove in situ inhibitory metabolites produced during fermentation. Removal of such inhibitory products can increase solvent titers and yields, lower distillation costs, and reduce water usage and reactor sizes. When used during fermentation, the extractant employed should be non-inhibitory. However, in other embodiments, the extractant may be toxic if used in a process where the cells are removed prior to exposure to the extractant.

In other embodiments, an extractant may be used on the fermentation product mixture after fermentation has taken place to selectively extract certain components of the fermentation product mixture from the aqueous phase into the organic phase. For example, in one embodiment, an extractant such as tributyrin may be used on the fermentation product mixture to relative amounts of acetone and butanol in the fermentation product mixture used in the alkylation reactions described herein. Such fermentation products can be recovered from the extractant by distillation. When the boiling points of the extractants employed are much higher than those of the fermentation products, the energy requirements for distillation can be reduced. Since the extractants have very little solubility for water, almost no water is present in the extractant, leaving primarily the fermentation products.

Thus, in some embodiments, an extractant can selectively separate acetone, butanol, and ethanol from an ABE mixture in ratios suitable for subsequent alkylation reactions to yield fuel products. In some embodiments, an extractant can selectively separate acetone and butanol from an ABE mixture in ratios suitable for subsequent alkylation reactions to yield fuel products, and minimize the amount of ethanol extracted. In some embodiments, minimizing the amount of ethanol in the ABE mixture undergoing alkylation may, in some instances, be desirable for controlling the molecular weight of the products, such as for producing longer chained products. The addition of an extractant to the fermentation culture may, in certain embodiments, reduce the formation the Guerbet product. In certain embodiments, the addition of an extractant to the fermentation culture produces at least 40%, 50%, 60%, 70%, 80% or 90% double-alkylated products. In some preferred embodiments, the extractant is glyceryl tributyrate.

In other embodiments, an extractant can selectively separate isopropanol, butanol, and ethanol from an IBE mixture in ratios suitable for subsequent alkylation reactions to yield fuel products. In some preferred embodiments, the extractant is oleyl alcohol.

The use of an extractant, in certain embodiments, affords simultaneous removal of residual inhibitors and the desired product during biofuel fermentation, a key advantage over existing recovery technologies Inhibitors that may be removed using an extractant include, for example, furfural, vanillin, syringaldehyde, p-coumaric acid, and ferulic acid. Removal of these inhibitors can enhance fermentation titer, productivities, and yields for the production of fermentation products, including IBE or ABE.

Other techniques known in the art may be used to selectively separate ketones and alcohols from a fermentation mixture (e.g., acetone, butanol, and ethanol from an ABE mixture) or alcohols from a fermentation mixture (e.g., isopropanol, butanol, and ethanol from an IBE mixture) for subsequent alkylation reactions to yield fuel products. For example, pervaporation is a membrane separation technique that can be utilized to separate liquid mixtures through a membrane via a solution-diffusion mechanism. First, permeation through the membrane takes place, and then the permeate is collected as a vapor on the other side of the membrane. The evaporation of the permeate on the permeate side of the membrane creates the driving force for the transfer of the permeate. The pervaporation membrane behaves as a selective barrier between the feed and the permeate; therefore, the selection of the pervaporation membrane is crucial to achieve high selectivity and fluxes. The permeability of the components through the membrane is the multiplication of their diffusion and solubility in the membrane material. For instance, for pervaporation of alcohol-water mixtures, the diffusivity of water is greater than the diffusivity of the alcohol due to the smaller dimension of the water molecule. Therefore, a membrane material with higher alcohol solubility should be selected to obtain high alcohol permselectivity. Polydimethylsiloxane (PDMS) is well known as a membrane material for ethanol separation from dilute aqueous ethanol mixture due to its hydrophobic nature and high free volume which allows excellent selectivity and high fluxes. Pervaporation is one exemplary separation technique. Other separation techniques known in the art may be employed.

Pervaporation may also be used to separate the ketones and alcohols from the extraction solvent (e.g., acetone and butanol from an extracted ABE mixture) or alcohols from the extraction solvent (e.g., isopropanol, butanol, and ethanol from an extracted IBE mixture). Pervaporation is one exemplary separation technique. Other separation techniques known in the art may be employed.

Thus, in some embodiments, the methods described herein further include providing a pervaporation membrane, and contacting the fermentation product mixture with the pervaporation membrane to selectively separate ketones and alcohols from a fermentation mixture (e.g., acetone and butanol from an ABE mixture) or alcohols from a fermentation mixture (e.g., isopropanol, butanol, and ethanol from an IBE mixture). In one embodiment, the pervaporation membrane is PDMS. In another embodiment, the pervaporation membrane is a poly(styrene-b-dialkylsiloxane-b-styrene) triblock copolymer that has a polydialkylsiloxane block and polystyrene end blocks. In certain embodiments, the triblock copolymer has a molecular weight in the range of about 110 kg/mol to about 1000 kg/mol. In other embodiments, the triblock copolymer has a molecular weight in the range of about 110 kg/mol to about 500 kg/mol. In some embodiments, the triblock copolymer has a molecular weight in the range of about 120 kg/mol to about 300 kg/mol. In some embodiments, the triblock copolymer has a molecular weight in the range of about 130 kg/mol to about 300 kg/mol. In some embodiments, the triblock copolymer has a morphology, and wherein the morphology is a cylindrical, lamellar, double diamond, or gyroid morphology. In some embodiments, the triblock copolymer has a morphology, and wherein the morphology is a cylindrical or lamellar morphology. In some embodiments, the triblock copolymer has a morphology, and wherein the morphology is a cylindrical morphology. In some embodiments, the triblock copolymer has a domain spacing (d), and wherein the domain spacing is in the range of about 20 to about 90 nanometers. In some embodiments, the triblock copolymer loses about 5% of weight at a temperature in the range of about 290° C. to about 350° C. In some embodiments, the polydialkylsiloxane is polydimethylsiloxane. In some embodiments, the polydialkylsiloxane block has a volume fraction of about 0.6 to about 0.95 relative to the polystyrene end blocks.

The Metal Catalyst

Certain metal catalyst that can catalyze the alkylation of a ketone (e.g., that is formed in situ in the reaction or provided to the reaction) may be employed in the methods described herein. For example, in one embodiment, any metal catalyst that can catalyze the alkylation or the double alkylation of a ketone, such as acetone, may be employed in the methods described herein. The metal catalyst can also be selected to catalyze the in situ formation of a ketone from a secondary alcohol (e.g., acetone from isopropanol).

In some embodiments, the metal catalyst includes a transition metal. In some embodiments, the metal-based catalyst includes a late transition metal. In some embodiments, the metal catalyst includes a metal selected from the group consisting of ruthenium, iron, palladium, platinum, cobalt, and copper. Mixtures of these metals are also contemplated, including for example metal alloys. In some embodiments, the ruthenium, iron, palladium, platinum, cobalt, and copper, either used alone or in combination, may also be combined with other metals such as lanthanides. In some preferred embodiments, the metal is selected from the group consisting of ruthenium, palladium, and copper. In other preferred embodiments, the metal is palladium or copper. In some preferred embodiments, the metal is copper.

In other embodiments, the metal catalyst may include transition metals such as nickel, ruthenium, rhodium, palladium, rhenium, iridium, or platinum. In other embodiments, the metal catalyst includes palladium or platinum. In certain embodiments, the metal catalyst is [Ir(COD)Cl]$_2$, RuCl$_2$(COD), PtCl$_2$(COD), [Rh(COD)Cl]$_2$, Ni/Si-Alumina, Ru/C, Rh/C, Pt/C, or Pd/C.

In some embodiments, the metal catalyst is a single component metal oxides alkaline earth oxides such as alkali metal oxides rare earth oxides (e.g., ThO$_2$, ZrO$_2$, ZnO, and TiO$_2$).

In yet other embodiments, the metal catalyst is a palladium-based catalyst. Palladium-based catalysts may include palladium metal, and complexes of suitable ligands including those containing P and/or N atoms for coordinating to the palladium atoms, and other simple palladium salts either in the presence or absence of ligands. Palladium-based catalysts may also include palladium and palladium complexes supported or tethered on solid supports, such as palladium on carbon (Pd/C), as well as palladium black, palladium clusters, or palladium clusters containing other metals. Suitable examples of palladium-based catalysts may include Pd(OAc)$_2$, Pd$_2$(dba)$_3$, Pd(OH)$_2$/C, Pd/C, Pd/CaCO$_3$, Pd/Alumina, and Pd-polyethylenimines on silica.

In some embodiments, a combination of one or metals may be used, such as metal alloys. In some embodiments, the combination of one or metals is Pd and Cu. In some embodiments, the metal catalyst contains Pd/Cu, in which Pd is present in molar excess of Cu. In other embodiments, the metal catalyst contains Pd/Cu, in which Cu is present in molar excess of Pd. In yet other embodiments, the metal catalyst contains Pd/Cu at a molar ratio of between 10:1 and 1:10. In one embodiment, the metal catalyst contains Pd/Cu at a molar ratio of 1:1, 2:1, 3:1, 4:1, 5:1, 1:2, 1:3, 1:4, or 1:5. In a certain embodiment, the metal catalyst contains Pd/Cu at a 2:1 molar ratio.

The metal catalyst may be recycled in the methods described herein. For example, additional fermentation product mixture (e.g., ABE or IBE mixture) may be added to the reaction vessel to further increase the overall product yield.

Catalyst Support

In some embodiments, the metal catalyst may be a solid-supported metal catalyst. A solid-supported metal catalyst used herein typically is metal catalyst where the metal is deposited or impregnated onto a support.

In some embodiments, the support is selected from the group consisting of hydrotalcite, single component metal oxides, alkaline earth oxides, alkali metal oxides, rare earth oxides, ThO$_2$, MgO, Na doped MgO, SrO, BaO, CaO, ZnO, La$_2$O$_3$, TiO$_2$, ZrO$_2$, Al$_2$O$_3$, hydroxyapatite, fluorapatite, tert-butoxyapatite, sepiolite, basic zeolites, alkali ion-exchanged zeolites, alkali ion-added zeolites, Pd/NaY zeolite, Pd/NH$_4$-β zeolite, supported alkali metal ions, alkali metal ions on alumina, alkali metal ions on silica, alkali metal on alkaline earth oxide, alkali metals and alkali metal hydroxides on alumina, Metal/SiO$_2$, Na/SiO$_2$ Pd/Na/SiO$_2$, Na/Ca/SiO$_2$, Na/Ca/SiO$_2$, Cs/SiO$_2$, metal-supported zeolite, potassium oxide supported on zeolite Y, synthetic chrysotiles, Mg$_3$(OH)$_4$Si$_4$O$_5$, cobalt(II)-substituted chrysotile, amino-functionalized mesoporous silica, amino-functionalized MCM-41, alkali ion-exchanged mesoporous silica, alkali ion-exchanged SBA-15, ionic liquid supported MgO, amorphous aluminophosphate, synthetic talcs, magnesium organo silicates, KF supported on alumina, lanthanide imide on zeolite, and lanthanide nitride on zeolite. In some embodiments, the support is an alkali exchanged zeolite such as NaY, KY, RbY, CsY, NaX, KX, RbX, and CsX. In some embodiments a metal such as Pd or Cu is deposited on the alkali exchanged zeolite and used as the metal based catalyst such as, for example, Pd/CsY and Cu/CsY. In some embodiments, alkali metal ions are added to the support (e.g., alkali metal ions on alumina, alkali metal ions on silica, alkali metal on alkaline earth oxide, alkali metals and alkali metal hydroxides on alumina)

In some preferred embodiments, the support is a hydrotalcite. In some embodiments, the hydrotalcite comprises one or more metals selected from the group consisting of magnesium, aluminum, lithium, zinc, copper, and nickel. In other embodiments, the one or more metals are selected from the group consisting of palladium, copper, nickel, zinc, ruthenium, cobalt, and platinum. In some embodiments, the hydrotalcite is selected from the group consisting of Mg—Al, Li—Al, Zn—Al, Cu—Zn—Al, and Ni—Mg—Al hydrotalcite. Basicity of hydrotalcites can be tuned by varying the magnesium-aluminum ratio, by rehydrating calcined hydrotalcite, and doping hydrotalcite with Na and K. In some embodiments, hydrotalcites are prepared by co-precipitation of alkaline earth metal salts and/or aluminum nitrates in a solution that includes urea or ammonia and ammonium carbonate or potassium hydroxide and potassium carbonate or sodium hydroxide and sodium carbonate. In some embodiments, alkaline earth metal supports might be prepared by decomposition of nitrate, carbonate or dicarboxylic acid salts at elevated temperatures, from 450° C. to 900° C.

Basic Catalysts

In some embodiments, the catalysts include one or more metals, and a basic support.

Catalyst basicity may be measured by a variety of techniques known to one of skill in the art. For example, basicity of the catalyst can be measured by $CO_2$ temperature-programmed desorption (TPD). In some embodiments, the $CO_2$ TPD is carried out by adsorbing $CO_2$ to the catalyst at room temperature and heating up to 773 K (or similar assay). In some embodiments, for non-zeolite catalysts, preferred catalysts have base site densities measured by $CO_2$ TPD of at least 50 micromoles/gram of catalyst. In other embodiments, for zeolite catalysts, preferred catalysts have base site densities by $CO_2$ TPD of at least 10 micromoles/gram of catalyst. In other embodiments, all preferred catalysts of all types have base site densities by $CO_2$ TPD of at least 10 micromoles/gram of catalyst.

Basicity of the catalyst may also be measured using zero charge determination (Regalbuto), or using the Hammett indicator method.

In some embodiments, the metal catalysts have a pKa from 10 to 16. In other embodiments, the metal catalysts have a pKa from 11 to 15. In some embodiments, the metal catalysts has a $CO_2$ desorption of at least 200° C. Quantitative determination of the pKa and other methods to characterize the basicity of a catalyst support such as hydrotalcite are known in the art. See, e.g., A. Corma, et al., *J. of Catalysis*, 1992, 134, 58 and D. Debecker, et al., *Chem. Eur. J.*, 2009, 15, 3920.

It should be understood that the metal catalyst can be prepared by any methods known to one of skill in the art. For example, impregnation (e.g., incipient wetness impregnation) is one exemplary technique that can be used. In one example, a support such as hydrotalcite), and metal salt such as palladium chloride or copper acetate) can be combined and a solvent such as water is added. The metal salt and support are allowed to react for a period of time between 1 and 24 hours at a temperature between room temperature and 200° C., or more specifically between 50 and 120° C.

The reaction mixture may be stirred under a hydrogen atmosphere. The solid catalyst is then filtered and washed with copious amounts of solvent. The solid may then be dried under vacuum at a temperature between 80 and 150° C. Optionally, other additives may be added to the reaction mixture such as alkali metal salts (e.g., sodium chloride or potassium chloride) or base as described above.

The metal catalyst may also be prepared by impregnation (e.g., incipient wetness impregnation) of metal salts on basic supports, followed by calcination at temperatures higher than 300° C. in air or inert gases and/or reduction in mixtures of hydrogen and inert gases. Alternatively, the metal catalyst may be prepared by synthesizing metal nanoparticle ex situ and supporting said nanoparticles on the basic metal support using a solvent. In some embodiments, the metal catalyst prepared by impregnation (e.g., incipient wetness impregnation) includes at least two metals. In some embodiments, the metal catalyst contains Pd and Cu. In some embodiments, the metal catalyst contains Pd/Cu. For example, the ratio of Pd and Cu can vary, in which Pd may be in molar excess of Cu (e.g., in a 2:1 molar ratio), or Cu may be in molar excess of Pd (e.g., in a 1:2 molar ratio).

The metal catalyst may also be prepared by using the aforementioned methods for supporting metals on basic supports, with the difference that the supports are inert and include $SiO_2$ and carbon. The basic supports are also prepared as mentioned above, but no metal is supported on them. The basic supports and the metal catalysts are physically mixed before the reaction.

The metal catalyst may also be prepared by simultaneous or successive impregnation (e.g., incipient wetness impregnation) of solutions of nitrate or acetate salts of alkali or alkaline earth metals and appropriate salts or complexes of the metals disclosed herein onto inert supports, followed by calcination and reduction in conditions mentioned above. Alternatively, the metal catalyst may be prepared by impregnation (e.g., incipient wetness impregnation) of alkali salts onto inert supports, followed by calcination and impregnation (e.g., incipient wetness impregnation) of ex-situ synthesized metal nanoparticles.

Other Examples

The catalyst may include hydrotalcite. In certain embodiments, the catalyst includes hydrotalcite and one or more metals, or two or more metals. The one or more metals, or two or more metals, may include, for example, palladium (Pd), copper (Cu), nickel (Ni), zinc (Zn), ruthenium (Ru), cobalt (Co), and platinum (Pt). The hydrotalcite may be used as part of the catalyst in one or more ways. For example, in one embodiment, the hydrotalcite may include one or more metals deposited by coprecipitation or impregnation (e.g., incipient wetness impregnation). Such examples may include Pd/HT, Cu/HT, and Pd—Cu/HT. In another embodiment, the hydrotalcite may be coprecipitated or impregnated on carbon support (e.g., HT/C), and one or more metals may be coprecipitated or impregnated on such carbon support. Such examples may include Pd/HT/C or Pd—Cu/HT/C. In certain embodiments, the hydrotalcite may be mixed with carbon to produce a support (e.g., HT-C), and one or more metals may be coprecipitated or impregnated on such carbon support. Such examples may include Pd/HT-C or Pd—Cu/HT-C. In yet another embodiment, hydrotalcite may be used alone, or in combination with other catalysts such that the HT is one catalyst out of a mixture of catalysts used. Such an example may include a mixture of catalysts: $Cu/SiO_2$ and Pd/C and HT.

In some embodiments, the catalyst includes: (i) one or more, or two or more, metals such as palladium (Pd), copper (Cu), or a combination thereof; and (i) hydrotalcite. In certain embodiments, the Pd, Cu, or a combination thereof may be coprecipitated or impregnated on the hydrotalcite by methods known in the art. In certain embodiments, the hydrotalcite may be impregnated on carbon support by methods known in the art. In yet other embodiments, the catalyst may further include $TiO_2$. For example, suitable catalysts may include Pd—Cu/HT; Pd—Cu/HT-C; Pd—Cu/HT and $TiO_2$; or Pd—Cu/HT-C and $TiO_2$.

The catalyst may include lanthanum oxide ($La_2O_3$). The $La_2O_3$ may be prepared from any suitable methods known in the art. For example, the $La_2O_3$ may be prepared from the calcination of $La_2(C_2O_4)_3$ or $La_2(NO_3)_3$ at or above 500° C. In certain embodiments, the catalyst includes $La_2O_3$ and one or more metals. The one or more metals may include, for example, palladium (Pd), copper (Cu), nickel (Ni), zinc (Zn), ruthenium (Ru), cobalt (Co), and platinum (Pt). The $La_2O_3$ may be used as part of the catalyst in one or more ways. For example, in one embodiment, the $La_2O_3$ may include one or more metals deposited by coprecipitation or impregnation (e.g., incipient wetness impregnation). In another embodiment, the $La_2O_3$ may be coprecipitated or impregnated on carbon support (e.g., $La_2O_3/C$). In yet another embodiment, the $La_2O_3$ may be used in combination with other catalysts such that the $La_2O_3$ is one catalyst out of a mixture of catalysts used. For instance, the $La_2O_3$ may be used in a mixture with one or more metal-containing catalysts. Such examples may include a mixture of catalysts: $Cu/SiO_2$ and Pd/C and $La_2O_3/C$; or $Cu/ZnO/Al_2O_3$ and Pd/C and $La_2O_3$ and $TiO_2$; or $Cu/ZnO/Al_2O_3$ and $La_2O_3$.

The catalyst may include magnesium oxide (MgO). In certain embodiments, the catalyst includes MgO and one or more metals. The one or more metals may include, for example, palladium (Pd), copper (Cu), nickel (Ni), zinc (Zn), ruthenium (Ru), cobalt (Co), and platinum (Pt). The MgO may be used as part of the catalyst in one or more ways. For example, in one embodiment, the MgO may include one or more metals (including one or more metal oxides) deposited by coprecipitation or impregnation (e.g., incipient wetness impregnation). Such examples may include Cu/MgO, SrO/MgO, or CaO/MgO. In another embodiment, the MgO may be co-precipitated or impregnated on carbon support or silica support. Such examples include MgO/C, and $MgO/SiO_2$. In yet another embodiment, the MgO may be used in combination with other catalysts such that the MgO is one catalyst out of a mixture of catalysts used. For instance, the MgO may be used in a mixture with one or more metal-containing catalysts. Such examples may include a mixture of catalysts: $Cu/ZnO/Al_2O_3$ and $MgO/SiO_2$; or $Cu/ZnO/Al_2O_3$ and SrO/MgO; or $Cu/ZnO/Al_2O_3$ and CaO/MgO; or $Cu/SiO_2$ and CaO/MgO; or PdCu—CaO/MgO; or $Cu/ZnO/Al_2O_3$ and MgO; or $Cu/ZnO/Al_2O_3$, Pd/C and MgO.

The catalyst may include titanium dioxide ($TiO_2$). In certain embodiments, the catalyst includes $TiO_2$ and one or more metals. The one or more metals may include, for example, palladium (Pd), copper (Cu), nickel (Ni), zinc (Zn), ruthenium (Ru), cobalt (Co), and platinum (Pt). The $TiO_2$ may be used as part of the catalyst in one or more ways. For example, in one embodiment, the $TiO_2$ may include one or more metals deposited by coprecipitation or impregnation (e.g., incipient wetness impregnation). In another embodiment, the $TiO_2$ may be co-precipitated or impregnated on carbon support (e.g., $TiO_2/C$). In yet another embodiment, the $TiO_2$ may be used in combination with other catalysts such that the $TiO_2$ is one catalyst out of a mixture of catalysts used. For instance, the $TiO_2$ may be used in a mixture with one or more metal-containing catalysts. Such examples may include a mixture of catalysts: Pd—Cu/HT and TiO$_2$; Pd—Cu/HT-C and TiO$_2$; Cu/ZnO/Al$_2$O$_3$ and Pd/C and La$_2$O$_3$ and TiO$_2$; or Cu/ZnO/Al$_2$O$_3$ and Pd/C and CeO$_2$ and TiO$_2$; or Cu/ZnO/Al$_2$O$_3$ and Pd/C and MgO and TiO$_2$.

In certain embodiments, the catalyst includes Pd—Cu/HT, Pd—Cu/HT-C, Pd—Cu/HT/C, Pd/HT, Cu/HT, Cu/ZnO/Al$_2$O$_3$, hydroxyapatite, perovskite, Cu/MgO, (Cu/ZnO/Al$_2$O$_3$)/HT, BaO/SiO$_2$, MgO/SiO$_2$, SrO/SiO$_2$, CaO/SiO$_2$, SrO/MgO, CaO/MgO, Pd—Cu/NiHT, Cu/NiHT, PdCu/ZnHT, Cu/ZnHT, PdCu/ZnHT, Ru/HT, Cu—Ru/HT, Co/HT, Pt/HT, Pt—Cu/HT, Cu/SiO$_2$, Pd/C, CaO/C, SrO/C, BaO/C, La$_2$O$_3$/C, CeO$_2$/C, HT/C, HT, CeO$_2$, La$_2$O$_3$, TiO$_2$, or zeolite. For clarity, it should be understood that "Pd—Cu/HT-C" refers to palladium and copper impregnated on a support of hydrotalcite mixed with carbon, where as "Pd—Cu/HT/C" refers to palladium and copper impregnated on a support of hydrotalcite impregnated on carbon. It should also be understood that any combinations of the catalysts above may be used. In certain embodiments, any combinations of the catalysts above may be used, provided that at least one metal (including, for example, at least one metal oxide) is present in the catalyst.

In one embodiment, the catalyst includes:
Pd—Cu/HT;
Pd—Cu/HT/C;
Pd—Cu/HT and zeolite;
Pd—Cu/HT/C and zeolite;
Pd—Cu/HT and TiO$_2$;
Pd—Cu/HT-C and TiO$_2$;
Pd—Cu/HT/C and TiO$_2$;
Pd/HT;
Cu/HT;
Pd/C and HT
Pd—Cu/C and HT
Pd/HT-C;
Pd/HT/C;
Pd—Cu/HT-C;
Cu/ZnO/Al$_2$O$_3$ and hydroxyapatite;
Cu/ZnO/Al$_2$O$_3$ and perovskite;
Cu/MgO;
Cu/ZnO/Al$_2$O$_3$ and HT;
Cu/ZnO/Al$_2$O$_3$ and BaO/SiO$_2$;
Cu/ZnO/Al$_2$O$_3$ and MgO/SiO$_2$;
Cu/ZnO/Al$_2$O$_3$ and SrO/SiO$_2$;
Cu/ZnO/Al$_2$O$_3$ and CaO/SiO$_2$;
Cu/ZnO/Al$_2$O$_3$ and SrO/MgO;
Cu/ZnO/Al$_2$O$_3$ and CaO/MgO;
Cu/SiO$_2$ and CaO/MgO;
Pd—Cu/CaO—MgO;
Pd—Cu/NiHT;
Cu/NiHT;
Pd—Cu/ZnHT;
Cu/ZnHT;
Ru/HT;
Cu—Ru/HT;
Co/HT;
Pt/HT;
Pt—Cu/HT;
Cu/SiO$_2$, Pd/C and CaO/C;
Cu/SiO$_2$, Pd/C and SrO/C;
Cu/SiO$_2$, Pd/C and BaO/C;
Cu/SiO$_2$, Pd/C and La$_2$O$_3$/C;
Cu/SiO$_2$, Pd/C and CeO$_2$/C;
Cu/SiO$_2$, Pd/C and HT/C;
Cu/SiO$_2$, Pd/C and HT;
Cu/ZnO/Al$_2$O$_3$, Pd/C and HT;
Cu/ZnO/Al$_2$O$_3$ and CeO$_2$;
Cu/ZnO/Al$_2$O$_3$, Pd/C and CeO$_2$;
Cu/ZnO/Al$_2$O$_3$ and La$_2$O$_3$;
Cu/ZnO/Al$_2$O$_3$, Pd/C and La$_2$O$_3$;
Cu/ZnO/Al$_2$O$_3$, Pd/C, La$_2$O$_3$, and TiO$_2$;
Cu/ZnO/Al$_2$O$_3$, Pd/C, and CeO$_2$;
Cu/ZnO/Al$_2$O$_3$, Pd/C, CeO$_2$, and TiO$_2$,
Pd—Cu/ZnO/HT;
Cu/ZnO/HT;
Cu/ZnO/Al$_2$O$_3$ and MgO;
Cu/ZnO/Al$_2$O$_3$, Pd/C and MgO; or
Cu/ZnO/Al$_2$O$_3$, Pd/C, MgO, and TiO$_2$.

It should be understood that the exemplary catalysts described above may be used for any of the methods described herein, including methods that involve at least two or more alcohols (e.g., isopropanol-butanol-ethanol) or methods that involve acetone and two or more primary alcohols (e.g., acetone-butanol-ethanol).

The Base

In some embodiments, base is used in combination with the metal catalyst to convert the mixture of alcohols or the mixture of alcohols and ketones into a hydrocarbon ketone product mixture. It should be understood that, in certain embodiments, even when the metal catalyst has a basic support, base may additionally be added to the reaction mixture.

Bases that promotes alkylation of the ketone may be used. In certain embodiments, any base that promotes double alkylation of acetone may be used. In other embodiments, the base may also promote the reduction of the oligomerization of the ketone and formation the Guerbet product. In certain preferred embodiments, the base is K$_3$PO$_4$. In some embodiments, the base and metal catalyst are two separate components that may be combined and contacted with the reactants. In other embodiments, the base is first supported or impregnated on a support material typically containing the metal catalyst and contacted with the reactants.

Suitable bases may include inorganic bases (e.g., hydroxides of alkali metals and alkaline earth metals), and organic bases. Examples of inorganic bases may include potassium hydroxide, barium hydroxide, cesium hydroxide, sodium hydroxide, strontium hydroxide, calcium hydroxide, lithium hydroxide, rubidium hydroxide, magnesium hydroxide. Examples of organic bases may include triethylamine, trimethylamine, pyridine, and methyl amine.

In some embodiments, the base has a pKa from 10 to 16. In other embodiments, the base has a pKa from 11 to 15. In certain embodiments, the base is KOH, Ba(OH)$_2$.8H$_2$O, K$_2$CO$_3$, KOAc, KH$_2$PO$_4$, Na$_2$HPO$_4$, pyridine, or Et$_3$N.

The type of base used may be determined by the desired strength of the base and its ability to promote alkylation of a ketone, without producing undesirable side reactions or side products. The amount of base selected may affect the overall reaction yield, and the proportion of alkylated products. In certain embodiments, the type of base used may be determined by the desired strength of the base and its ability to promote double alkylation of acetone, without producing undesirable side reactions or side products. The amount of base selected may affect the overall reaction yield, and the proportion of double-alkylated products. For example, increasing the amount of base increases the overall reaction yield, as well as the selectivity for double-alkylation. In some embodiments, at least 0.3 mole equivalents of base are used. In other embodiments, between 0.32 to 1.3 mole equivalents of base are used. In yet other embodiments, between 0.9 to 1.5 mole equivalents of base are used. In yet other embodiments, between 0.95 to 1.3 mole equivalents of base are used. In certain embodiments, 0.95 mole equivalents of base are used.

In yet other embodiments, the base used may be calcined. In such embodiments, the base can be pretreated at a high temperature to obtain a more active material. For example, in one embodiment where $K_3PO_4$ is the base used, the $K_3PO_4$ may be heated at about 600° C. to obtain a material that is more active in promoting the alkylation reaction described herein.

The Solvent

In some embodiments, the methods of producing the hydrocarbon ketones is performed neat, i.e., without addition of a solvent. However, in other embodiments, the methods of producing the hydrocarbon ketones may be performed with a solvent.

Any solvent that promotes alkylation of the ketone may be employed in the process described herein. In certain embodiments, any solvent that promotes double alkylation of acetone may be employed in the process described herein. For example, the solvent may be an organic solvent. Organic solvents may include aromatics (e.g., toluene, benzene), ketones (e.g., acetone or methyl ethyl ketone), acetates (e.g., ethyl acetate or isopropylacetate), nitriles (e.g., acetonitrile), alcohols (e.g., butanol, ethanol, isopropanol), or ethers (e.g., diglyme, monoglyme, diglybu, THF). As used herein, "diglyme" refers to diethylene glycol dimethyl ether. As used herein, "diglybu" refers to diethylene glycol dibutyl ether.

A suitable solvent employed in the process described herein is one that may be used in the fermentation process, may be used in the extraction of the fermentation product mixture from the fermentation process, or may be blended directly with the products from the fermentation process. Other considerations include the promotion of the reaction rate, the formation of the reaction products, and the promotion or reduction of the Guerbet product and oligomerization of the ketone (e.g., acetone). In some embodiments, the solvent may include toluene, ethyl acetate, diglyme, monoglyme, butanol, diglybu, oleyl alcohol, dibutyl phthalate, or mixtures of these solvents.

The Reaction Conditions

Operating Temperature

The operating temperatures used in the methods described herein to produce the hydrocarbon ketones may vary. The operating temperature range refers to the range of temperatures across a reaction zone.

In some embodiments, the operating temperature is the reflux temperature of the solvent if one is used. In other embodiments, the reaction mixture containing the alcohols and the metal catalyst is heated to an operating temperature range suitable to increase selectivity for double-alkylated hydrocarbon ketones.

The operating temperature range selected may vary depending on various factors, including the solvent, base, and catalyst used. In some embodiments, the operating temperature range is between about 100° C. to about 400° C., between about 190° C. to about 350° C., or between about 220° C. to about 270° C.

In some embodiments, in reaction system where toluene is used as the solvent, the operating temperature range is between about 110° C. to about 250° C., or between about 180° C. to 250° C.

In some embodiments, the reaction may be exothermic and inter-stage cooling may be utilized to maintain the temperature at the operating temperature.

Operating Pressure

The operating pressure of the methods described herein to produce the hydrocarbon ketones may vary. The operating pressure refers to the pressure across a reaction zone. In some embodiments, the pressure in between 1 atm and 60 atm.

Reaction Time

In some embodiments, the reaction may be carried out for 24 hours, but the time of the reaction will also vary with the reaction conditions (e.g., reaction temperature), catalyst activity, desired yield, and desired conversion (e.g., low conversion with recycle). In some embodiments, the reaction time is determined by the rate of conversion of the starting material. In other embodiments, the reaction time is determined by the rate of double-alkylation of the starting material. In other embodiments, the reaction mixture is heated for 10 to 30 hours. In other embodiments, the reaction mixture is heated for 10 to 20 hours. In yet other embodiments, the reaction mixture is heated for 1 to 10 hours. In yet other embodiments, the reaction mixture is heated for 30 minutes to 10 hours.

Further, it should be understood that the reaction can be tuned to produce gasoline versus jet/diesel products. In some embodiments, gasoline products may include the shorter-chained products, such as 2-pentanone, 4-heptanone, and 2-heptanone. In other embodiments, jet/diesel products may include the heavier-chained products, such as 4-nonanone, 2-methyl-4-nonanone, and 6-undecanone.

Other Process Considerations

In some embodiments, the reaction would be in a plug flow reactor, such as a packed bed reactor, as either a single reactor or a multiple tube reactor. In some embodiments, unreacted feedstocks and/or one or more intermediate reaction products are separated from the products downstream of the reactor and recycled back into the reaction zone to be contacted with the catalyst. In some embodiments, the one or more intermediates is selected from the group consisting of 2-pentanone, 2-heptanone, 4-heptanone, and mixtures thereof In some embodiments, in situ formation of acetone in lower concentration via dehydrogenation of isopropanol during the IBE alkylation reaction favors the aldol condensation with 2-ethyl hexanol formed from the Guerbet reaction of butanol thereby increasing the concentration of $C_{11+}$ compounds in the mixture of hydrocarbon ketones. The additional hydrogen generated from isopropanol could be used for the reduction of ketones in order to improve fuel properties.

In some embodiments, the ABE or IBE feedstocks may be enriched in butanol and 2-ethylhexanol by reacting ethanol and butanol in a Guerbet reactor prior to the main ABE reactor. Also 2-ethylhexanol that is produced in the Guerbet reactor might be used in the synthesis of $C_{11+}$ compounds.

In some embodiments, addition of hydrogen into the feedstock may prevent deactivation of the catalyst by hydrogenating away precursors to carbonaceous deposits and may give a process handle to control the equilibrium between aldehydes/ketones and alcohols. In some embodiments, the addition of hydrogen may also improve the thermodynamics and kinetics, by accelerating hydrogenation of the α,β-unsaturated aldehydes and by hydrogenating the ketone end product to an alcohol which may have a positive effect on the fuel properties.

In some embodiments, the reaction may be performed in a plug flow reactor (PFR). A PFR may not operate at 100% conversions. Instead, it may operate at lower conversions and the unreacted feedstock is separated from the products downstream of the reactor and recycled back into the PFR.

In some embodiments, in both the ABE and IBE reactions, butyl butyrate and long chain esters are formed (6% yield based on butanol). In some embodiments, the esters could be hydrogenated back to alcohols.

In some embodiments, the catalyst is recycled or unconverted feedstock is recycled. In some embodiments, after the first catalytic cycle, the supernatant is separated from the solid catalyst after centrifugation. The solid is washed with a solvent (e.g., ethanol) multiple times (e.g., 3-4) and is dried. The dried solid may then be added to reactants and subsequent cycles may be carried out.

In some embodiments, if operated in a plug-flow reactor system, catalyst regeneration may include heating at 500° C. under air in order to combust carbonaceous deposits on the catalysts. Unconverted feedstock may be separated from the products by distillation and returned to the reactor.

Figure 11:
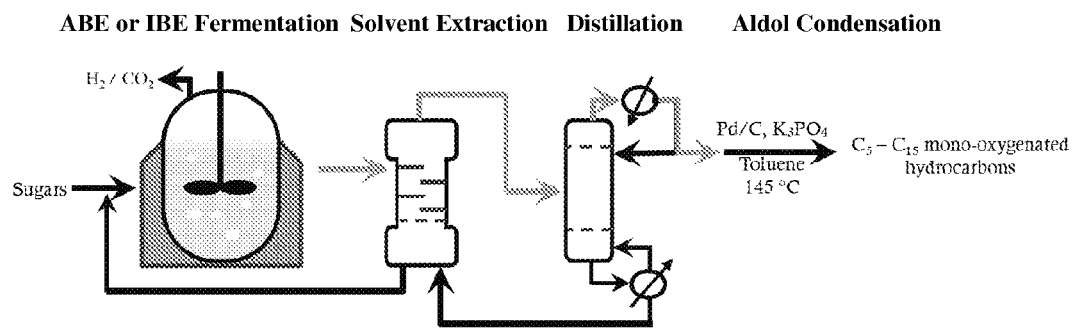
FIG. 11 depicts an exemplary integrated system including fermentation, extraction, and catalysis.

An exemplary integrated system including fermentation, extraction, and catalysis is shown in FIG. 11. In some embodiments, such an integrated system may be used for an ABE or IBE process.

The Hydrocarbon Ketone Product Mixture and Their Uses

The methods described herein can convert a mixture of alcohols or a mixture of ketones and alcohols into a mixture of hydrocarbon ketones suitable for use as components in fuels (e.g., gasoline, jet and diesel fuels).

As used herein, a "hydrocarbon ketone" refers to a compound made up of hydrogen and carbon atoms, and at least one —C=O group in which the carbon of the carbonyl group is bonded to two carbon atoms. In some embodiments, the hydrocarbon ketone has one —C=O group. For example, in certain embodiments, the hydrocarbon ketone has a structure of formula (I):

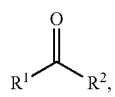
(I)

wherein each $R^1$ and $R^2$ is independently alkyl, alkenyl, alkynyl, cycloalkyl, aryl, or heteroaryl.

"Alkyl" refers to a monoradical unbranched or branched saturated hydrocarbon chain. In some embodiments of the compounds of formula (I), alkyl has 1 to 20 carbon atoms (i.e., $C_{1-20}$ alkyl), 1 to 10 carbon atoms (i.e., $C_{1-10}$ alkyl), 1 to 8 carbon atoms (i.e., $C_{1-8}$ alkyl), 1 to 6 carbon atoms (i.e., $C_{1-6}$ alkyl), or 1 to 4 carbon atoms (i.e., $C_{1-4}$ alkyl). Examples of alkyl groups include methyl, ethyl, propyl, isopropyl, n-butyl, sec-butyl, tert-butyl, pentyl, 2-pentyl, isopentyl, neopentyl, hexyl, 2-hexyl, 3-hexyl, and 3-methylpentyl. When an alkyl residue having a specific number of carbons is named, all geometric isomers having that number of carbons may be encompassed; thus, for example, "butyl" can include n-butyl, sec-butyl, isobutyl and t-butyl; "propyl" can include n-propyl and isopropyl.

"Alkenyl" refers to an unsaturated hydrocarbon group having at least one site of olefinic unsaturation (i.e., having at least one moiety of the formula C=C).

"Alkynyl" refers to an unsaturated hydrocarbon group having at least one site of acetylenic unsaturation (i.e., having at least one moiety of the formula C≡C).

"Cycloalkyl" refers to a cyclic alkyl group. In some embodiments of the compounds of formula (I), cycloalkyl has from 3 to 20 ring carbon atoms (i.e., $C_{3-20}$ cycloalkyl), or 3 to 12 ring carbon atoms (i.e., $C_{3-12}$ cycloalkyl), or 3 to 8 ring carbon atoms (i.e., $C_{3-8}$ cycloalkyl). Examples of cycloalkyl groups include cyclopropyl, cyclobutyl, cyclopentyl, and cyclohexyl.

"Aryl" refers to an aromatic carbocyclic group having a single ring (e.g., phenyl), multiple rings (e.g., biphenyl), or multiple fused rings (e.g., naphthyl, fluorenyl, and anthryl). In certain embodiments of the compounds of formula (I), aryl has 6 to 20 ring carbon atoms (i.e., $C_{6-20}$ aryl), or 6 to 12 carbon ring atoms (i.e., $C_{6-12}$ aryl).

"Heteroaryl" refers to an aryl group, wherein at least one carbon atom of the designated carbocyclic group has been replaced by a heteroatom selected from N, O and S.

In certain embodiments, the hydrocarbon ketone is an alkanone. "Alkanone" refers to compounds with alkyl chains, and at least one —C=O group. The alkyl chains of the alkanone may be linear or branched. Examples of alkanones include pentanone, heptanone, heptanone, nonanone, and undecanone. In certain embodiments, the alkanones have a linear arrangement, such as 2-pentanone, 4-heptanone, 2-heptanone, 4-nonanone, and 6-undecanone. In other embodiments, the alkanones have a branched arrangement, such as 2-methyl-4-nonanone. In some embodiments, alkanones include those with at least five carbons ($C_{5+}$ alkanones), at least seven carbons ($C_{7+}$ alkanones), at least nine carbons ($C_{9+}$ alkanones), or at least ($C_{11+}$ alkanones), or between five and twenty carbons ($C_5$-$C_{20}$ alkanones), between seven and twenty carbons ($C_7$-$C_{20}$ alkanones), or between eleven and twenty carbons ($C_{11}$-$C_{20}$ alkanones).

The starting materials, metal catalyst, base, solvent and/or reactions conditions can be selected to tune the yield of the hydrocarbon ketone product mixture. For example, the metal catalyst, base, solvent and/or reactions conditions can be selected to favor double-alkylation and/or the production of heavier hydrocarbon ketones in the mixture.

As used herein, the term "yield" refers to the total amount of product relative to the amount of ketone precursor (e.g., secondary alcohol, such as isopropanol) or ketone (e.g., acetone) present in the starting reaction mixture. For example, where multiple ketone compounds are present in the product mixture, the overall reaction yield refers to the combined molar yields of the ketone products, calculated with respect to the molar amount of ketone precursor or ketone present in the starting reaction mixture.

In certain embodiments, the reaction conditions yield hydrocarbon ketones (e.g., alkanones) with molecular weights suitable for use as fuels. For example, alkanones suitable for use as fuels may include those with at least 5 carbons, at least 7 carbons, or at least 11 carbons. In certain embodiments, the alkanones produced using the methods described herein are unbranched. In other embodiments, the alkanones produced are branched.

In one embodiment, the hydrocarbon ketone has a structure of formula (I):

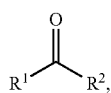
(I)

wherein each $R^1$ and $R^2$ is independently alkyl.

In certain embodiments, $R_1$ and $R_2$ may be independently substituted or unsubstituted alkyls. The alkyls may be any length. In some embodiments, each $R_1$ and $R_2$ is independently methyl, ethyl, propyl, isopropyl, butyl, pentyl, hexyl, heptyl, or octyl.

In other embodiments, the one or more compounds of Formula (I) are $C_5$-$C_{19}$ ketones. In other embodiments, the one or more compounds of Formula (I) are $C_5$-$C_{11}$ ketones. In yet other embodiments, the one or more compounds of Formula (I) are $C_{11}$-$C_{19}$ ketones.

In certain embodiments, the one or more compounds of Formula (I) may include

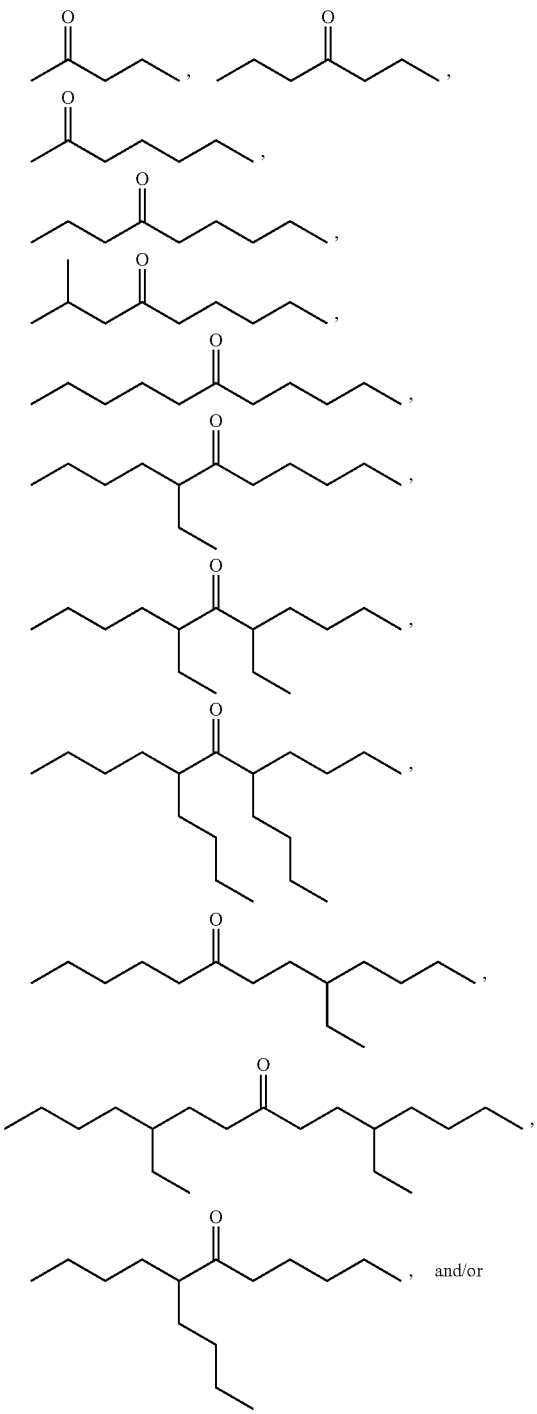

While mono-alkylated products may be produced according to the process described herein, in certain embodiments, at least one of one or more compounds of Formula (I) is a double-alkylated product. In some embodiments, at least 50% of the product mixture is made up of one or more double-alkylated products. In other embodiments, less than 20% of the product mixture is made up of one or more mono-alkylated products.

In some embodiments, where the reaction mixture contains a ketone (e.g., acetone) or a secondary alcohol such as isopropanol that is oxidized to a ketone, at least 5%, 10%, 20%, 30%, 40%, 50%, 60%, 70%, 80%, or 90% of the mixture of hydrocarbon ketones is produced from double alkylation of the ketone. In some embodiments, at least 70% of the mixture of hydrocarbon ketones is produced from double alkylation of the ketone. In some embodiments, at least 80% of the mixture of hydrocarbon ketones is produced from double alkylation of the ketone. In some embodiments, at least 90% of the mixture of hydrocarbon ketones is produced from double alkylation of the ketone.

In some embodiments, the mixture of hydrocarbon ketones is a mixture of $C_{7+}$ hydrocarbon ketones. In some embodiments, at least 5%, 10%, 20%, 30%, 40%, 50%, 60%, 70%, 80%, or 90% of the mixture of hydrocarbon ketones is $C_{7+}$ ketones. In some embodiments, at least 70% of the mixture of hydrocarbon ketones is $C_{7+}$ ketones. In some embodiments, at least 80% of the mixture of hydrocarbon ketones is $C_{7+}$ ketones. In some embodiments, at least 90% of the mixture of hydrocarbon ketones is $C_{7+}$ ketones.

In some embodiments, the mixture of hydrocarbon ketones is a mixture of $C_{11+}$ hydrocarbon ketones. In some embodiments, at least 5%, 10%, 20%, 30%, 40%, 50%, 60%, 70%, 80%, or 90% of the mixture of hydrocarbon ketones is $C_{11+}$ ketones. In some embodiments, at least 30% of the mixture of hydrocarbon ketones is $C_{11+}$ ketones. In some embodiments, at least 40% of the mixture of hydrocarbon ketones is $C_{11+}$ ketones. In some embodiments, at least 50% of the mixture of hydrocarbon ketones is $C_{11+}$ ketones. In some embodiments, at least 60% of the mixture of hydrocarbon ketones is $C_{11+}$ ketones. In some embodiments, at least 70% of the mixture of hydrocarbon ketones is $C_{11+}$ ketones. In some embodiments, at least 80% of the mixture of hydrocarbon ketones is $C_{11+}$ ketones. In some embodiments, at least 90% of the mixture of hydrocarbon ketones is $C_{11+}$ ketones.

In some embodiments, the mixture of hydrocarbon ketones is a mixture of $C_{15+}$ hydrocarbon ketones. In some embodiments, at least 5%, 10%, 20%, 30%, 40%, 50%, 60%, 70%, 80%, or 90% of the mixture of hydrocarbon ketones is $C_{15+}$ ketones. In some embodiments, at least 30% of the mixture of hydrocarbon ketones is $C_{15+}$ ketones. In some embodiments, at least 40% of the mixture of hydrocarbon ketones is $C_{15+}$ ketones. In some embodiments, at least 50% of the mixture of hydrocarbon ketones is $C_{15+}$ ketones. In some embodiments, at least 60% of the mixture of hydrocarbon ketones is $C_{15+}$ ketones. In some embodiments, at least 70% of the mixture of hydrocarbon ketones is $C_{15+}$ ketones. In some embodiments, at least 80% of the mixture of hydrocarbon ketones is $C_{15+}$ ketones. In some embodiments, at least 90% of the mixture of hydrocarbon ketones is $C_{15+}$ ketones.

In some embodiments, the mixture of hydrocarbon ketones is a mixture of $C_7$-$C_{19}$ hydrocarbon ketones. In some embodiments, at least 5%, 10%, 20%, 30%, 40%, 50%, 60%, 70%, 80%, or 90% of the mixture of hydrocarbon ketones is $C_7$-$C_{19}$ ketones. In some embodiments, at least 70% of the mixture of hydrocarbon ketones is $C_7$-$C_{19}$ ketones. In some embodiments, at least 80% of the mixture of hydrocarbon ketones is $C_7$-$C_{19}$ ketones. In some embodiments, at least 90% of the mixture of hydrocarbon ketones is $C_7$-$C_{19}$ ketones.

In some embodiments, the mixture of hydrocarbon ketones is a mixture of $C_7$-$C_{15}$ hydrocarbon ketones. In some embodiments, at least 5%, 10%, 20%, 30%, 40%, 50%, 60%, 70%, 80%, or 90% of the mixture of hydrocarbon ketones is $C_7$-$C_{15}$ ketones. In some embodiments, at least 70% of the mixture of hydrocarbon ketones is $C_7$-$C_{15}$ ketones. In some embodiments, at least 80% of the mixture of hydrocarbon ketones is $C_7$-$C_{15}$ ketones. In some embodiments, at least 90% of the mixture of hydrocarbon ketones is $C_7$-$C_{15}$ ketones.

In some embodiments, the mixture of hydrocarbon ketones is selected from the group consisting of 2-pentanone, 4-heptanone, 2-heptanone, 4-nonanone, 2-methyl-4-nonanone, 6-undecanone, 5-ethylundecan-6-one, 5,7-diethylundecan-6-one, 5,7-dibutylundecan-6-one, 9-ethyltridecan-6-one, 5,11-diethylpentadecan-8-one, 5-butylundecan-6-one, 5-butyl-7-ethylundecan-6-one, and any combinations thereof. In some embodiments, the mixture of hydrocarbon ketones is selected from the group consisting of 2-pentanone, 4-heptanone, 2-heptanone, 4-nonanone, 2-methyl-4-nonanone, 6-undecanone, and any combinations thereof. In some embodiments, at least 20% of the mixture of hydrocarbon ketones is $C_{7+}$ hydrocarbon ketones. In some embodiments, at least 20% of the mixture of hydrocarbon ketones is $C_{11+}$ hydrocarbon ketones.

In some embodiments, the choice of metal catalyst can lead to a significant increase in rate of the formation of higher hydrocarbon ketones, including, for example, $C_{11+}$ hydrocarbon ketones. In some embodiments, metal catalyst containing two or more metals may lead to the increase in rate of formation of higher hydrocarbon ketones, such as a Pd/Cu alloy. The alloy may have a molar excess of Pd compared to Cu (e.g., a 2:1 molar ratio of Pd:Cu), or a molar excess of Cu compared to Pd (e.g., a 1:2 molar ratio of Pd:Cu), or a 1:1 molar ratio of metals. In some embodiments, metal catalyst including two or more metals forms $C_5$-$C_{11}$ ketones at a rate 2.5 times the rate of formation of $C_5$-$C_{11}$ ketones by metal catalyst including one of the two or more metals. In some embodiments, metal catalyst including two or more metals forms $C_5$-$C_{11}$ ketones at a rate 5.6 times the rate of formation of $C_5$-$C_{11}$ ketones by metal catalyst including one of the two or more metals. In some embodiments, metal catalyst including two or more metals forms $C_{11+}$ ketones at a rate 33 times the rate of formation of $C_{11+}$ ketones by metal catalyst including one of the two or more metals. The rate of formation of the ketone products may be measured by a variety of techniques, including analysis of the reaction mixture at various time intervals by GC analysis.

Following the production of one or more compounds of Formula (I), these one or more compounds may be further hydrogenated, deformylated, isomerized, hydrodeoxygenated, or catalytically reformed. The double-alkylated products may be subsequently converted to either corresponding alcohols or alkanes, suitable for the manufacture of a fuel.

Provided herein are also methods to further convert one or more of the hydrocarbon ketones into one or more alcohols suitable for use as fuels. Examples of such alcohols may include:

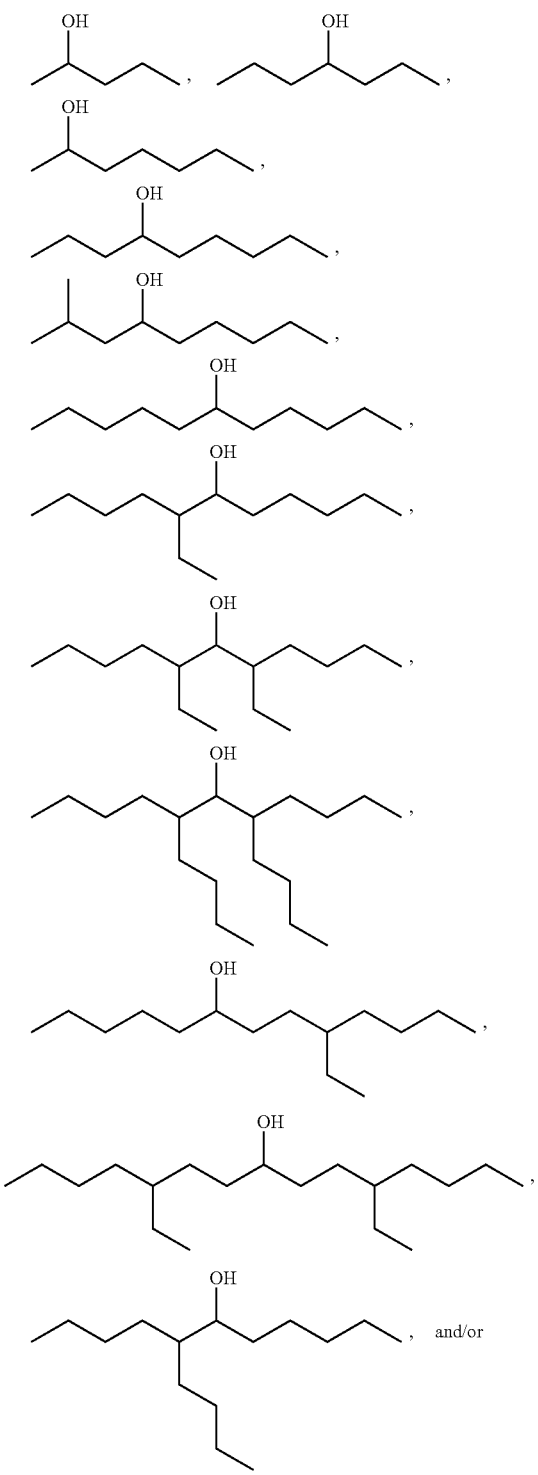

and/or

-continued

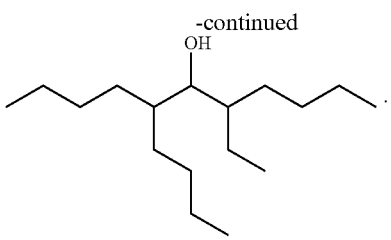

In some embodiments, the one or more compounds of Formula (I) may be converted into their corresponding alcohols in the presence of metal catalyst. In certain embodiments, the metal catalyst includes platinum. In a specific embodiment, the second metal catalyst is palladium on carbon (Pd/C).

Provided herein are also methods to convert the hydrocarbon ketones to into one or more alkanes. Examples of such alcohols may include:

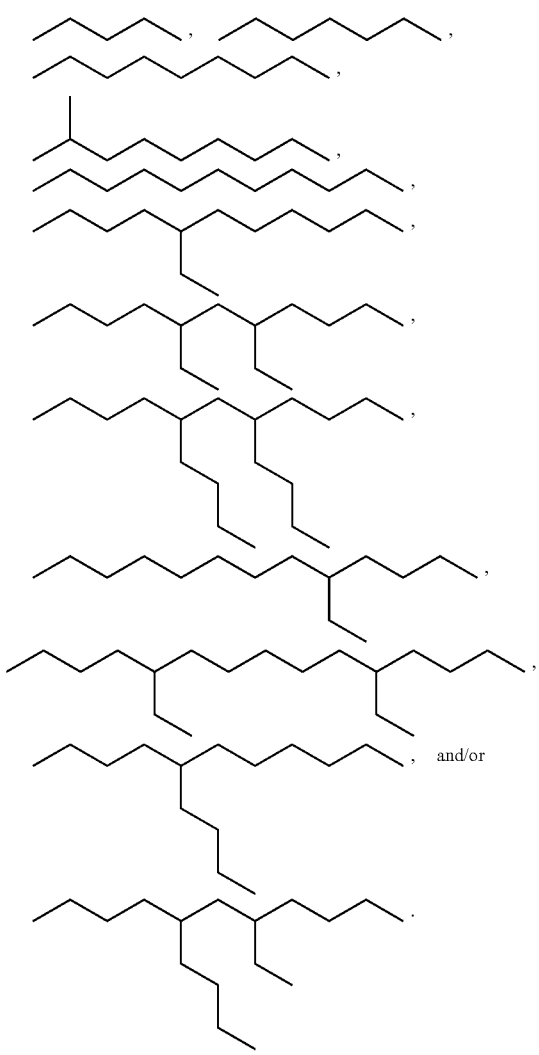

In other embodiments, the one or more compounds of Formula (I) may be converted into their corresponding alkanes in the presence of metal catalyst. In certain embodiments, the metal catalyst includes platinum, nickel-molybdenum (Ni—Mo), nickel-tungsten (Ni—W), cobalt-molybdenum (Co—Mo), or combinations of these metals. In specific embodiments, the second metal catalyst is NiO—MoO$_3$/Al$_2$O$_3$, Pt/SiO$_2$—Al$_2$O$_3$, or combinations of these catalysts.

In some embodiments, ketones such as 4-heptanone, 4-nonanone, and 6-undecanone, produced by the methods disclosed herein may be further deoxygenated to produce heptane, nonane, and undecane, respectively. These alkanes may be blended into diesel and jet fuel, or may be used independently as fuels following minor refinery upgrading. In some embodiments, the double-alkylated products obtained from the process described herein may be suitable for use as fuels that can power transportation vehicles (e.g., jets, diesel vehicles) and other combustion turbine applications.

It should be understood that the methods described herein may produce a mixture of compounds of Formula (I) or a mixture of alkanones. In certain embodiments, each of the compounds of Formula (I), or each of the alkanones, in the product mixture can be separated before use in producing the corresponding alcohol or alkane.

As used herein, "fuel" refers to a composition made up of a compound containing at least one carbon-hydrogen bond, which produces heat and power when burned. Fuel may be produced using plant-derived biomass as a feedstock, for example, lignocellulose. Fuel may also contain more than one type of compound, and includes mixtures of compounds. As used herein, the term "transportation fuel" refers to a fuel that is suitable for use as a power source for transportation vehicles. Suitable fuels may include, for example, gasoline, jet and diesel fuels.

Fuels or fuel components may also be obtained from the Guerbet reaction that may take place. For example, in some embodiments, the dimerization of butanol via Guerbet reaction may be followed by alkylation with acetone or 2-butanone in a one-pot two-step process to yield one or more ketones ranging from $C_{11}$-$C_{27}$.

Provided herein are also compositions that include a fuel (e.g., gasoline, jet or diesel) and one or more hydrocarbon ketones, or a mixture of hydrocarbon ketones, produced according to any of the methods described herein.

For example, in some embodiments, the composition is a gasoline fuel composition that includes a gasoline fuel or a gasoline blending stock, and one or more hydrocarbon ketones, or any derivatives thereof (e.g., alcohols, alkanes), that are produced according to any of the methods described herein. In certain embodiments of the gasoline fuel composition, the one or more hydrocarbon ketones are $C_5$-$C_7$ hydrocarbon ketones.

In other embodiments, the composition is a jet fuel composition that includes a jet fuel or a jet blending stock, and one or more hydrocarbon ketones, or any derivatives thereof (e.g., alcohols, alkanes), that are produced according to any of the methods described herein. In certain embodiments of the jet fuel composition, the one or more hydrocarbon ketones are $C_7$-$C_{11}$ hydrocarbon ketones.

In yet other embodiments, the composition is a diesel fuel composition that includes a diesel fuel or a diesel blending stock, and one or more hydrocarbon ketones, or any derivatives thereof (e.g., alcohols, alkanes), that are produced according to any of the methods described herein.

In certain embodiments of the diesel fuel composition, the one or more hydrocarbon ketones are one or more $C_{7+}$ hydrocarbon ketones.

As used herein, the term "about" refers to an approximation of a stated value within an acceptable range. Preferably, the range is +/−10% of the stated value.

ENUMERATED EMBODIMENTS

The following enumerated embodiments are representative of some aspects of the invention.

1. A method of producing a mixture of hydrocarbon ketones, comprising contacting at least two or more alcohols with metal catalyst and optionally base to produce a mixture of hydrocarbon ketones, wherein at least one of the two or more alcohols is a secondary alcohol.
2. The method of embodiment 1, wherein the at least two or more alcohols are $C_1$-$C_{20}$ alcohols, and wherein at least one of the two or more alcohols is a secondary $C_3$-$C_{20}$ alcohol.
3. The method of embodiment 1 or 2, wherein the secondary alcohol is isopropanol, 2-butanol, 2-pentanol, 2-hexanol, 2-heptanol, 2-octanol, 2-nonanol, 2-decanol, 2-undecanol, 2-dodecanol, 2-tridecanol, 2-tetradecanol, 2-pentadecanol, 2-hexadecanol, 2-heptadecanol, 2-octadecanol, 2-nonadecanol, 2-icosanol, 2,3-butanediol, acetoin, or any combination thereof.
4. The method of any of embodiments 1 to 3, wherein the two or more alcohols are two alcohols or three alcohols.
5. The method of embodiment 4, wherein the two alcohols are isopropanol and n-butanol.
6. The method of embodiment 4, wherein the three alcohols are isopropanol, n-butanol and ethanol.
7. The method of embodiment 4, wherein the three alcohols are 2-butanol, n-butanol and ethanol.
8. A method of producing a mixture of hydrocarbon ketones, comprising contacting a secondary alcohol and one or more primary alcohols with metal catalyst and optionally base to produce a mixture of hydrocarbon ketones.
9. The method of embodiment 8, wherein the secondary alcohol is a $C_3$-$C_{20}$ alcohol.
10. The method of embodiment 8 or 9, wherein the secondary alcohol is isopropanol, 2-butanol, 2-pentanol, 2-hexanol, 2-heptanol, 2-octanol, 2-nonanol, 2-decanol, 2-undecanol, 2-dodecanol, 2-tridecanol, 2-tetradecanol, 2-pentadecanol, 2-hexadecanol, 2-heptadecanol, 2-octadecanol, 2-nonadecanol, 2-icosanol, 2,3-butanediol, acetoin, or any combination thereof.
11. The method of any one of embodiments 8 to 10, wherein the one or more primary alcohols are $C_1$-$C_{20}$ alcohols.
12. The method of any one of embodiments 8 to 11, wherein the one or more primary alcohols are n-butanol, ethanol, or 2-ethyl-hexanol, or any combination thereof.
13. The method of any one of embodiments 8 to 12, wherein the secondary alcohol is isopropanol, and the one or more primary alcohols are butanol and ethanol.
14. The method of embodiment 13, wherein the isopropanol and ethanol are provided in a ratio of about 2.3 to about 1.
15. The method of embodiment 14, wherein the butanol is provided in stoichiometric excess of the isopropanol and ethanol.
16. The method of embodiment 8, wherein the secondary alcohol is 2-butanol, and the one or more primary alcohols are n-butanol, ethanol, or any combination thereof.
17. The method of any one of embodiments 1 to 16, wherein contacting the secondary alcohol with the metal catalyst and optionally the base oxidizes the secondary alcohol to produce a ketone.
18. The method of embodiment 17, wherein at least a portion of the mixture of hydrocarbon ketones are produced from double alkylation of the ketone.
19. The method of embodiment 18, wherein at least 70% of the mixture of hydrocarbon ketones are produced from double alkylation of the ketone.
20. The method of any one of embodiments 1 to 19, wherein the mixture of hydrocarbon ketones is a mixture of $C_{5-15}$ hydrocarbon ketones.
21. The method of any one of embodiments 1 to 20, wherein the mixture of hydrocarbon ketones is selected from the group consisting of 2-pentanone, 4-heptanone, 2-heptanone, 4-nonanone, 2-methyl-4-nonanone, 6-undecanone, 5-ethylundecan-6-one, 5,7-diethylundecan-6-one, 5,7-dibutylundecan-6-one, 9-ethyltridecan-6-one, 5,11-diethylpentadecan-8-one, 5-butylundecan-6-one, 5-butyl-7-ethylundecan-6-one, and any combinations thereof.
22. The method of embodiment 21, wherein the mixture of hydrocarbon ketones is selected from the group consisting of 2-pentanone, 4-heptanone, 2-heptanone, 4-nonanone, 2-methyl-4-nonanone, 6-undecanone, and any combinations thereof.
23. The method of any one of embodiments 1 to 22, wherein at least 70% of the mixture of hydrocarbon ketones is $C_{7+}$ hydrocarbon ketones.
24. The method of any one of embodiments 1 to 23, wherein at least 40% of the mixture of hydrocarbon ketones is $C_{11+}$ hydrocarbon ketones.
25. The method of any one of embodiments 1 to 24, wherein the secondary alcohol and the one or more primary alcohols are produced by a process comprising:
providing biomass or sugars; and
contacting biomass or sugars with a fermentation host to produce the secondary alcohol and the one or more primary alcohols in a fermentation product mixture.
26. The method of embodiment 25, further comprising isolating the secondary alcohol and one or more of the primary alcohols in the fermentation product mixture using an extractant.
27. The method of embodiment 26, wherein the extractant has one or more of the following properties:
   i) is non-toxic to *Clostridium*; and
   ii) has partition coefficients for the primary alcohol and the secondary alcohol equal to or greater than 1.
28. The method of embodiment 26, wherein the extractant is selected from the group consisting of glyceryl tributyrate, glyceryl tripropionate, oleyl alcohol, polypropylene glycol, and any combination thereof.
29. The method of any one of embodiments 1 to 28, wherein the fermentation product mixture has less than 5 wt % water.
30. The method of any one of embodiments 1 to 29, wherein the base is selected from the group consisting of $K_3PO_4$, KOH, $Ba(OH)_2 \cdot 8H_2O$, $K_2CO_3$, KOAc, $KH_2PO_4$, $Na_2HPO_4$, pyridine, $Et_3N$, and any combinations thereof.
31. The method of any one of embodiments 1 to 30, wherein the metal catalyst comprises one or more metals.
32. The method of embodiment 31, wherein one or more of the metals is a transition metal.
33. The method of embodiment 31 or 32, wherein one or more of the metals is a late transition metal.
34. The method of any one of embodiments 31 to 33, wherein one or more of the metals is selected from the group consisting of palladium, platinum, nickel, ruthenium, rhodium, rhenium, iridium, iron, copper, and cobalt.
35. The method of any one of embodiments 1 to 34, wherein the metal catalyst is selected from the group consisting of

[Ir(COD)Cl]$_2$, RuCl$_2$(COD), PtCl$_2$(COD), [Rh(COD)Cl]$_2$, Ni/Si-Alumina, Ru/C, Rh/C, Pt/C, Pd/C, and any combination thereof.

36. The method of any one of embodiments 1 to 35, wherein the base is selected from the group consisting of K$_3$PO$_4$, KOH, Ba(OH)$_2$.8H$_2$O, K$_2$CO$_3$, KOAc, KH$_2$PO$_4$, Na$_2$HPO$_4$, pyridine, Et$_3$N, and any combinations thereof.

37. The method of any one of embodiments 1 to 36, wherein the metal catalyst is basic.

38. The method of embodiment 37, wherein one or more of the metals is a transition metal.

39. The method of embodiment 38, wherein one or more of the metals is a late transition metal.

40. The method of embodiment 39, wherein one or more of the metals is selected from the group consisting of palladium, platinum, nickel, ruthenium, rhodium, rhenium, iridium, iron, copper, and cobalt.

41. The method of any one of embodiments 1 to 40, wherein the metal catalyst further comprises a support.

42. The method of embodiment 41, wherein the support is selected from the group consisting of hydrotalcite, single component metal oxides, alkaline earth oxides, alkali metal oxides, rare earth oxides, ThO$_2$, MgO, Na doped MgO, SrO, BaO, CaO, ZnO, La$_2$O$_3$, TiO$_2$, ZrO$_2$, Al$_2$O$_3$, hydroxyapatite, fluorapatite, tert-butoxyapatite, sepiolite, basic zeolites, alkali ion-exchanged zeolites, alkali ion-added zeolites, Pd/NaY zeolite, Pd/NH$_4$-β zeolite, supported alkali metal ions, alkali metal ions on alumina, alkali metal ions on silica, alkali metal on alkaline earth oxide, alkali metals and alkali metal hydroxides on alumina, metal/SiO$_2$, Na/SiO$_2$Pd/Na/SiO$_2$, Na/Ca/SiO$_2$, Na/Ca/SiO$_2$, Cs/SiO$_2$, metal-supported zeolite, potassium oxide supported on zeolite Y, synthetic chrysotiles, Mg$_3$(OH)$_4$Si$_4$O$_5$, cobalt(II)-substituted chrysotile, amino-functionalized mesoporous silica, amino-functionalized MCM-41, alkali ion-exchanged mesoporous silica, alkali ion-exchanged SBA-15, ionic liquid supported MgO, amorphous aluminophosphate, synthetic talcs, magnesium organo silicates, KF supported on alumina, lanthanide imide on zeolite, and lanthanide nitride on zeolite.

43. The method of embodiment 42, wherein the support is hydrotalcite.

44. The method of any one of embodiments 1 to 43, wherein the metal catalyst is ruthenium hydrotalcite, palladium hydrotalcite, or copper hydrotalcite.

45. The method of any one of embodiments 1 to 44, wherein the metal catalyst has base site density of at least 10 micromoles/gram of catalyst.

46. The method of embodiment 45, wherein the metal catalyst has base site density of at least 50 micromoles/gram of catalyst.

47. The method of any one of embodiments 1 to 46, wherein the alcohols are contacted with the metal catalyst and optionally the base at an operating temperature range of between 100° C. to 350° C. to produce the mixture of hydrocarbon ketones.

48. The method of any one of embodiments 1 to 47, wherein the alcohols are contacted with the metal catalyst and optionally the base at an operating pressure of between 1 atm and 60 atm to produce the mixture of hydrocarbon ketones.

49. A method of producing a mixture of hydrocarbon ketones, comprising:
a) contacting biomass or sugars with a fermentation host to produce a fermentation product mixture, wherein the fermentation product mixture comprises isopropanol, butanol and ethanol;
b) isolating at least a portion of the isopropanol, butanol and ethanol from the fermentation product mixture; and
c) contacting the isolated isopropanol, butanol and ethanol with metal catalyst and optionally base to produce a mixture of hydrocarbon ketones.

50. A method of producing a mixture of hydrocarbon ketones, comprising:
a) contacting biomass or sugars with a fermentation host to produce a fermentation product mixture, wherein the fermentation product mixture comprises acetone, butanol and ethanol;
b) isolating at least a portion of the acetone, butanol and ethanol from the fermentation product mixture; and
c) contacting the isolated acetone, butanol and ethanol with metal catalyst and optionally base to produce a mixture of hydrocarbon ketones, wherein at least 20% of the mixture of hydrocarbon ketones are C$_{7+}$ hydrocarbon ketones.

51. The method of embodiment 49 or 50, wherein at least 70% of the mixture of hydrocarbon ketones are C$_{7+}$ hydrocarbon ketones.

52. The method of embodiment 49 or 50, wherein at least 40% of the mixture of hydrocarbon ketones are C$_{11+}$ hydrocarbon ketones.

53. The method of any one of embodiments 1 to 52, further comprising separating one or more intermediates from the mixture of hydrocarbon ketones to form a recycled reactant stream and contacting the recycled reactant stream with the metal catalyst and optionally base.

54. The method of embodiment 53, wherein the one or more intermediates is selected from the group consisting of 2-pentanone, 2-heptanone, 4-heptanone, and mixtures thereof.

55. A method of producing a mixture of hydrocarbon ketones, comprising contacting at least two or more alcohols with metal catalyst and optionally base to produce a mixture of hydrocarbon ketones, wherein at least one of the two or more alcohols is an acetone precursor.

56. The method of embodiment 55, wherein the acetone precursor is glycerol.

57. The method of any one of embodiments 1 to 55, wherein the metal catalyst comprises two or more metals.

58. The method of embodiment 57, wherein the two or more metals are Pd and Cu.

59. The method of embodiment 58, wherein the molar ratio of Pd:Cu is 2:1.

60. The method of any one of embodiments 57 to 59, wherein the metal catalyst comprising two or more metals forms C$_5$-C$_{11}$ ketones at a rate 2.5 times the rate of formation of C$_5$-C$_{11}$ ketones by metal catalyst comprising one of the two or more metals.

61. The method of any one of embodiments 57 to 59, wherein the metal catalyst comprising two or more metals forms C$_5$-C$_{11}$ ketones at a rate 5.6 times the rate of formation of C$_5$-C$_{11}$ ketones by metal catalyst comprising one of the two or more metals.

62. The method of any one of embodiments 57 to 59, wherein the metal catalyst comprising two or more metals forms C$_{11+}$ ketones at a rate 33 times the rate of formation of C$_{11+}$ ketones by metal catalyst comprising one of the two or more metals.

63. A method of producing a mixture of hydrocarbon ketones, comprising contacting acetone and at least two or more primary alcohols with catalyst and optionally base to produce a mixture of hydrocarbon ketones, wherein the catalyst comprises hydrotalcite (HT) and one or more metals.

64. The method of embodiment 63, wherein the one or more metals are coprecipitated or impregnated on the HT.
65. The method of embodiment 63, wherein the HT is coprecipitated or impregnated on carbon to form a support, and the one or more metals are coprecipitated or impregnated on the support.
66. The method of embodiment 63, wherein the HT is mixed with carbon to form a support, and the one or more metals are coprecipitated or impregnated on the support.
67. The method of any one of embodiments 63 to 66, wherein the one or more metals are two or more metals.
68. A method of producing a mixture of hydrocarbon ketones, comprising contacting acetone and at least two or more primary alcohols with catalyst and optionally base to produce a mixture of hydrocarbon ketones,
wherein the catalyst comprises $La_2O_3$ and one or more metals.
69. The method of embodiment 68, wherein the one or more metals are coprecipitated or impregnated on the $La_2O_3$.
70. The method of embodiment 68, wherein the $La_2O_3$ is coprecipitated or impregnated on carbon to form a support, and the one or more metals are coprecipitated or impregnated on the support.
71. The method of embodiment 68, wherein the $La_2O_3$ is mixed with carbon to form a support, and the one or more metals are coprecipitated or impregnated on the support.
72. The method of any one of embodiments 63 to 71, wherein the catalyst further comprises $TiO_2$.
73. A method of producing a mixture of hydrocarbon ketones, comprising contacting acetone and at least two or more primary alcohols with catalyst and optionally base to produce a mixture of hydrocarbon ketones,
wherein the catalyst comprises $TiO_2$ and one or more metals.
74. The method of embodiment 73, wherein the one or more metals are coprecipitated or impregnated on the $TiO_2$.
75. The method of embodiment 73, wherein the $TiO_2$ is coprecipitated or impregnated on carbon to form a support, and the one or more metals are coprecipitated or impregnated on the support.
76. The method of embodiment 73, wherein the $TiO_2$ is mixed with carbon to form a support, and the one or more metals are coprecipitated or impregnated on the support.
77. A method of producing a mixture of hydrocarbon ketones, comprising contacting acetone and at least two or more primary alcohols with catalyst and optionally base to produce a mixture of hydrocarbon ketones,
wherein the catalyst comprises MgO and one or more metals.
78. The method of embodiment 77, wherein the one or more metals are coprecipitated or impregnated on the MgO.
79. The method of embodiment 77, wherein the MgO is coprecipitated or impregnated on carbon to form a support, and the one or more metals are coprecipitated or impregnated on the support.
80. The method of embodiment 77, wherein the MgO is mixed with carbon to form a support, and the one or more metals are coprecipitated or impregnated on the support.
81. A method of producing a mixture of hydrocarbon ketones, comprising contacting acetone and at least two or more primary alcohols with catalyst and optionally base to produce a mixture of hydrocarbon ketones,
wherein the catalyst comprises Pd—Cu/HT, Pd—Cu/HT-C, Pd—Cu/HT/C, Pd/HT, Cu/HT, Cu/ZnO/$Al_2O_3$, hydroxyapatite, perovskite, Cu/MgO, (Cu/ZnO/$Al_2O_3$)/HT, BaO/$SiO_2$, MgO/$SiO_2$, SrO/$SiO_2$, CaO/$SiO_2$, SrO/MgO, CaO/MgO, Pd—Cu/NiHT, Cu/NiHT, PdCu/ZnHT, Cu/ZnHT, PdCu/ZnHT, Ru/HT, Cu—Ru/HT, Co/HT, Pt/HT, Pt—Cu/HT, Cu/$SiO_2$, Pd/C, CaO/C, SrO/C, BaO/C, $La_2O_3$/C, $CeO_2$/C, HT/C, HT, $CeO_2$, $La_2O_3$, $TiO_2$, or zeolite, or any combinations thereof.
82. A method of producing a mixture of hydrocarbon ketones, comprising contacting acetone and at least two or more primary alcohols with catalyst and optionally base to produce a mixture of hydrocarbon ketones,
wherein the catalyst comprises:
Pd—Cu/HT;
Pd—Cu/HT and zeolite;
Pd—Cu/HT and $TiO_2$;
Pd—Cu/HT-C and $TiO_2$;
Pd-HT;
Cu-HT;
Pd/HT-C;
Pd—Cu/HT-C;
Cu/ZnO/$Al_2O_3$ and hydroxyapatite;
Cu/ZnO/$Al_2O_3$ and perovskite;
Cu/MgO;
Cu/ZnO/$Al_2O_3$ and HT;
Cu/ZnO/$Al_2O_3$ and BaO/$SiO_2$;
Cu/ZnO/$Al_2O_3$ and MgO/$SiO_2$;
Cu/ZnO/$Al_2O_3$ and SrO/$SiO_2$;
Cu/ZnO/$Al_2O_3$ and CaO/$SiO_2$;
Cu/ZnO/$Al_2O_3$ and SrO/MgO;
Cu/ZnO/$Al_2O_3$ and CaO/MgO;
Cu/$SiO_2$ and CaO/MgO;
PdCu—CaO/MgO;
PdCu-NiHT;
Cu-NiHT;
PdCu—ZnHT;
Cu—ZnHT;
RuHT;
Cu—Ru/HT;
CoHT;
PtHT;
PtCuHT;
Cu/$SiO_2$, Pd/C and CaO/C;
Cu/$SiO_2$, Pd/C and SrO/C;
Cu/$SiO_2$, Pd/C and BaO/C;
Cu/$SiO_2$, Pd/C and $La_2O_3$/C;
Cu/$SiO_2$, Pd/C and $CeO_2$/C;
Cu/$SiO_2$, Pd/C and HT/C;
Cu/$SiO_2$, Pd/C and HT;
Cu/ZnO/$Al_2O_3$, Pd/C and HT;
Cu/ZnO/$Al_2O_3$ and $CeO_2$;
Cu/ZnO/$Al_2O_3$, Pd/C and $CeO_2$;
Cu/ZnO/$Al_2O_3$ and $La_2O_3$;
Cu/ZnO/$Al_2O_3$, Pd/C and $La_2O_3$;
Cu/ZnO/$Al_2O_3$, Pd/C, $La_2O_3$, and $TiO_2$;
Cu/ZnO/$Al_2O_3$, Pd/C, and $CeO_2$;
Cu/ZnO/$Al_2O_3$, Pd/C, $CeO_2$, and $TiO_2$,
Pd—Cu/ZnO/HT;
Cu/ZnO/HT;
Cu/ZnO/$Al_2O_3$ and MgO;
Cu/ZnO/$Al_2O_3$, Pd/C and MgO; or
Cu/ZnO/$Al_2O_3$, Pd/C, MgO, and $TiO_2$.
83. The method of embodiment 82, wherein the catalyst comprises:
Pd—Cu/HT;
Pd—Cu/HT-C;
Pd—Cu/HT and $TiO_2$; or
Pd—Cu/HT-C and $TiO_2$.
84. The method of any one of embodiments 63 to 83, wherein the two or more primary alcohols are two or $C_{1-20}$ alcohols.

85. The method of any one of embodiments 63 to 83, wherein the two or more primary alcohols are butanol and ethanol.
86. The method of any one of embodiments 63 to 83, wherein the two or more primary alcohols are butanol and 2-ethylhexanol.
87. The method of any one of embodiments 63 to 86, wherein at least 40% of the mixture of hydrocarbon ketones are $C_{11+}$ hydrocarbon ketones.
88. The method of any one of embodiments 1 to 62, wherein the catalyst comprises hydrotalcite (HT) and one or more metals.
89. The method of embodiment 88, wherein the one or more metals are coprecipitated or impregnated on the HT.
90. The method of embodiment 88, wherein the HT is coprecipitated or impregnated on carbon to form a support, and the one or more metals are coprecipitated or impregnated on the support.
91. The method of embodiment 88, wherein the HT is mixed with carbon to form a support, and the one or more metals are coprecipitated or impregnated on the support.
92. The method of any one of embodiments 88 to 91, wherein the one or more metals are two or more metals.
93. The method of any one of embodiments 63 to 92, wherein the one or more metals are selected from the group consisting of Pd, Cu, Ni, Zn, Ru, Co, and Pt.
94. One or more hydrocarbon ketones produced according to any one of embodiments 1 to 93.
95. A composition comprising:
a gasoline fuel, a jet fuel, a diesel fuel, or any mixtures thereof; and
one or more hydrocarbon ketones produced according to any one of embodiments 1 to 93.

EXAMPLES

The following Examples are merely illustrative and are not meant to limit any aspects of the present disclosure in any way.

All the metal sources were purchased from either Sigma Aldrich or Strem Chemicals and used as received. Chemicals were obtained from Sigma Aldrich and used without further purification.

All the reactions were analyzed by gas chromatography using dodecane as internal standard. Gas chromatography analysis was performed on a Varian CP-3800 instrument with a FID detector and VF-5 MS column (5% phenyl and 95% methylpolysiloxane) using helium as the carrier gas.

Example 1

ABE Reaction Using Metal/Hydrotalcite Catalyst

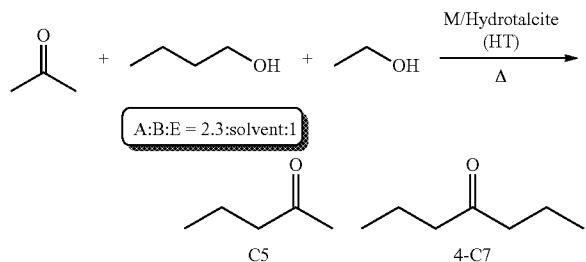

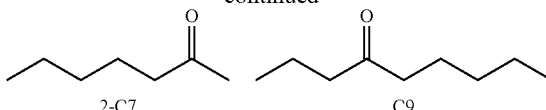

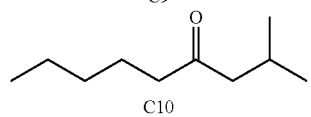

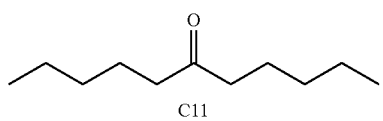

This Example demonstrates the production of a mixture of alkanones from an acetone-butanol-ethanol (ABE) starting mixture using a metal/hydrotalcite catalyst.

Catalyst Preparation

The metal/hydrotalcite catalysts used in this Example were prepared according to the following procedures.

0.5 wt % Palladium/Hydrotalcite: A 250 mL round bottom flask was charged with commercially available hydrotalcite (5 g) palladium chloride (0.96 mmol, 0.17 g) and potassium chloride (0.25 g). Water (130 mL) was added and the resulting suspension was stirred at room temperature for 1 hour. The reaction mixture was then lowered in a preheated oil bath and was stirred at 100° C. under hydrogen atmosphere overnight. The reaction mixture was filtered and the solid was washed with copious amounts of water. The grey solid was dried under vacuo at 120° C. for 4 hours.

3.2 wt % Copper-Hydrotalcite: A 250 mL round bottom flask was charged with commercially available hydrotalcite (5 g) and copper acetate (11 mmol, 2 g). Water (130 mL) was added and the resulting suspension was stirred at 60° C. for 14 hours. The reaction mixture was filtered and the solid was washed with copious amounts of water. The solid was dried under vacuo at 120° C. for 4 hours. The copper loading on hydrotalcite was determined using ICP analysis.

Method

In a 12 mL Q-tube containing a stir bar, 3.2 wt % Cu/HT or 0.5 wt % Pd/HT was charged to the reaction vessel. To the reaction mixture, acetone, butanol, and ethanol were sequentially added to the reaction vessel. The amount of acetone, butanol, ethanol and catalyst used is specified in Table 1 below. Toluene as a solvent was also added to the reaction vessel, as specified in Table 1 below.

The Q-tube was sealed and the reaction mixture was stirred for 24 hours at 240° C. in a pre-heated metal block. The reaction mixture was cooled to room temperature and dodecane (internal standard) was added. The reaction mixture was diluted with tetrahydrofuran and the GC analysis of the reaction mixture was carried out.

The results from each reaction are summarized in Table 1 below.

TABLE 1

| Entry[a] | Catalyst (mol %) | Temp (° C.) | C5 (%) | 4-C7 (%) | 2-C7 (%) | C9 (%) | C10 (%) | C11 (%) | Alcohols | Yield (%) |
|---|---|---|---|---|---|---|---|---|---|---|
| 1 | Ru/HT (0.3)[b] | 200 | 0.4 | 2.2 | 12.9 | 0.6 | 0.2 | 3.4 | — | 20 |
| 2 | Pd/HT (0.15)[b] | " | 0.1 | 1.3 | 17.6 | 0.6 | 0 | 11.9 | — | 32 |
| 3 | Pd/HT (0.15) | " | 0 | 0 | 39.6 | 1.8 | 0 | 16.8 | — | 58 |
| 4 | Pd/HT (0.3) | 240 | 12.1 | 4.4 | 38.2 | 7.3 | 1.6 | 29.5 | 2.0 | 95 |
| 5 | Cu/HT (0.8) | 240 | 1.5 | 4.4 | 31.4 | 2.4 | 0.1 | 28.4 | 23.8 | 92 |

[a]Acetone (2.3 mmol), Butanol (2 mL), Ethanol (1 mmol), 24 hours, catalyst loading is represented as molar percentages with respect to total alcohol loading (ethanol + 1-butanol). Yield based on acetone determined by calibrated internal standard (n-dodecane).
[b]Acetone (2.3 mmol), Butanol (3.7 mmol), Ethanol (1 mmol), Toluene (1 mL).

Treatment of mixture of ABE in toluene to catalytic Ru/HT at 200° C. was observed to produce hydrocarbon ketones in 20% yield (entry 1). Switching to Pd/HT resulted in some improvements in the yield (comparing entries 1 vs 2). Replacing toluene with butanol as the solvent increased the overall yield of hydrocarbon ketones to 58% (entry 3). Complete conversion of acetone was observed at 230° C., which also mirrored high yields for hydrocarbon ketones (entry 4). Substituting palladium with Cu(II)/HT in the ABE alkylation reaction provided mixture of hydrocarbon ketones along with the corresponding mixture of reduced alcohols in 92% overall yield (entry 5).

Example 2

Effect on Water on ABE Reaction

This Example demonstrates the effect of water on the alkylation reaction of an ABE mixture. The reaction was performed according to the procedure described in Example 1 above, using the following acetone (2.3 mmol), butanol (2 mL), ethanol, (1 mmol), 3.2 wt % Cu/HT (0.8 mol %), $H_2O$ (wt %) at 240° C. for 24 hours. Different weight percentages of water with respect to the total weight of ABE used in the reaction was added to the reaction mixture.

The product yield for each hydrocarbon ketone observed and the overall yield was determined and summarized in FIG. 1. Yields were calculated based on acetone. The alkylation reaction with Cu-HT was observed to tolerate up to 0.5 wt % water. Further increasing water content was observed to slow down the ABE reaction, which resulted in a decrease in yield of dialkylated ketones as well as the overall yield in the ABE reaction.

Example 3

Recycling Experiments

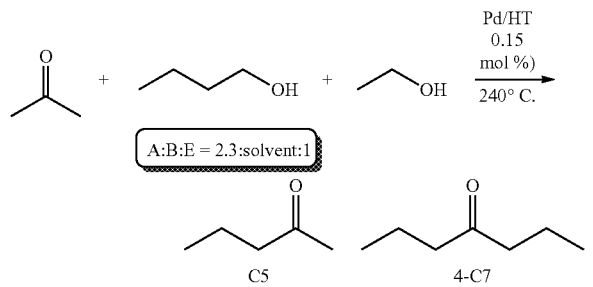

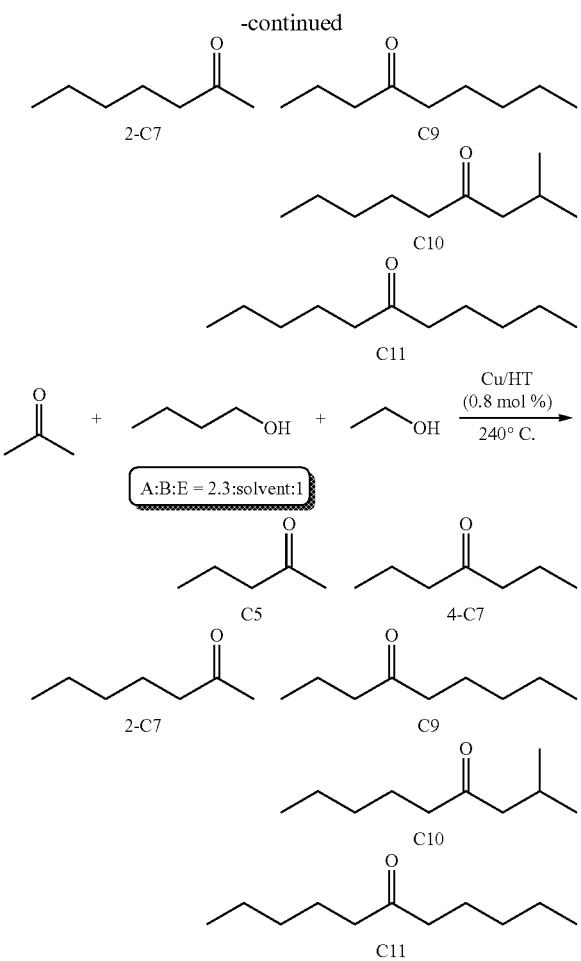

This Example demonstrates the reusability of Pd/HT and Cu/HT. 0.5 wt % Pd/HT (0.15 mol %) or 3.2 wt % Cu/HT (0.8 mol %) were reacted with acetone (2.3 mmol), butanol (2 mL), and ethanol (1 mmol) at 240° C. for 24 hours according to the procedure described in Example 1 above. The catalysts were subsequently separated from their liquid supernatant by centrifugation. The supernatants were removed and the catalysts dried and washed with ethanol before applying the respective catalysts to another cycle of acetone alkylation.

Table 2 summarizes the results of the Pd/HT recycling experiments. Table 3 summarizes the results of the Cu/HT recycling experiments. Yields are based on acetone. The products as identified as follows: A=C5; B=4-C7; C=2-C7; D=C9; E=C10; F=C11.

TABLE 2

| Entry | A (%) | B (%) | C (%) | D (%) | E (%) | F (%) | Yield (%) |
|---|---|---|---|---|---|---|---|
| Cycle 1 | 0.1 | 36.4 | 3.2 | 2.5 | 0.1 | 25.3 | 68 |
| Cycle 2 | 0.2 | 40.6 | 2.6 | 1.4 | 0.1 | 15 | 60 |
| Cycle 3 | 0.1 | 18.2 | 8.8 | 2.9 | 0 | 36.8 | 67 |

TABLE 3

| Entry | A (%) | B (%) | C (%) | D (%) | E (%) | F (%) | Alcohols (%) | Yield (%) |
|---|---|---|---|---|---|---|---|---|
| Cycle 1 | 1.5 | 4.4 | 31.4 | 2.4 | 0.1 | 28.4 | 23.8 | 92 |
| Cycle 2 | 0.1 | 5.8 | 31.9 | 3.1 | 0.5 | 30.0 | 14.4 | 86 |
| Cycle 3 | 0.2 | 6.3 | 33.6 | 2.9 | 0.5 | 28.2 | 12.7 | 84 |

Example 4

Catalyst Characterization

Figure 2:
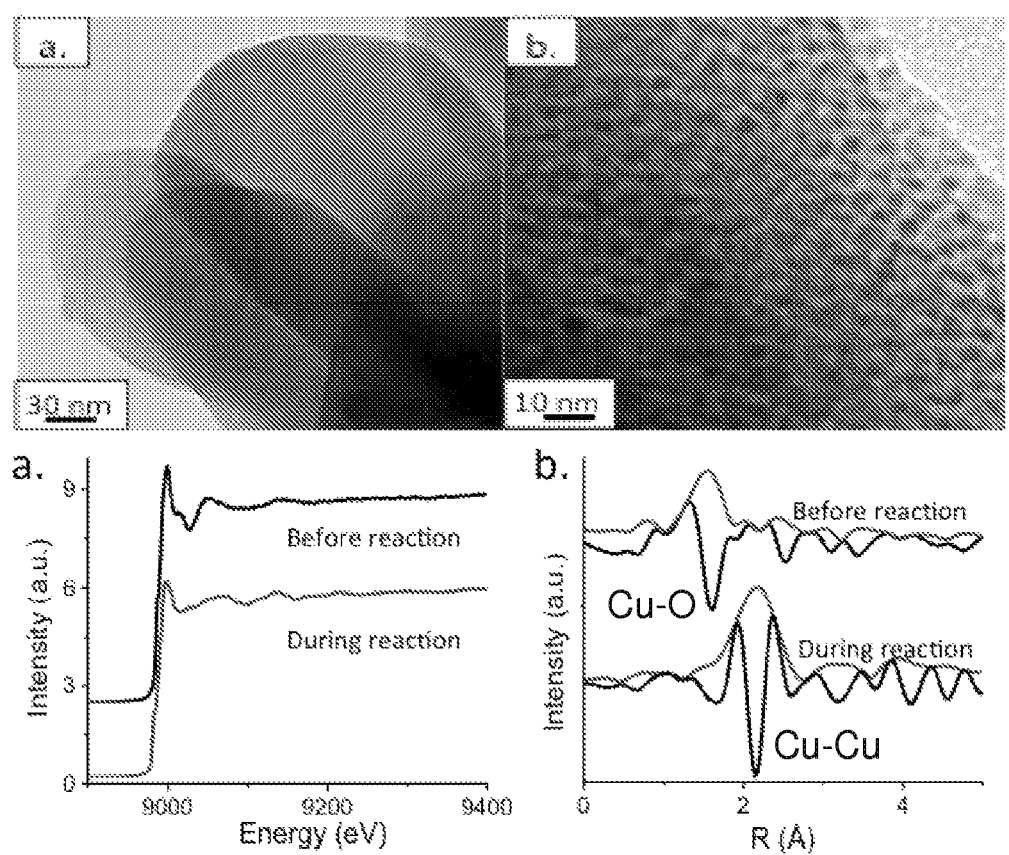
FIG. 2 depicts (i) HR-TEM images of 3.2 wt % Cu/HT; (ii)(a) EXAFS analysis of Cu/HT before the reaction and in situ; (ii)(b) Cu/HT in R space indicating the reduction of Cu (II) to Cu (0) under the ABE reaction.
Figure 3:
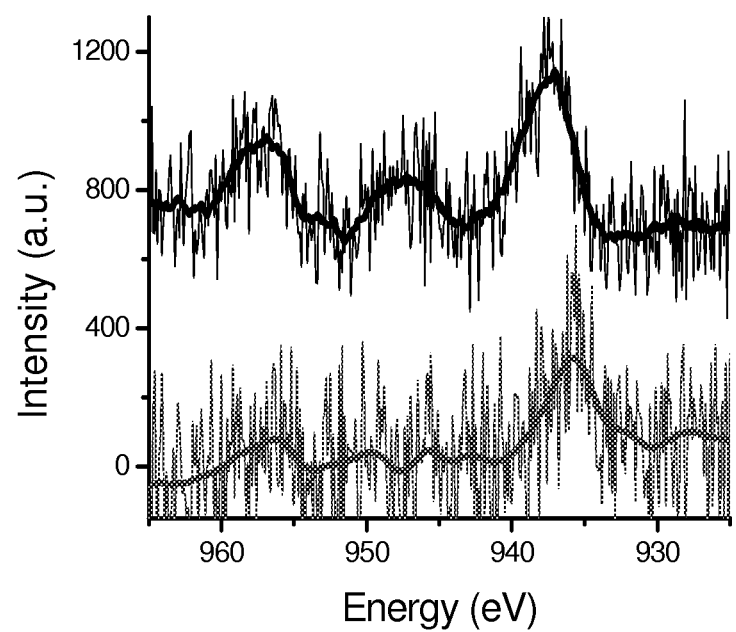
FIG. 3 is an XPS spectra of 3.2 wt % Cu/HT before (top line) and after (bottom line) the reaction. The study indicates reduction of Cu(II) to metallic Cu(0).

This Example demonstrates the characterization of the Cu/HT used in Example 1 above. Standard techniques were used to characterize the catalyst to evaluate the activity of Cu/HT.
Cu/HT was prepared according to the procedure in Example 1 above. The high-resolution transmission electron microscope (HR-TEM) images of Cu/HT catalyst were obtained, and indicated the formation of Cu clusters with diameter of 2±1 nm loaded on 150±50 nm HT support (FIG. 2). The clusters were analyzed by extended x-ray absorption fine structures (EXAFS) and x-ray photoelectron spectroscopy (XPS). The x-ray absorption measurements showed that CuO is the main species in the heterogeneous Cu/HT catalyst. Similar results were obtained by XPS measurements (FIG. 3). In-situ EXAFS measurements showed that CuO was reduced to Cu(0) at 250° C. under continuous flow of the ABE mixture, prior to the formation of products (FIG. 2). These results demonstrate that the copper nanoparticles are the active catalytic species involved in the dehydrogenation of alcohols to produce aldehydes, which undergoes aldol condensation with acetone during the ABE reaction.

Example 5

Temperature Programmable Desorption Study

Figure 4:
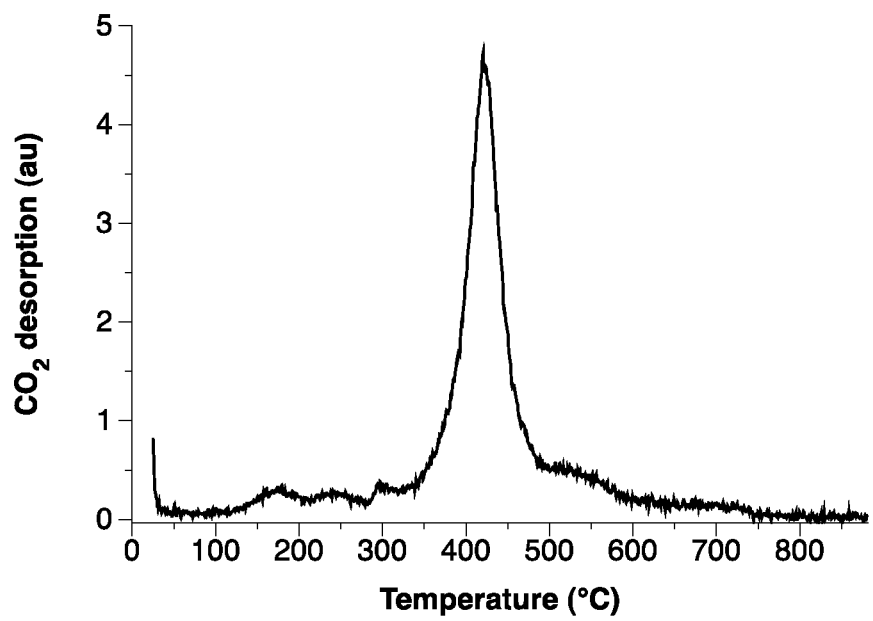
FIG. 4 is a TPD analysis of 3.2 wt % Cu/HT.

Temperature desorption studies (TPD) was used to determine the surface basicity of Cu/HT. Cu/HT was prepared according to the procedure in Example 1 above. The catalyst was treated under a stream of $CO_2$ at ambient temperature and pressure for 30 minutes after which the pretreated sample was placed in a Netzsch TGA-MS and heated to 900° C. at a ramp rate of 5° C./min, while monitoring the weight of the sample and the total ion current from the gas stream. Maximum $CO_2$ desorption was seen at 419° C. in the TBD profile (FIG. 4).

Example 6

Synthesis of Jet and Diesel Range Compounds ($C_7$-$C_{19}$) Using Cu-HT

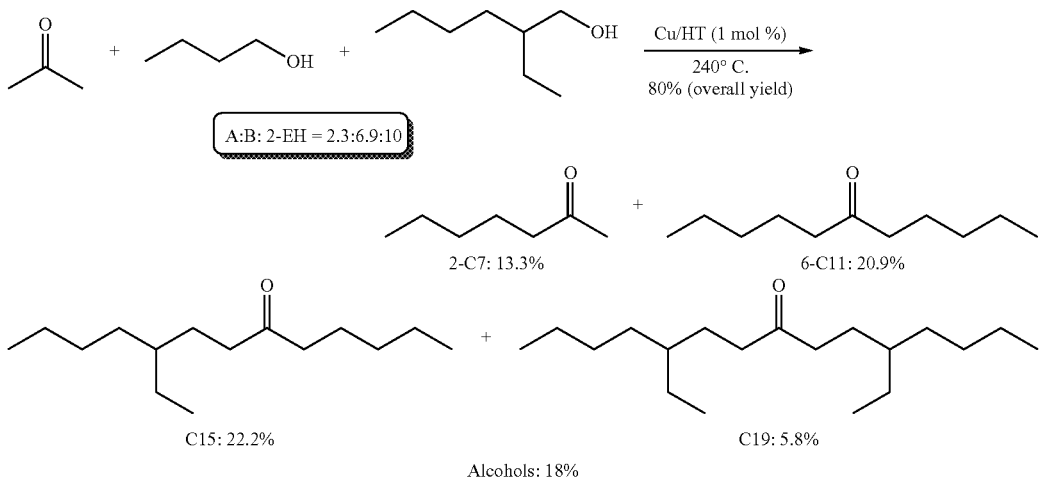

In a 12 mL Q-tube containing a stir bar, 3.2 wt % Cu/HT (0.350 g) was charged. The Cu/HT used was prepared according to the procedure in Example 1 above. To the reaction mixture, acetone (0.134 g, 2.3 mmol), 2-ethyl-1-hexanol (1.3 g, 10 mmol), butanol (0.51 g, 6.9 mmol) were sequentially added. The Q-tube was sealed and the reaction mixture was stirred for 24 hours at 240° C. in a pre-heated metal block. The reaction mixture was cooled to room temperature and dodecane (internal standard) was added. The reaction mixture was diluted with tetrahydrofuran and the GC analysis of the reaction mixture was carried out. The yields of the alkanone product mixture are described in the reaction scheme above. Yields based on acetone.

Example 7

Synthesis of Jet and Diesel Range Compounds (C$_7$-C$_{19}$) Using Pd/C and K$_3$PO$_4$

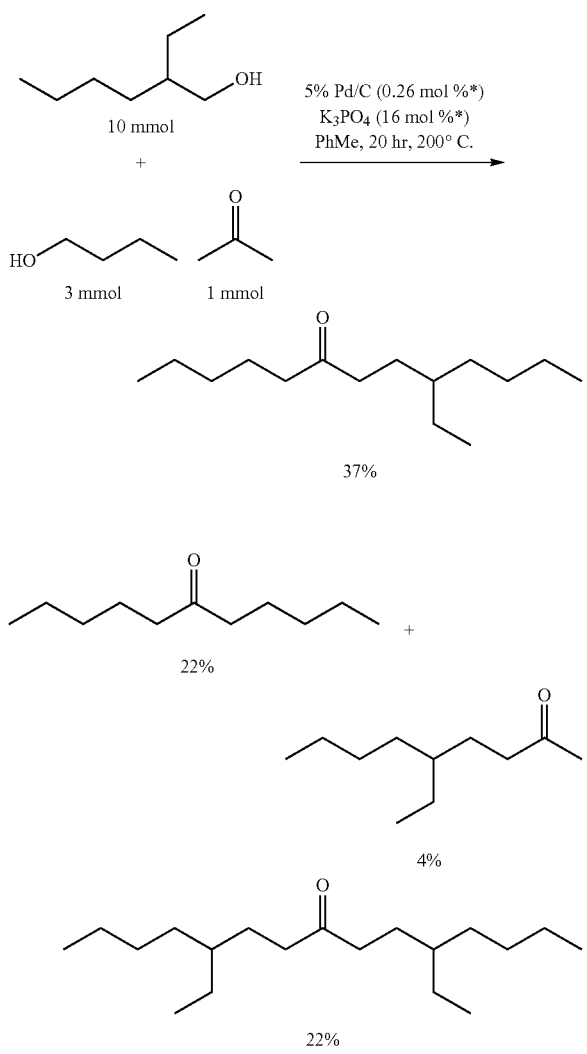

In a 12 mL Q-tube containing a stir bar, Pd/C catalyst and K$_3$PO$_4$ was charged. To the reaction mixture, 2-ethyl-1-hexanol (10 mmol), butanol (3 mmol), and acetone (1 mmol) and toluene as a solvent were added. The Q-tube was sealed and the reaction mixture was stirred for 20 hours at 200° C. in a pre-heated metal block. The reaction mixture was cooled to room temperature and dodecane (internal standard) was added. The reaction mixture was diluted with tetrahydrofuran and the GC analysis of the reaction mixture was carried out. The yields of the alkanone product mixture are described in the reaction scheme above. Yields based on acetone.

Example 8

IBE Reaction Time Course Study Using Metal/Hydrotalcite Catalyst

Figure 5:
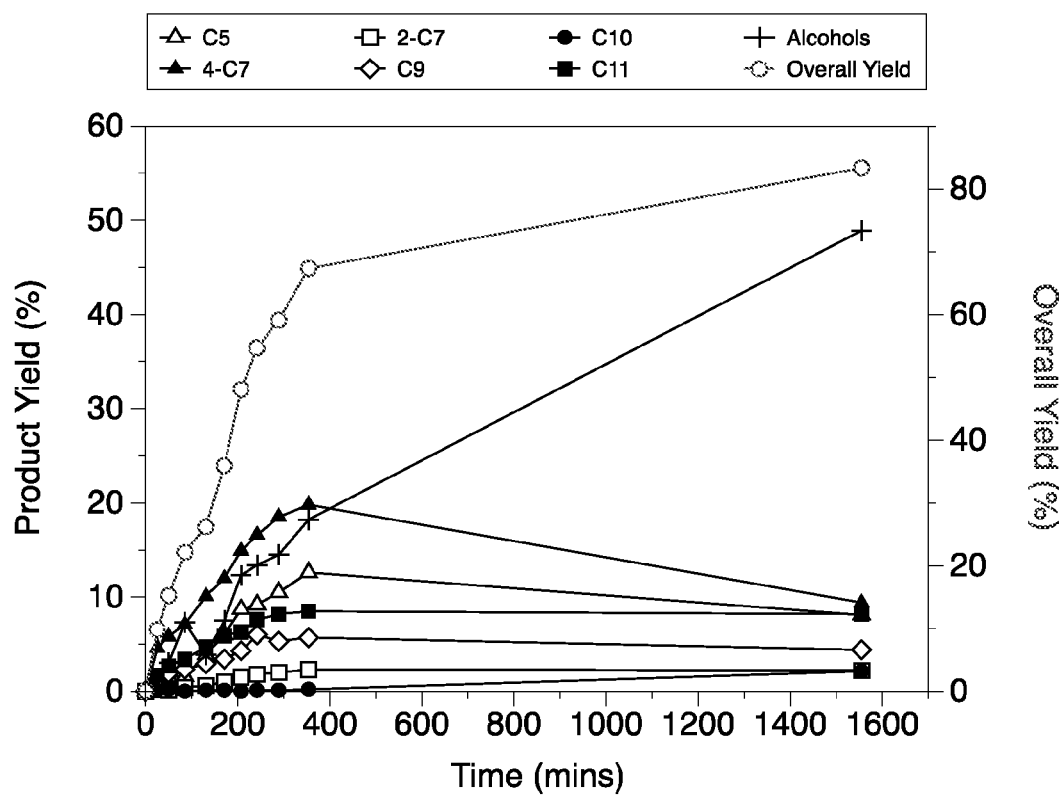
FIG. 5 is a graph depicting the product and overall yields of various alkanones produced in an IBE reaction over time.

A time course study for the IBE reaction was performed in a 4560 Mini Parr reactor. Acetone and isopropanol concentration was determined using calibrated internal standard (dodecane) in the GC-MS. 3.2 wt % Cu/HT (0.8 mol %) was reacted with isopropanol (11.5 mmol) butanol (10 mL), and ethanol (5 mmol) at 275° C. for 24 hours according to the procedure described in Example 1. Samples at different time intervals were dispensed using an attached sample collection vessel and was analyzed using gas chromatography. The results of this time course study are summarized in FIG. 5. All yields were based on isopropanol. The ratio of isopropanol converted to acetone in situ was also monitored during this time course study, and the results are summarized in Table 4 below.

TABLE 4

| Entry | Time (mins) | IPA:Acetone |
|---|---|---|
| 1 | 25 | 4.0:1 |
| 2 | 50 | 3.0:1 |
| 3 | 131 | 2.4:1 |
| 4 | 171 | 2.4:1 |
| 5 | 207 | 1.9:1 |
| 6 | 1555 | 1.6:1 |

Example 9

ABE/IBE Reaction Using Metal/Hydrotalcite Catalyst

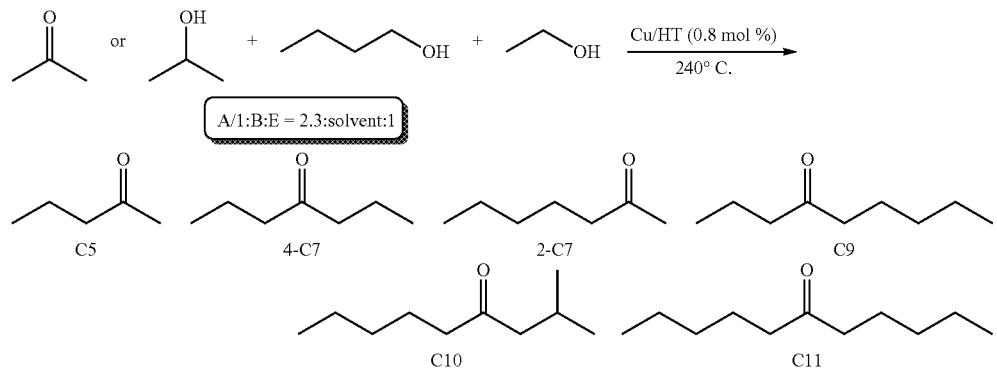

This Example compares the production of alkanones from an acetone-butanol-ethanol (ABE) and isopropanol-butanol-ethanol (IBE) starting mixture using a metal/hydrotalcite catalyst.

In a 12 mL Q-tube containing a stir bar, 0.8 wt % Cu/HT was charged to the reaction vessel. To the reaction mixture, acetone or isopropanol, butanol, and ethanol were sequentially added to the reaction vessel in the ratio specified in the reaction scheme above. The Q-tube was sealed and the reaction mixture was stirred for 24 hours at 240° C. in a pre-heated metal block. The reaction mixture was cooled to room temperature and dodecane (internal standard) was added. The reaction mixture was diluted with tetrahydrofuran and the GC analysis of the reaction mixture was carried out.

The results from each reaction are summarized in Table 5 below.

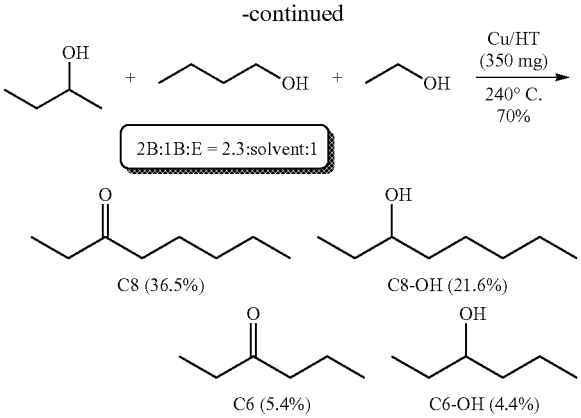

TABLE 5

| Entry | Reaction | C5 (%) | 4-C7 (%) | 2-C7 (%) | C9 (%) | C10 (%) | C11 (%) | Alcohols (%) | Yield (%) | C11+[a] (wt %) |
|---|---|---|---|---|---|---|---|---|---|---|
| 1 | ABE | 1.9 | 1.0 | 23.5 | 4.2 | 0.4 | 35.5 | 9.1 | 73 | 14 |
| 2 | BE | 0 | 1.9 | 24.0 | 1.9 | 0 | 21.8 | 11.1 | 61 | 25 |

[a]C11+ include mainly C13 and C15 and their isomers.

Figure 10:
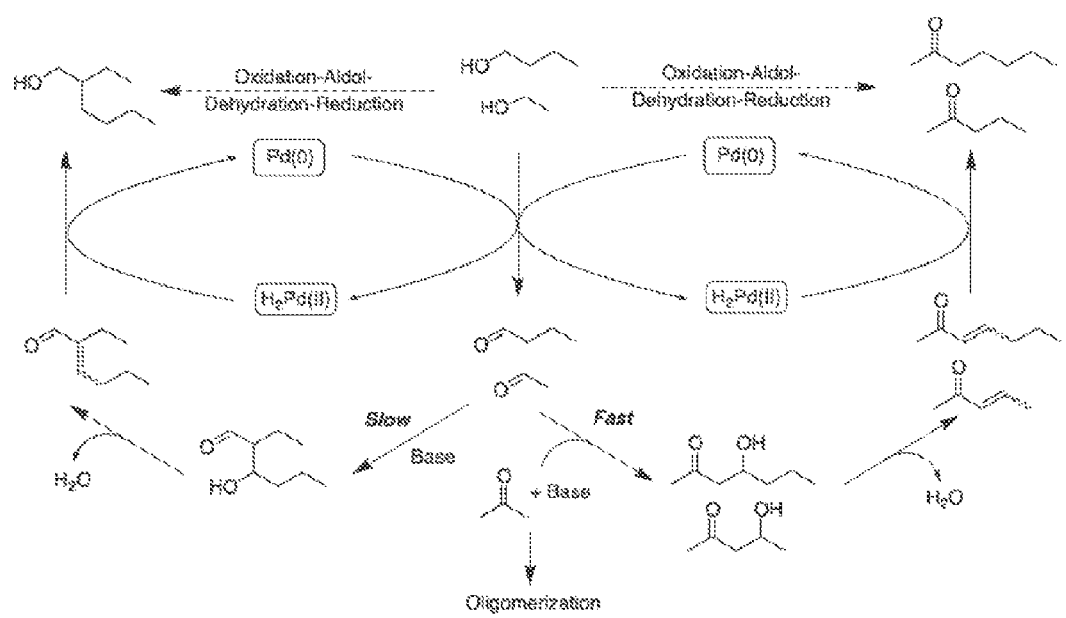
FIG. 10 depicts an exemplary reaction scheme for catalytic conversion of alcohols and ketones.

When IBE was used as the starting materials, without wishing to be bound by any theory, it is believed that $C_{11+}$ hydrocarbon ketones, such as $C_{13}$, $C_{15}$ and $C_{19}$ ketones, are produced from the alkylation reaction of 2-ethylhexanal with acetone or monoalkylated ketones formed in the reaction. 2-ethyl hexanal can be produced via dimerization reaction of butanal, which is a slow process compared to the alkylation reaction of acetone under our reaction conditions. See FIG. 10. It was unexpectedly observed that replacing acetone with isopropanol in the alkylation reaction increased the concentration of the 2-ethylhexanal, while the rate of aldol condensation between C2 and C4 aldehydes with the in situ formed acetone was observed to be decreased. This resulted in more $C_{11+}$ hydrocarbon ketones observed to be produced in the IBE reaction than the ABE reaction.

Example 10

Reactions Involving 2-Butanol and One or More Alcohols

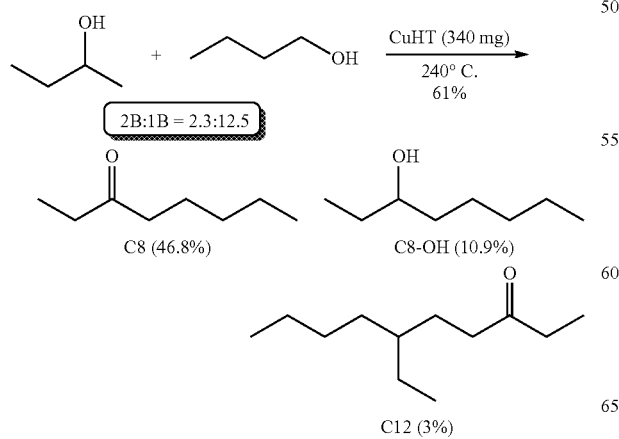

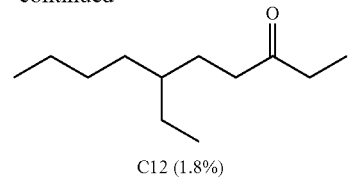

This Example demonstrates the production of a mixture of linear and branched alkanones using 2-butanol as the secondary alcohol and one or two primary alcohols, e.g., n-butanol and ethanol.

The two reactions depicted above were performed according to the methods described in Example 1 above. In the first reaction, 2-butanol (2.3 mmol) was reacted with n-butanol (12.5 mmol) in toluene (2 ml) in the presence of Cu/HT (340 mg) at 240° C. for 24 h. In the second reaction, 2-butanol (2.3 mmol) was reacted with ethanol (1 mmol) in n-butanol (2 ml) in the presence of Cu-HT (350 mg) at 240° C. for 24 h. The yields were calculated based on 2-butanol.

Example 11

IBE Fermentation

This Example demonstrates the production of IBE from fermentation of *C. acetobutylicum*.

Methods and Materials

Growth

*Clostridium acetobutylicum* was routinely stored and grown out of anaerobic −80 C. glycerol stocks. Cultures were grown in CGM:glucose (6%), yeast extract (5.0 gl$^{-1}$), ammonium acetate (2.0 gl$^{-1}$), NaCl (1.0 gl$^{-1}$), K$_2$HPO$_4$ (0.75 gl$^{-1}$), KH$_2$PO$_4$ (0.75 gl$^{-1}$), cysteine-HCl (0.5 gl$^{-1}$), MgSO$_4$.7H$_2$O (0.4 gl$^{-1}$), FeSO$_4$.7H$_2$O (0.04 gl$^{-1}$), MnSO$_4$.H$_2$O (0.02 gl$^{-1}$). Recombinant strains of *C. acetobutylicum* were supplemented with 80 mgl$^{-1}$ erythromycin. Recombinant *E. coli* strains were grown in Luria broth medium supplemented with the appropriate antibioitics carbenicillin (100 mgl$^{-1}$) and chloramphenicol (35 mgl$^{-1}$).

DNA Manipulation

All strains and plasmids used in this study are listed in Table 6 below. *E. coli* Top10 was used to propagate all plasmids before expression in *C. acetobutylicum* ATCC824. Methylation of all plasmids prior to transformation in ATCC824 was carried out with the pAN1 plasmid as previously described. See Mermelstein, L. D.; Papoutsakis, E. T. *Applied and environmental microbiology* 1993, 59, 1077-81.

TABLE 6

| Name (Restriction site) | Sequence | Target gene(s) |
| --- | --- | --- |
| ctfab fwd (BamHI) | AAAAAAGGATCCTTAAAAGGAGGGATT AAAATGAACTCTAAAATAATTAGATTT | ctfa/b |
| ace rev (SalI) | AAAAAGTCGACCTAAACAGCCATGGGTC TAAGTTCATTGGATATG | ctfa/b |
| adc rev (BamHI) | AAAAAAAGGATCCTATTTACTTAAGATAA TCATATATAACTTCAGCTCTAGGCAATAT | Adc |
| ace fwd (EcoRI) | AAAAAAGAATTCATAAAAACACCTCCAC ATAAGTTTATATAAATC | Adc |

The pIMP1 *Clostridium/E. coli* shuttle vector, generously provided by the Papoutsakis group, was used to construct all of the strains for this study. The construction of a synthetic acetone operon containing *C. acetobutylicum* adc_ctfa_ctfb genes was achieved as previously described. See Mermelstein, L. D.; Papoutsakis, E. T.; Petersen, D. J.; Bennett, G. N. *Biotechnology and bioengineering* 1993, 42, 1053-60. DNA fragments to construct this operon were PCR amplified from genomic DNA. Primers used and the restriction sites inserted in the operon can be found in Table 7 below. This operon was expressed under control of the native *C. acetobutylicum* adc promoter.

TABLE 7

| Name | Relevant features | Reference/Source |
| --- | --- | --- |
| Strains | | |
| *E. coli* XL1-Blue | recA1 endA1 gyrA96 thi-1 hsdR17 supE44 relA1 lac [F' proAB lacIqZΔM15 Tn10 (Tetr)] | Stratagene |
| *C. acetobutylicum* | Wild-type | ATCC |
| Plasmids | | |
| pIMP1 | Ap$^r$ MLS$^r$ repL, ColE1 origin | Papoutsakis[1] |
| pAN1 | Cm$^r$, φ3T I gene, p15A origin | Papoutsakis[1] |

TABLE 7-continued

| Name | Relevant features | Reference/Source |
| --- | --- | --- |
| pACE | pIMP1 derivative with adc-ctfAB (adc promoter) insertion | This study |
| pSADH | sadh (adc promoter and terminator) | GeneArt |
| pSACE | pACE derivative with sadh (adc promoter and terminator) insertion | This study |

The sequence for the sadh gene was identified from *C. beijerinkcii* strain B593 and synthesized by GeneArt® under the control of the *C. acetobutylicum* ATCC824 adc promoter and terminator. The synthesized SADH construct was cloned upstream of the synthetic acetone operon by restriction digest with SfoI/EcoRI followed by ligation to produce pSACE. The final construct sequence was verified before transformation into ATCC824. Transformation of the pSACE plasmid into *C. acetobutylicum* was performed by electroporation as previously described. Two days after transformation colonies were picked and PCR sequenced to verify the presence of the pSACE plasmid.

Figure 7A:
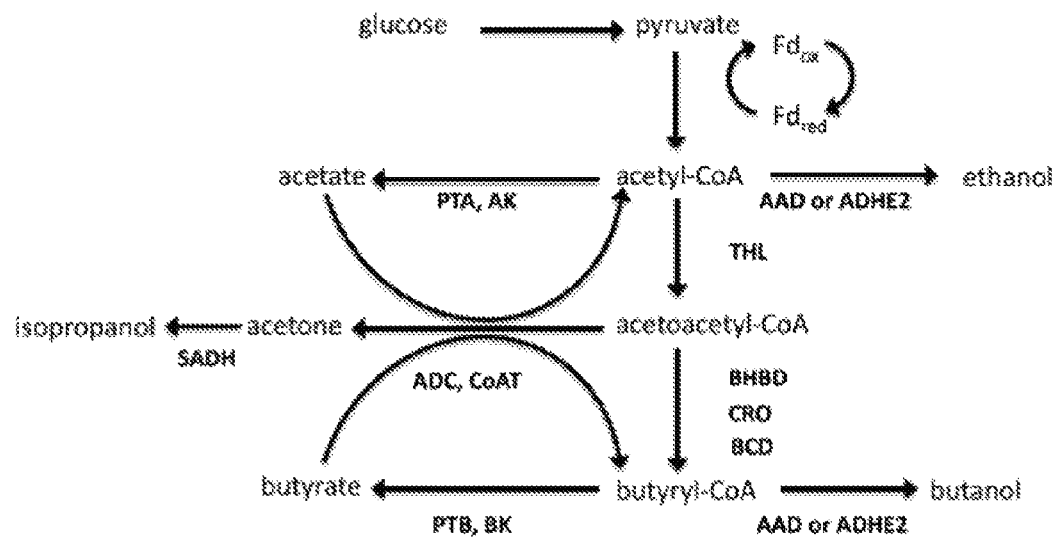
FIG. 7A is an exemplary scheme for production of IBE using Clostridia.
Figure 7B:
FIG. 7B is an exemplary scheme for the IBE production pathway in a recombinant Clostridia cell.

*Clostridium acetobutylicum* ATCC824 was transformed into an isopropanol, 1-butanol, ethanol production strain through expression of the secondary alcohol dehydrogenase from *Clostridium beijerinckii* strain B593 under the control of the acetoacetate decarboxylase promoter and terminator. Increased isopropanol production was achieved by overexpression of both the CoA-transferase (ctfA/B) and acetoacetate decarboxylase (adc) genes. The aforementioned genes were also expressed under control of the acetoacetate decarboxylase promoter. See FIG. 7A & 7B.

Liquid-Liquid Extraction of IBE

A synthetic mixture was prepared with ethanol (5 gl$^{-1}$), isopropanol (5 gl$^{-1}$), and 1-butanol (10 gl$^{-1}$). 5-mL of IBE media was combined with 5 mL of glyceryl tributyrate or oleyl alcohol and mixed for 5 minutes by inversion. The mixtures were then spun down at 5300 RPMs for 5 minutes and the extractant phase removed for GC analysis. Distribution coefficients were calculated based on formula (1) below:

$$K_{D_i} = \frac{\text{Kg of compound } i \text{ in the extractant phase}}{\text{Kg of compound } i \text{ in the aqeous phase}} \quad (1)$$

The extraction experiments were run in triplicate. The experimentally calculated distribution coefficients (gl$^{-1}_{extractant}$/gl$^{-1}_{media}$) of glyceryl tributyrate and oleyl alcohol from synthetic mixtures of ABE and IBE by HPLC and GC-FID are summarized in Table 8 below.

TABLE 8

| Extractant Structure | Name | Acetone $K_D$ | Isopropanol $K_D$ | Butanol $K_D$ |
|---|---|---|---|---|
| (triester structure shown) | Glyceryl Tributyrate | 1.0 ± 0.04 | 0.3 ± 0.02 | 2.6 ± 0.04 |
| (oleyl alcohol structure shown) | Oleyl Alcohol | 0.35* | 0.8 ± 0.07 | 3.6* |

Batch Fermentation

All fermentations of *C. acetobutylicum* strain SACE were conducted in 3-L bioreactors (Bioengineering AG, Switzerland) with a 2 L working volume. Cultures were grown at 37° C. anaerobically by sparging 100 mL/min of $N_2$ gas until solvent production was initiated. The culture pH was adjusted to 6.0 prior to inoculation. Fermentors were inoculated with 100 mL of preculture into 1.5 L of CGM supplemented with 40 ug/mL clathromycin. The bioreactor pH was controlled with 5M KOH at pH>5.0. Sugars and major metabolites (glucose, lactate, acetate, butyrate, acetoin, ethanol, acetone, isopropanol and 1-butanol) were measured in the aqueous phase using an Agilent (Santa Clara, Calif.) HPLC system equipped with refractive index and UV/Vis detectors. A Bio-Rad (Hercules, Calif.) Aminex HPX-87H ion exchange column with a Cation H guard column at 60° C. was used with a mobile phase of 0.05 mM sulfuric acid flowing at 0.7 mL min$^{-1}$.

Figure 6:
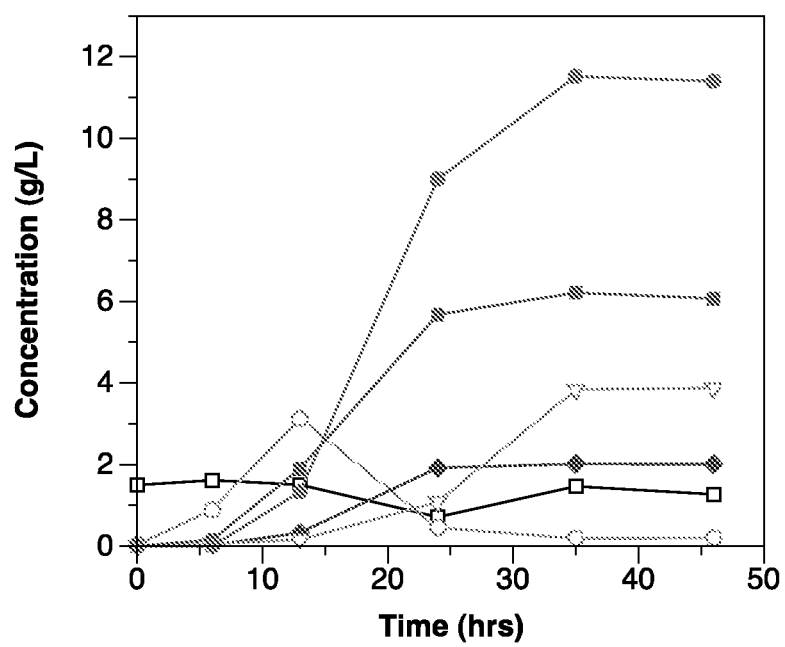
FIG. 6 is a graph depicting the production of acetate (black open square), butyrate (orange open circle), lactate (red diamond), isopropanol (purple square), 1-butanol (blue circle), ethanol (green triangle) as measured by HPLC.

A 1-L batch fermentation of the SACE strain produced in Example 11 was conducted and 21.5 g l$^{-1}$ of alcohols (6.2 gl$^{-1}$ isopropanol, 3.8 g l$^{-1}$ ethanol, and 11.5 gl$^{-1}$ butanol) were produced from 54 g/L of glucose in 35 hours. The results after 46 hours are summarized in FIG. 6.

Extractive Fermentation

Extractive fermentations were operated in fed-batch mode with intermittent addition of a concentrated media solution containing 500 gl$^{-1}$ glucose and 50 gl$^{-1}$ yeast extract. 500 mL of $N_2$ degassed oleyl alcohol was added to the 1 L fermentation broth 16 hours after inoculation. Isopropanol, 1-butanol, and ethanol concentrations were measured in the extractant phase by GC/FID.

Example 12

Effect of Varying pH on Isopropanol Production

Figure 8:
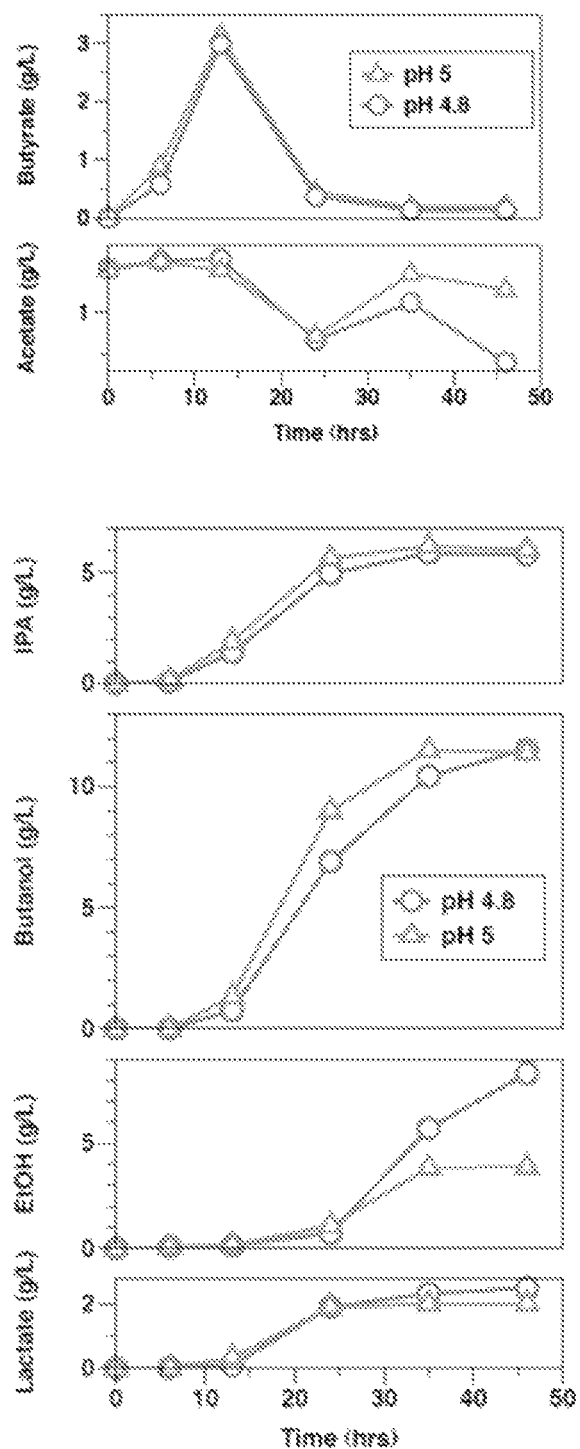
FIG. 8 is a series of graphs depicting the effect of pH on production of isopropanol, butanol, ethanol, butyrate, acetate, and lactate.

This Example demonstrates the effect of varying pH on isopropanol production from fermentation using the SACE strain produced according to the methods in Example 11 above. Acetate was added to regulate pH after solventogenesis and drive isopropanol production. Early initiation of isopropanol production (8 hours). Significant ethanol production was observed after isopropanol production stalled (25 hours). Butanol yield was observed to be 0.2 g/g$_{gluc}$, and isopropanol-butanol-ethanol yield was observed to be 0.38 g/g$_{gluc}$. See FIG. 8.

Example 13

IBE Extractive Fermentation

This Example demonstrates an IBE extractive fermentation using oleyl alcohol as an extractant. Fed batch fermentation was performed, using an initial glucose concentration of 65 g/L. The volume ratio of media to oleyl alcohol used was 2:1 on a 1.5 L scale. The pH was controlled at >5.0. Concentrated media (500 g/L glucose and 50 g/L yeast extract was added periodically. Oleyl alcohol was added once pH was observed to begin to increase (after 16 hours). $N_2$ sparging was suspended after oleyl alcohol addition.

Figure 9:
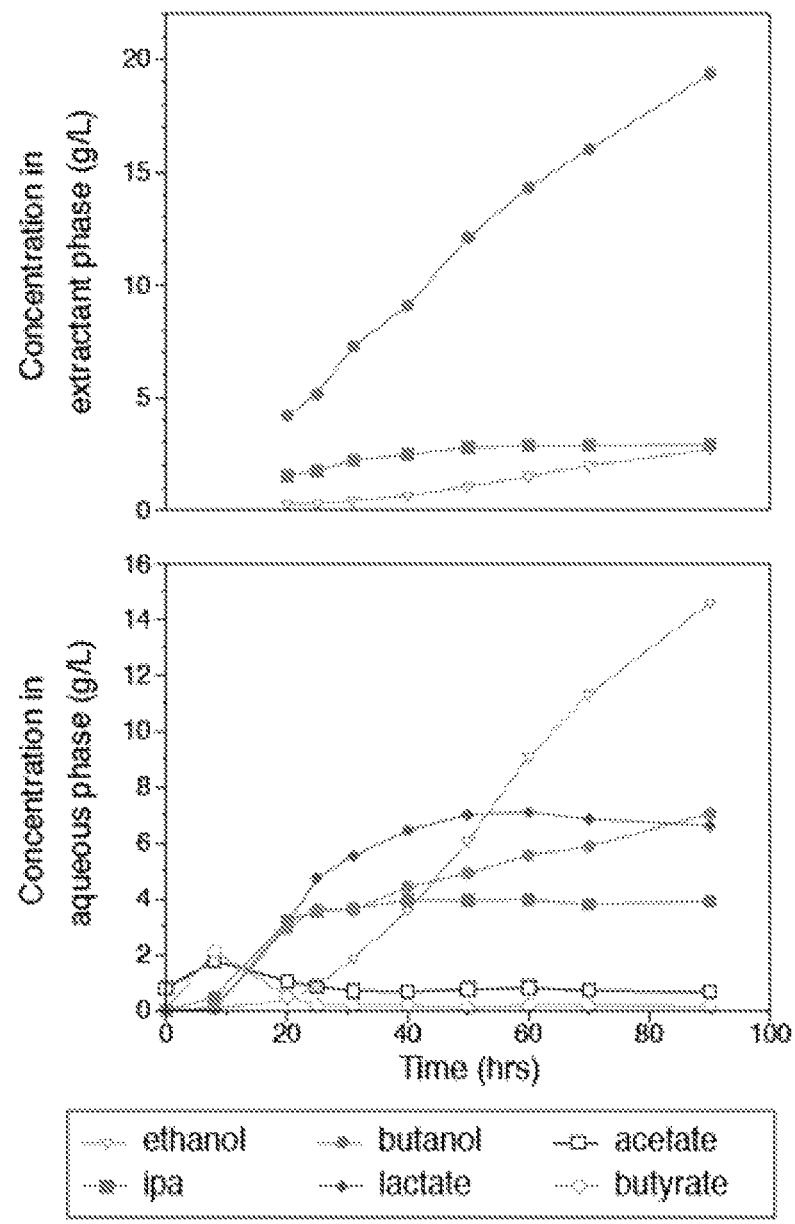
FIG. 9 depicts two graphs showing the concentration of isopropanol, butanol, ethanol, butyrate, acetate, and lactate in the extractant and aqueous phases in an extractive fermentation experiment.

117 g of glucose was consumed. 39.6 IBE was produced (5.6 g isopropanol, 17.9 g butanol, and 16.1 g ethanol). The IBE yield was 0.34 g/g$_{gluc}$ (78% theoretical). See FIG. 9.

Example 14

Effect of Combining Carbon or Zeolite with Catalyst

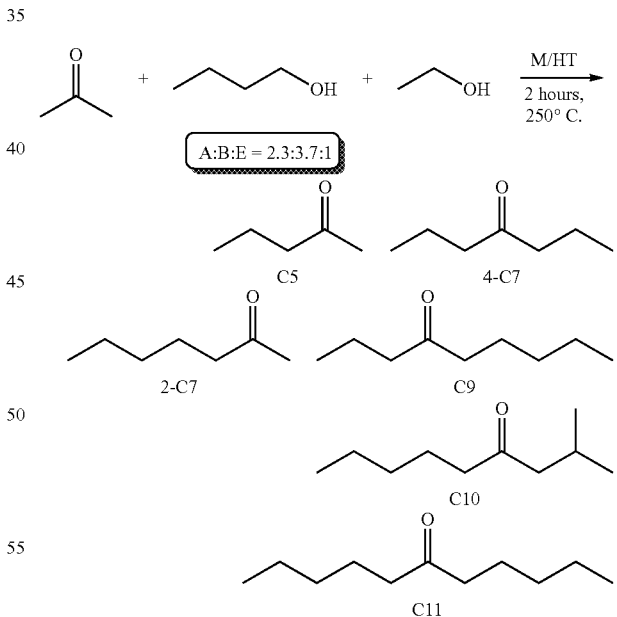

This Example demonstrates the effect of combining carbon or zeolite with the hydrotalcite catalyst on reaction yield. The reaction was performed according to the procedure described in Example 1 above and in accordance with the conditions in the reaction scheme above, using the following: acetone (4.6 mmol), butanol (5.52 mL), ethanol, (5.52 mmol), the type and amount of catalyst and the amount of water used as specified in the Table 9 below.

TABLE 9

| Reaction | Catalyst (g) | Water (μL) | 2-C5 (%) | 2-C7 (%) | 4-C7 (%) | 2-C9 (%) | 6-C11 (%) | Yield (%) |
|---|---|---|---|---|---|---|---|---|
| 1 | 3:1 Pd-Cu/HT (0.35 g) | 100 | 9.8 | 33.3 | — | 5.1 | 8.3 | 56 |
| 2 | 3:1 Pd-Cu/HT + X13-Zeolite (0.35 g + 0.35 g) | 100 | 6.1 | 27.1 | — | 10.5 | 25.9 | 70 |
| 3 | 3:1 Pd-Cu/HT + TiO$_2$ (0.35 g + 0.05 g) | 150 | 9.6 | 15.4 | 0.5 | 0.9 | 0.5 | 27 |
| 4 | 3:1 Pd-Cu/HT-C + TiO$_2$ (0.35 g + 0.05 g) | 150 | 7.3 | 26.3 | 0.7 | 2.3 | 2.8 | 40 |

The catalysts in Table 9 above were obtained or prepared as follows:

3:1 Pd—Cu/HT refers to a 3:1 molar ratio of Pd:Cu impregnated on hydrotalcite;

3:1 Pd—Cu/HT+X13-Zeolite refers to a mixture of 3:1 Pd—Cu/HT (as described above) and the zeolite;

3:1 Pd—Cu/HT+TiO$_2$ refers to a mixture of 3:1 Pd—Cu/HT (as described above) and TiO$_2$;

and 3:1 Pd—Cu/HT-C+TiO$_2$ refers to a mixture of 3:1 Pd—Cu/HT-C and TiO$_2$, in which the Pd—Cu/HT-C was prepared by mixing hydrotalcite and carbon to yield a support, and then impregnating Pd and Cu on the support.

The yields observed were higher in the presence of carbon or zeolite compared to the yields observed when the carbon or zeolite was not added. For example, higher yields of dialkylated compounds such as 6-C11 and 2-C9 were observed when the reactions in this Example were performed in the presence of carbon or zeolite.

Example 15

Comparison of Effects of Liquid-Phase and Gas-Phase Reactor Systems

This Example demonstrates the effects in the phase and surface area of the hydrotalcite-based catalysts over the course of reactions in the liquid and gas phases.

Batch reactor study: 160 mg of Pd—Cu/HT catalyst, 908 μl of acetone-butanol-ethanol (ABE) mix and approximately 100 μl of dodecane were loaded into a Qtube, which was sealed and heated to 513 K. After the reaction, the reaction mixture was cooled to room temperature and diluted with tetrahydrofuran. An aliquot of the mixture was analyzed by gas chromatography. The spent catalysts were subsequently removed by centrifugation and dried.

Gas Phaseflow Reactor Study: About 300 mg of catalyst were placed in a quartz frit on the inside of a tubular reactor. A gas mixture consisting of 85 kPa He and 15 kPa ABE mix was passed over the catalyst at a temperature of 473 K. The reactor effluent was analyzed by online gas chromatography.

Liquid-Phase Flow Reactor Study: 1 g of Pd—Cu/HT catalyst was placed on a stainless steel frit in a tubular stainless steel reactor. A liquid ABE mix was passed over the catalyst at a temperature of 513 K and the effluent of the reactor was collected and analyzed by GC offline.

Figure 12:
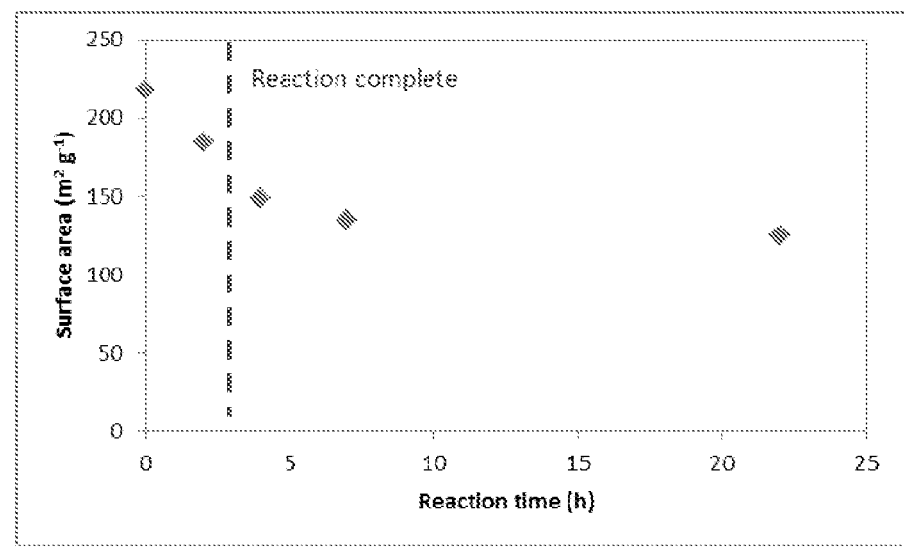
FIG. 12 is a graph depicting dependence of catalyst surface area on reaction time.

As seen in FIG. 12, the surface area of the Pd—Cu/HT catalysts was observed to decrease as the batch reaction time increases. X-ray diffraction patterns of the catalyst in the reaction mixture taken at different times during the reaction also indicated that the catalyst partially changed structure, from the cubic periclase structure to the lamellar hydrotalcite structure. Diffraction patterns of spent catalysts also showed a broad peak centered around 38 degrees 2θ, which may correspond to an amorphous hydrated magnesium/aluminum oxide phase. This structural transition has been attributed to the formation of water during the reaction and the reaction of this water with the Mg$_6$Al$_2$O$_9$ oxide to form the lower-surface-area lamellar structure.

In the liquid phase flow reactor stability study, it was observed that a stabilization of the reactivity of the catalyst after about 24 h on-stream. This contrasts with observations for the gas-phase flow reactor experiments. In these experiments, the observed deactivation was observed to be much more extensive than that observed in the liquid-phase experiments. This deactivation was attributed to the formation of carbonaceous species in the catalyst pores, on the basis of an observed reduction in catalyst surface area during reaction. Phase change or structural collapse of the material was ruled out as the cause of this deactivation behavior, based on the fact that the X-ray diffractogram showed no formation of the lamellar hydrotalcite phase or any increase in domain sizes, as calculated by the XRD line broadening at 2θ=43.5 degrees. Moreover, the BJH distribution of pore sizes showed a shifting of the pore size distribution to larger pore sizes.

Figure 13:
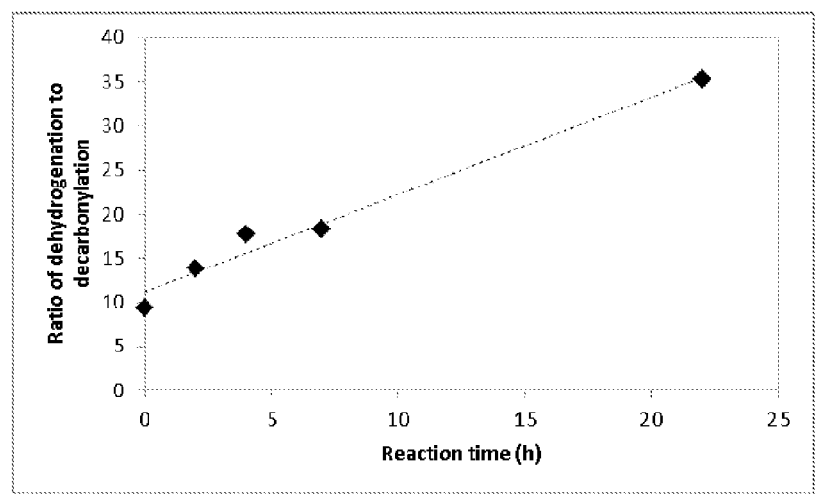
FIG. 13 is a graph depicting the ratio of dehydrogenation to decarbonylation rate as a function of reaction time in the liquid over for PdCu/HT.

As seen in FIG. 13, the ratio of decarbonylation to dehydrogenation was observed to decrease as the catalyst ages. Less carbon loss and defunctionalization was observed as a result of decarbonylation. This behavior may be attributed to increased alloying of Pd and Cu during reaction, resulting in a more selective catalyst.

Example 16

Reaction with 1-Octanol

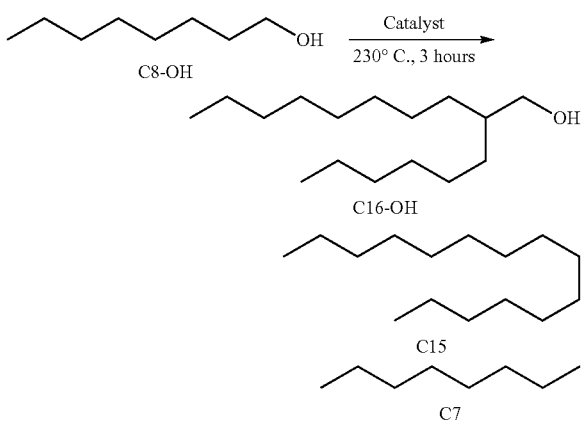

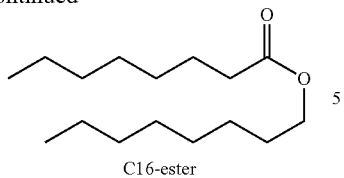

C16-ester

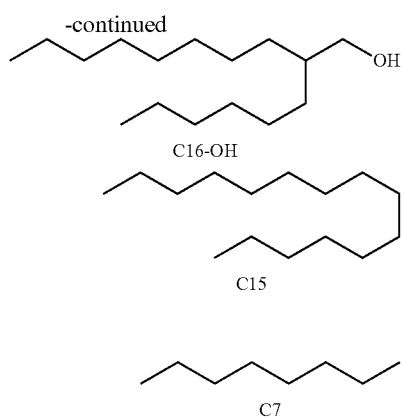

This Example demonstrates the effect of various hydrotalcite catalysts on decarbonylation in the Guerbet reaction of 1-octanol. The reaction was performed according to the procedure described in Example 1 above and in accordance with the conditions in the reaction scheme above, using the following: 1-octanol (3 mmol), the catalyst described in Table 10 below (100 mg). Selectivity was determined by GC.

TABLE 10

| Catalyst No. | (0.9 mol %) | Conv. (%) | C16-OH:C15 | C16-OH:C7 | C16-OH:C16-Ester |
|---|---|---|---|---|---|
| 1 | Pd-HT | 34 | 1:1.5 | 1.8:1 | 4.2:1 |
| 2 | Cu-HT | 34 | >99:1 | >99:1 | 1:2.2 |
| 3 | 3:1 Pd—Cu/HT | 52 | 1.1:1 | 1:1 | 4.3:1 |
| 4 | 3:1 Pd—Cu/HT (used) | 23 | 2.7:1 | 1.5:1 | 7.3:1 |
| 5 | Pd/HT/C | 10 | 3.4:1 | 33:1 | 6.3:1 |
| 6 | 3:1 Pd—Cu/HT/C | 58 | 47:1 | 35:1 | 4.3:1 |

The catalyst for reaction no. 4 was obtained by passing mixture of acetone and ethanol over the fresh catalyst at 250° C. for 24 hours. Improved selectivity for C16-OH was observed. Impregnating HT on carbon support was observed to further suppress decarbonylation.

The reaction in this Example using 1-octanol was repeated in accordance with the reaction scheme below to further compare the effects of impregnating HT on carbon support. The following reaction was performed using (i) Pd—Cu/HT, with a 3:1 molar ratio of Mg:Al in the HT; and (ii) Pd—Cu/5% HT/C, with a 4:1 molar ratio of Mg:Al in the HT.

Figure 14:
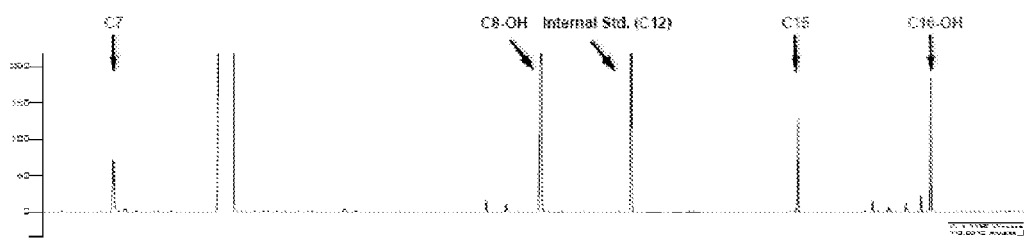
FIGS. 14A and 14B compare decarbonylation in the present of Pd—Cu/HT (FIG. 14A) and Pd—Cu/HT/C (FIG. 14B).
Figure 14:
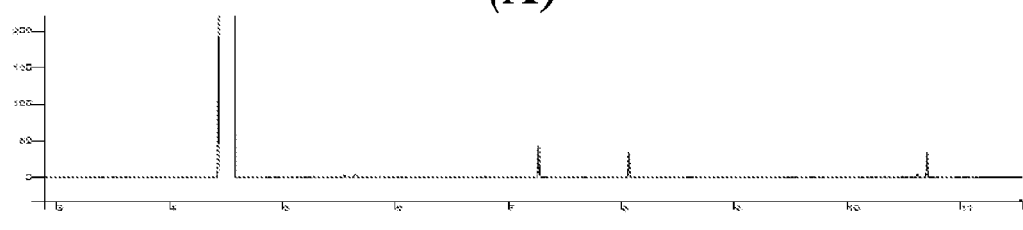

FIGS. 14A (Pd—Cu/HT) and 14B (Pd—Cu/5% HT/C) compare the products formed from the reaction above. As seen in FIG. 14B, when HT was impregnated on carbon support, decarbonylation was suppressed.

Example 17

Tuning of Reaction for C11+Fractions

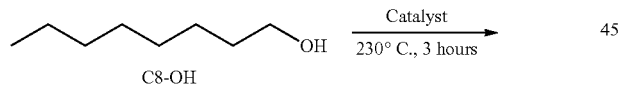

Reaction 1:

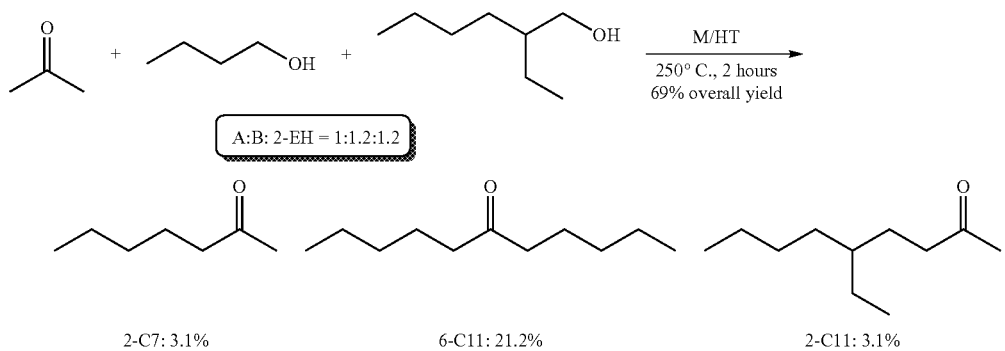

2-C7: 3.1%      6-C11: 21.2%     2-C11: 3.1%

Reaction 2:

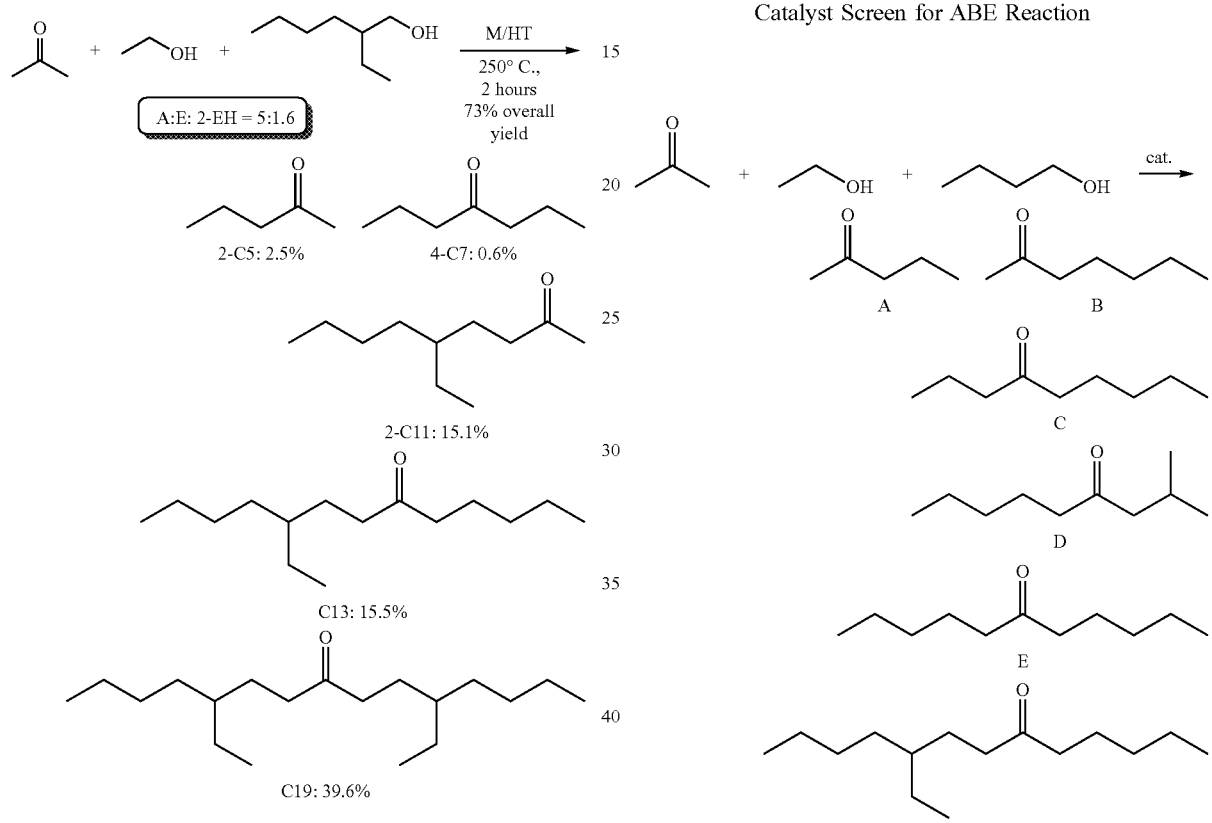

This Example demonstrates the effect of using Pd—Cu/HT combined with TiO$_2$ as the catalyst to tune the reaction for C11+ fractions. The reaction was performed according to the procedure described in Example 1 above and in accordance with the conditions in the reaction scheme above, using the following:

Reaction 1: A:B:2-EH=4.6:5.52:5.52 mmol, M/HT=2 wt % Pd—Cu/HT+TiO$_2$=(0.35+0.05) g; and Reaction 2: A:E:2-EH=5:1:6 mmol, M/HT=2 wt % Pd—Cu/HT+TiO$_2$=(0.35+0.05) g.

Selectivity for C11+ fractions were determined by GC-FID in accordance with the following:

Reaction 1: selectivity=[wt. (C11+C15+C19)/Total wt. C7-C19]×100; and

Reaction 2: selectivity=[wt. (C11+C13+C19)/Total wt. C5-C19]×100.

In both reactions, selectivity for C11+ fractions was observed to be greater than 95 wt %.

Example 18

Catalyst Screen for ABE Reaction

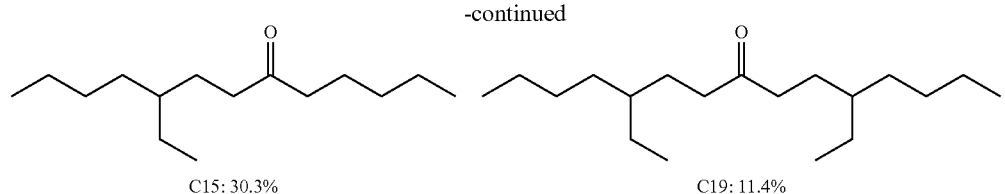

This Example demonstrates the effect of various catalysts on the ABE reaction. The reaction was performed according to the procedure described in Example 1 above and in accordance with the conditions set forth under each table below.

Generally, for all carbon based catalysts, metal oxides impregnated on carbon were prepared by incipient wetness impregnation of an aqueous solution of the metal nitrate(s) onto the carbon support. The solid was dried at 110 C at ambient air and treated under a flow of He (100 ml/min) at 400° C. or 500° C. for 4 h (5° C./min).

Generally, for all non-carbon supported catalysts, metal oxides impregnated diverse supports (e.g., La2O3, TiO2, HT, and SiO$_2$) were prepared by incipient wetness impregnation of an aqueous or organic solution of the metal nitrate(s), acetates, or acetylacetonates onto the support. The solid was dried at 110 C at ambient air and calcined under stagnant ambient air at 300 to 900 C (1 to 10 C/min ramp rate).

TABLE 11

| Catalyst | A | B (2C7 + 4C7) | C | D | E | F | Total Alcohols | Overall Yield |
|---|---|---|---|---|---|---|---|---|
| HiFuel ® + Hydroxyapatite | 2.4 | 21.3 | 0.5 | 0.3 | 1.3 | — | 0.2 | 26 |
| HiFuel ® + Perovskite | 0.5 | 22.7 | 0.6 | — | 5.1 | — | 4.0 | 32.9 |
| Cu/MgO | 2.8 | 21.8 | 4.8 | 0.3 | 23.4 | — | 4.6 | 57.7 |
| HiFuel ® + HTO3 | 0.7 | 2.0 | 1.7 | 0.3 | 21.5 | 1.9 | 37.1 | 65.2 |
| HiFuel ® + HT(commercial) | 0.5 | 6.0 | 1.6 | 0.5 | 20.0 | 1.8 | 28.3 | 58.7 |

Reaction conditions: 2.3 mmol acetone, 3.7 mmol butanol, 1 mmol ethanol, 350 mg of the catalyst set forth in Table 11 above in 1 mL butanol, reacted for 20 hours at 240° C.

It should generally be understood that HiFuel® refers to a Cu/ZnO/Al$_2$O$_3$ catalyst that was obtained from a commercially available source. HiFuel® may be prepared by coprecipitation of Cu, Zn, and Al oxides followed by reduction. The catalysts in Table 11 above were obtained or prepared as follows:

HiFuel®+ hydroxyapatite refers to a mixture of HiFuel® and Hydroxyapatite, both of which were obtained from commercially available sources;

HiFuel®+ perovskite refers to a mixture of HiFuel® and perovskite made by precipitation of Ti-isopropoxide and Sr-isopropoxide;

Cu/MgO refers to Cu impregnated on MgO by incipient wetness impregnation;

HiFuel®+HTO3 refers to physical mixture of HiFuel® and HTO3, where HTO3 refers to a hydrotalcite prepared by coprecipitating magnesium nitrate and aluminum nitrate using ammonium hydroxide and ammonium nitrate, and the resulting solid is filtered and calcined at 550° C.; and HiFuel®+HT (commercial) refers to HiFuel® impregnated on hydrotalcite that was purchased from a commercially available source.

TABLE 12

| Catalysts | A | B (2C7 + 4C7) | C | D | E | F | Total Alcohols | Overall Yield |
|---|---|---|---|---|---|---|---|---|
| HiFuel ® + BaO/SiO$_2$ | | | | | | | | ~0 |
| HiFuel ® + MgO/SiO$_2$ | | | | | | | | ~0 |
| HiFuel ® + SrO/SiO$_2$ | 0.8 | 6.7 | 0.2 | 0.2 | — | 0.1 | — | 8.0 |
| HiFuel ® + CaO/SiO$_2$ | 1.9 | 15.9 | 0.3 | — | 0.6 | — | 0.6 | 19.3 |
| HiFuel ® + SrO/MgO (1%) | 2.7 | 17.8 | 2.6 | 0.7 | 11.9 | — | 1.8 | 37.5 |
| HiFuel ® + SrO/MgO (2%) | 1.9 | 13.4 | 1.6 | 0.4 | 7.8 | — | 1.1 | 26.2 |
| HiFuel ® + CaO/MgO (10%) | 2.0 | 12.2 | 6.3 | 1.1 | 28.1 | — | 3.1 | 52.8 |
| HiFuel ® + CaO/MgO (5%) | 2.5 | 15.5 | 4.2 | 0.7 | 19.5 | — | 2.4 | 44.8 |
| HiFuel ® + CaO/MgO (1%) | 2.2 | 10.7 | 7.1 | 1.0 | 27.0 | — | 5.1 | 53.1 |
| Cu/SiO$_2$ + CaO/MgO (10%) | 2.0 | 17.9 | 3.5 | 0.7 | 19.0 | — | 1.1 | 44.2 |
| Cu/SiO$_2$ + CaO/MgO (5%) | 1.3 | 14.0 | 2.2 | 0.6 | 14.5 | — | 1.5 | 34.1 |
| Cu/SiO$_2$ + CaO/MgO (2%) | 1.5 | 13.6 | 3.7 | 0.6 | 22.2 | — | 2.1 | 43.7 |
| Cu/SiO$_2$+ CaO/MgO (1%) | 1.7 | 15.5 | 4.0 | 0.7 | 23.4 | — | 2.0 | 47.3 |
| Pd-Cu/CaO/MgO (1%) | 5.1 | 22.8 | 8.3 | 0.4 | 19.7 | — | 2.0 | 58.3 |
| Pd-Cu/HTO3 | 5.2 | 25.9 | 9.7 | 1.1 | 24.7 | — | 2.5 | 69.1 |
| Pd-Cu/NiHT (1:10) | 5.3 | 24.9 | 9.3 | 1.1 | 20.7 | — | 1.9 | 63.2 |
| Cu/NiHT (1:10) | 4.0 | 28.3 | 4.0 | 0.7 | 14.5 | — | 3.12 | 54.6 |
| Pd-Cu/ZnHT (3:1 molar Pd:Cu, on support with Zn:Mg 1:1 molar and Zn + Mg:Al 3:1) | 3.5 | 18.0 | 1.2 | 0.3 | 2.8 | — | 0.9 | 26.7 |
| Cu/ZnHT (2 wt % Cu on support having Zn:Mg 1:1 molar and Zn + Mg:Al 3:1) | 3.8 | 24.4 | 1.5 | 0.3 | 5.9 | — | 1.0 | 36.9 |
| Pd-Cu/ZnHT (1:1, Zn:Mg) | 3.1 | 18.3 | 5.0 | 1.0 | 18.8 | — | 1.6 | 47.8 |
| Cu/ZnHT (1:1, Zn:Mg) | 4.4 | 29.0 | 4.3 | 0.8 | 16.2 | — | 1.4 | 56.1 |
| Pd-Cu/ZnHT (1:10, Zn:Mg) | 2.8 | 17.2 | 5.2 | 1.0 | 15.2 | — | 22.0 | 63.4 |
| Cu/ZnHT (1:10, Zn:Mg) | 3.5 | 26.8 | 5.8 | 1.2 | 21.2 | — | 1.6 | 60.1 |
| Ru/HT | 3.4 | 20.1 | 2.9 | 0.2 | 10.7 | — | 5.4 | 42.7 |
| Cu-Ru/HT | 1.4 | 9.7 | 1.5 | 0.1 | 7.4 | — | 6.0 | 26.1 |
| Co/HT* | | | | | | | | ~0 |
| Pt/HT* | 1.1 | 7.1 | 5.6 | 0.5 | 18.6 | — | 25.7 | 58.6 |
| Pt-Cu/HT* | 1.3 | 7.3 | 4.9 | 0.5 | 13.8 | — | 26.4 | 54.2 |

Reaction conditions: 4.6 mmol acetone, 7.4 mmol butanol, 2 mmol ethanol, 350 mg of the catalyst set forth in Table 12 above, reacted for 2 hours at 250° C. The reactions in Table 12 denoted with an asterisk (*) were run for 20 hours.

The catalysts in Table 12 above were obtained or prepared as follows:

HiFuel®+BaO/SiO$_2$ refers to a mixture of HiFuel® and BaO impregnated on SiO$_2$ by Incipient wetness impregnation of Ba(NO$_3$) followed by calcination;

HiFuel®+MgO/SiO$_2$ refers to a mixture of (i) HiFuel® and (ii) MgO impregnated on SiO$_2$ by the method described above;

HiFuel®+SrO/SiO$_2$ refers to a mixture of (i) HiFuel® and (ii) SrO impregnated on SiO$_2$ by the method described above;

HiFuel®+CaO/SiO$_2$ refers to a mixture of (i) HiFuel® and (ii) CaO impregnated on SiO$_2$ by the method described above;

HiFuel®+SrO/MgO (x %) refers to a mixture of (i) HiFuel® and (ii) x mol % SrO co-precipitated on MgO by calcination of coprecipitated Sr—Mg oxalate;

HiFuel®+CaO/MgO (x %) refers to a mixture of (i) HiFuel® and (ii) x mol % CaO co-precipitated on MgO by the method described above;

Cu/SiO$_2$+CaO/MgO (x %) refers to a mixture of (i) Cu impregnated on SiO$_2$, and (ii) x mol % CaO co-precipitated on MgO by calcination of coprecipitated Ca—Mg oxalate;

Pd—Cu/CaO/MgO (x %) refers to a mixture of Pd and Cu impregnated on x % CaO and MgO prepared by the method described above;

Pd—Cu/HTO3 refers to Pd and Cu Incipient wetness impregnation catalyst on HTO3, where HTO3 is prepared as described above;

Pd—Cu/NiHT (x:y) refers to a mixture of Pd and Cu impregnated on a nickel hydrotalcite structure, and this catalyst was prepared by incipient wetness impregnation of 3:1 Pd:Cu mixture onto a calcined hydrotalcite structure made up of Ni, Mg, Al, and oxygen (where the ratio of Ni:Mg was x:y, and the ratio of (Ni+Mg):Al was 3:1, and the oxygen was as stoichiometrically required), and the hydrotalcite was prepared by coprecipitation of nickel, magnesium and aluminum nitrates, as described above;

Cu/NiHT (x:y) refers to a mixture of Cu impregnated on a nickel hydrotalcite as described above;

Pd—Cu/ZnHT(x:y) refers to a composite prepared by incipient wetness impregnation of a 3:1 Pd:Cu onto a calcined hydrotalcite structure made up of Zn, Mg, Al and oxygen (where the ratio of Zn:Mg is x:y, the ratio of (Zn+Mg):Al is 3:1, and the oxygen is the stoichiometrically required), and the hydrotalcite was prepared by coprecipitation of zinc, magnesium and aluminum nitrates, as described above;

Cu/ZnHT refers to a composite prepared by incipient wetness impregnation of Cu onto a calcined hydrotalcite structure made up of Zn, Mg, Al and oxygen as described above;

Ru/HT refers to a calcined hydrotalcite structure made up of Ru, Mg, Al and oxygen, prepared as described above;

Cu—Ru/HT refers to a composite prepared by incipient wetness impregnation of Cu onto a calcined hydrotalcite structure made up of Ru, Mg, Al and oxygen, prepared as described above;

Co/HT refers to a composite prepared by incipient wetness impregnation of Co onto a calcined hydrotalcite structure prepared as described above;

Pt/HT to a composite prepared by incipient wetness impregnation of Pt onto a calcined hydrotalcite structure prepared as described above; and Pt—Cu/HT refers to a composite prepared by incipient wetness impregnation of a mixture of Pt and Cu onto a calcined hydrotalcite structure prepared as described above.

TABLE 13

| Catalyst | A | B (2C7 + 4C7) | C | D | E | F | Total Alcohols | Overall Yield |
|---|---|---|---|---|---|---|---|---|
| Cu/SiO$_2$ + Pd/C + 10% CaO/C | 0.7 | 36.5 | 6.1 | 0.4 | 8.9 | — | 3.4 | 56 |
| Cu/SiO$_2$ + Pd/C + 10% SrO/C | 0.3 | 30.2 | 0.9 | 0.2 | 2.2 | — | 3.6 | 37 |
| Cu/SiO$_2$ + Pd/C + 4% BaO/C | 1.0 | 9.5 | 0.2 | 1.0 | 1.3 | — | 3.9 | 17 |
| Cu/SiO$_2$ + Pd/C + 5% La$_2$O$_3$/C | 0.3 | 25.2 | 1.6 | 0.3 | 3.9 | — | 4.3 | 36 |
| Cu/SiO$_2$ + Pd/C + 10% CeO$_2$/C | 0.3 | 24.6 | 1.7 | 0.3 | 4.1 | — | 3.4 | 34 |
| Cu/SiO$_2$ + Pd/C + 11.6% HT/C | 1.3 | 39.6 | 2.5 | 0.3 | 9.0 | — | 2.2 | 55 |
| Cu/SiO2 + Pd/C + HT | 0.5 | 3.6 | — | — | 0.1 | — | 3.4 | 7.6 |

Reaction conditions: 4.6 mmol acetone, 7.4 mmol butanol, 2 mmol ethanol, 350 mg of the catalyst set forth in Table 13 above, reacted for 3-4 hours at 200° C. A mixture of the three catalysts listed for each reaction was used, and the three catalysts were obtained from commercially available sources or prepared as described herein.

TABLE 14

| Catalyst | A | B (2C7 + 4C7) | C | D | E | F | Total Alcohols | Overall Yield |
|---|---|---|---|---|---|---|---|---|
| HiFuel ® + HT | 4.0 | 24.0 | 3.8 | 1.1 | 13.6 | — | — | 46.5 |
| HiFuel ® + Pd/C + HT | 4.3 | 22.1 | 4.2 | 0.7 | 11.1 | — | — | 42.4 |
| HiFuel ® + CeO$_2$ | 3.5 | 21.6 | 3.5 | 1.9 | 11.0 | — | — | 41.5 |
| HiFuel ® + Pd/C +CeO$_2$ | 4.2 | 21.3 | 9.0 | 1.3 | 28.1 | — | — | 63.9 |
| HiFuel ® + La$_2$O$_3$ (from La$_2$(C$_2$O$_4$)$_3$) | 4.1 | 16.7 | 9.2 | 1.0 | 27.3 | — | — | 58.3 |
| HiFuel ® + Pd/C + La$_2$O$_3$ (from La$_2$(C$_2$O$_4$)$_3$) | 3.3 | 14.8 | 8.1 | 0.2 | 26.4 | — | — | 52.8 |
| HiFuel ® + La$_2$O$_3$ (from La$_2$(NO$_3$)$_3$) | 3.7 | 17.6 | 4.6 | 1.1 | 16.0 | — | — | 43.0 |
| HiFuel ® + Pd/C + La$_2$O$_3$ (from La$_2$(NO$_3$)$_3$) | 3.8 | 19.9 | 8.9 | 0.1 | 32.2 | — | — | 64.9 |

Reaction conditions: 4.6 mmol acetone, 7.4 mmol butanol, 2 mmol ethanol, 350 mg of the catalyst set forth in Table 14 above (and 25 mg HiFuel®, 70 mg Pd/C, where applicable), reacted for 2 hours at 250° C. A mixture of the three catalysts listed in Table 15 above for each reaction was used, and the three catalysts were obtained from commercially available sources or prepared as described herein. It should generally be understood that La$_2$O$_3$ may be prepared from the calcination of La$_2$(C$_2$O$_4$)$_3$ or La$_2$(NO$_3$)$_3$ (as indicated in Table 14 above) at or above 500° C.

Example 19

Catalyst Screen for Acetone-Butanol-(2-Ethylhexanol) Reaction

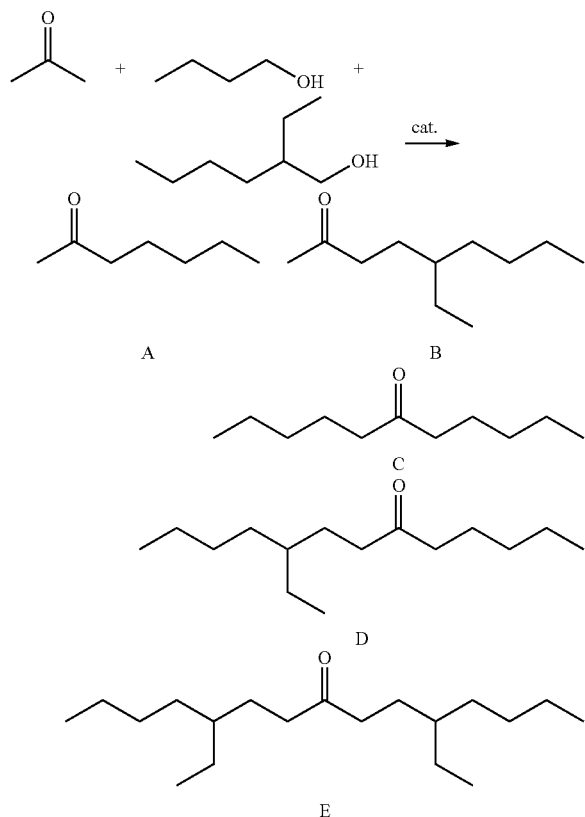

This Example demonstrates the effect of various catalysts on the acetone-butanol-(2-ethylhexanol) reaction. The reaction was performed according to the procedure described in Example 1 above and in accordance with the following conditions: 4.60 mmol acetone, 5.52 mmol butanol, 5.52 mmol 2-ethylhexanol, 350 mg of the catalyst set forth in Table 14 above (and 25 mg HiFuel®, 70 mg Pd/C, where applicable), reacted for 2 hours at 250° C. A mixture of the catalysts listed in Table 15 below for each reaction was used, and the catalysts were obtained from commercially available sources or prepared as described herein.

TABLE 15

| Catalyst | A | B | C | D | E | Overall Yield |
|---|---|---|---|---|---|---|
| HiFuel® + Pd/C + La$_2$O$_3$ | 13.4 | 11.3 | 14.5 | 25.9 | 12.5 | 77.6 |
| HiFuel® + Pd/C + La$_2$O$_3$ + TiO$_2$ | 13.0 | 9.3 | 12.9 | 19.7 | 8.7 | 63.6 |
| HiFuel® + Pd/C + CeO$_2$ | 13.7 | 9.5 | 9.2 | 13.5 | 5.4 | 51.3 |
| HiFuel® + Pd/C + CeO$_2$ + TiO$_2$ | 14.8 | 8.1 | 8.1 | 10.3 | 3.5 | 44.8 |

The invention claimed is:

1. A method of producing a mixture of hydrocarbon ketones, comprising contacting acetone and at least two or more primary alcohols with catalyst and optionally base to produce a mixture of hydrocarbon ketones, wherein at least a portion of the mixture of hydrocarbon ketones is produced from double alkylation of the acetone, and
   wherein the catalyst comprises Pd, Cu, and hydrotalcite (HT).

2. The method of claim 1, wherein the Pd and Cu are coprecipitated or impregnated on the HT.

3. The method of claim 1, wherein the catalyst further comprises Ni, Zn, Ru, Co, or Pt, or any combination thereof.

4. The method of claim 1, wherein the catalyst further comprises zeolite.

5. A method of producing a mixture of hydrocarbon ketones, comprising contacting acetone and at least two or more primary alcohols with catalyst and optionally base to produce a mixture of hydrocarbon ketones, wherein at least a portion of the mixture of hydrocarbon ketones is produces from doubly alkylation of the acetone, and
   wherein the catalyst comprises Pd—Cu/HT, Pd—Cu/HT-C, Pd—Cu/HT/C, Pd—Cu/NiHT, or PdCu/ZnHT, or any combinations thereof.

6. The method of claim 1, wherein at least 70% of the mixture of hydrocarbon ketones are produced from double alkylation of the acetone.

7. The method of claim 1, wherein the mixture of hydrocarbon ketones is a mixture of $C_{5-15}$ hydrocarbon ketones.

8. The method of claim 1, wherein the mixture of hydrocarbon ketones is selected from the group consisting of 2-pentanone, 4-heptanone, 2-heptanone, 4-nonanone, 2-methyl-4-nonanone, 6-undecanone, 5-ethylundecan-6-one, 5,7-diethylundecan-6-one, 5,7-dibutylundecan-6-one, 9-ethyltridecan-6-one, 5,11-diethylpentadecan-8-one, 5-butylundecan-6-one, 5-butyl-7-ethylundecan-6-one, and any combinations thereof.

9. A method of producing a mixture of hydrocarbon ketones, comprising:
   a) contacting biomass or sugars with a fermentation host to produce a fermentation product mixture, wherein the fermentation product mixture comprises acetone, butanol and ethanol;
   b) isolating at least a portion of the acetone, butanol and ethanol from the fermentation product mixture; and
   c) contacting the isolated acetone, butanol and ethanol with metal catalyst and optionally base to produce a mixture of hydrocarbon ketones, wherein at least 20% of the mixture of hydrocarbon ketones are $C_{7+}$ hydrocarbon ketones and wherein at least a portion of the mixture of hydrocarbon ketones is produced from doubly alkylation of the acetone, and
   wherein the catalyst comprises Pd, Cu, and hydrotalcite (HT).

10. The method of claim 1, wherein at least 70% of the mixture of hydrocarbon ketones is $C_{7+}$ hydrocarbon ketones.

11. The method of claim 1, wherein the base is selected from the group consisting of K$_3$PO$_4$, KOH, Ba(OH)$_2$.8H$_2$O, K$_2$CO$_3$, KOAc, KH$_2$PO$_4$, Na$_2$HPO$_4$, pyridine, Et$_3$N, and any combinations thereof.

12. The method of claim 1, wherein the metal catalyst further comprises TiO$_2$, zeolite, or a combination thereof.

13. The method of claim 1, wherein the catalyst comprises:
   Pd—Cu/HT;
   Pd—Cu/HT/C;
   Pd—Cu/HT and zeolite;
   Pd—Cu/HT/C and zeolite;
   Pd—Cu/HT and TiO$_2$;
   Pd—Cu/HT-C and TiO$_2$;
   Pd—Cu/HT/C and TiO$_2$;
   Pd—Cu/C and HT;

Pd—Cu/HT-C;
Pd—Cu/NiHT;
Pd—Cu/ZnHT;
Cu/SiO$_2$, Pd/C and HT/C;
Cu/SiO$_2$, Pd/C and HT;
Cu/ZnO/Al$_2$O$_3$, Pd/C and HT; or
Pd—Cu/ZnO/HT.

14. The method of claim 1, wherein the HT is coprecipitated or impregnated on carbon to form a support, and the Pd and Cu are coprecipitated or impregnated on the support.

15. The method of claim 1, wherein the HT is mixed with carbon to form a support, and the Pd and Cu are coprecipitated or impregnated on the support.

16. The method of claim 1, wherein at least 40% of the mixture of hydrocarbon ketones is $C_{11+}$ hydrocarbon ketones.

* * * * *